United States Patent
Zaidi

(10) Patent No.: US 11,034,761 B2
(45) Date of Patent: Jun. 15, 2021

(54) COMPOSITIONS AND METHODS FOR REDUCING ADIPOSITY BY INHIBITING FSH/FSHR

(71) Applicant: Icahn School of Medicine at Mount Sinai, New York, NY (US)

(72) Inventor: Mone Zaidi, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 16/317,352

(22) PCT Filed: Jul. 24, 2017

(86) PCT No.: PCT/US2017/043518
§ 371 (c)(1),
(2) Date: Jan. 11, 2019

(87) PCT Pub. No.: WO2018/022505
PCT Pub. Date: Feb. 1, 2018

(65) Prior Publication Data
US 2019/0241651 A1 Aug. 8, 2019

Related U.S. Application Data

(60) Provisional application No. 62/510,087, filed on May 23, 2017, provisional application No. 62/368,651, filed on Jul. 29, 2016.

(51) Int. Cl.
| | | |
|---|---|---|
| *C07K 16/26* | (2006.01) | |
| *A61P 3/04* | (2006.01) | |
| *A61K 38/00* | (2006.01) | |
| *A61K 39/00* | (2006.01) | |
| *A61K 35/00* | (2006.01) | |

(52) U.S. Cl.
CPC .............. *C07K 16/26* (2013.01); *A61K 38/00* (2013.01); *A61P 3/04* (2018.01); *A61K 35/00* (2013.01); *A61K 2039/505* (2013.01); *C07K 2317/24* (2013.01); *C07K 2317/34* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 2002/0127227 A1 | 9/2002 | Holmes et al. |
| 2005/0108791 A1 | 5/2005 | Edgerton |
| 2008/0248494 A1 | 10/2008 | Butlin et al. |
| 2009/0324604 A1 | 12/2009 | Liu et al. |
| 2010/0061976 A1* | 3/2010 | Ishikawa ............... A61K 31/00 514/1.1 |
| 2010/0196392 A1 | 8/2010 | Shiraishi et al. |
| 2012/0121576 A1* | 5/2012 | Seehra ............... C07K 16/2863 424/130.1 |
| 2013/0150403 A1 | 6/2013 | Narayanan et al. |
| 2014/0004121 A1 | 1/2014 | Fanslow, III et al. |
| 2016/0194392 A1 | 7/2016 | Honegger et al. |

OTHER PUBLICATIONS

Piche-Nicholas et al., MAbs. 2018; 10: 81-94. doi: 10.1080/19420862. 2017.1389355 (Year: 2018).*
Winkler, Ther. Deliv. 2013; 4: 791-809 (Year: 2013).*
Jafarlou et al., Journal of Biological Regulators & Homeostatic Agents, 2016: 30: 315-321 (Year: 2016).*
Pau et al., Vaccine 19 (2001) 2716-2721 (Year: 2001).*
Gera et al., PNAS, 2020; 117: 28971-28979 (Year: 2020).*
Zhu et al., "Blocking antibody to the b-subunit of FSH prevents bone loss by inhibiting bone resorption and stimulating bone synthesis", Proceedings of the National Academy of Sciences, vol. 109, No. 36, Sep. 2012, pp. 14574-14579.
Liu et al., "FSH regulates fat accumulation and redistribution in aging through the Gai/Ca2+/CREB pathway", Aging Cell, vol. 14, No. 3, Jun. 2015, pp. 409-420.
Armani et al., "Mineralocorticoid receptor antagonism induces browning of white adipose tissue through impairment of autophagy and prevents adipocyte dysfunction in high-fat-diet-fed mice", The FASEB Journal, vol. 28, No. 8, Aug. 2014, pp. 3745-3757.
Du et al., "Molecular Basis of Recognition of Human Osteopontin by 23C3, a Potential Therapeutic Antibody for Treatment of Rheumatoid Arthritis", Journal of Molecular Biology, Academic Press, vol. 382, No. 4, Oct. 2008, pp. 835-842.
Caldas et al., "Humanization of the anti-CD18 antibody 61: an unexpected effect of a framework residue in binding to antigen", Molecular Immunology, vol. 39, No. 15, May 2003, pp. 941-952.
Liu et al., "Blocking FSH induces thermogenic adipose tissue and reduces body fat", Nature, vol. 546, No. 7656, Jun. 2017, pp. 107-112.
The partial supplementary European search report dated Mar. 2, 2020 issued in the corresponding European patent application No. 17835055.9.

* cited by examiner

*Primary Examiner* — Christina M Borgeest
(74) *Attorney, Agent, or Firm* — Fox Rothschild LLP

(57) ABSTRACT

The present disclosure provides compositions and methods for reducing adiposity by inhibiting FSH/FHSR in a subject in need thereof.

22 Claims, 44 Drawing Sheets
Specification includes a Sequence Listing.

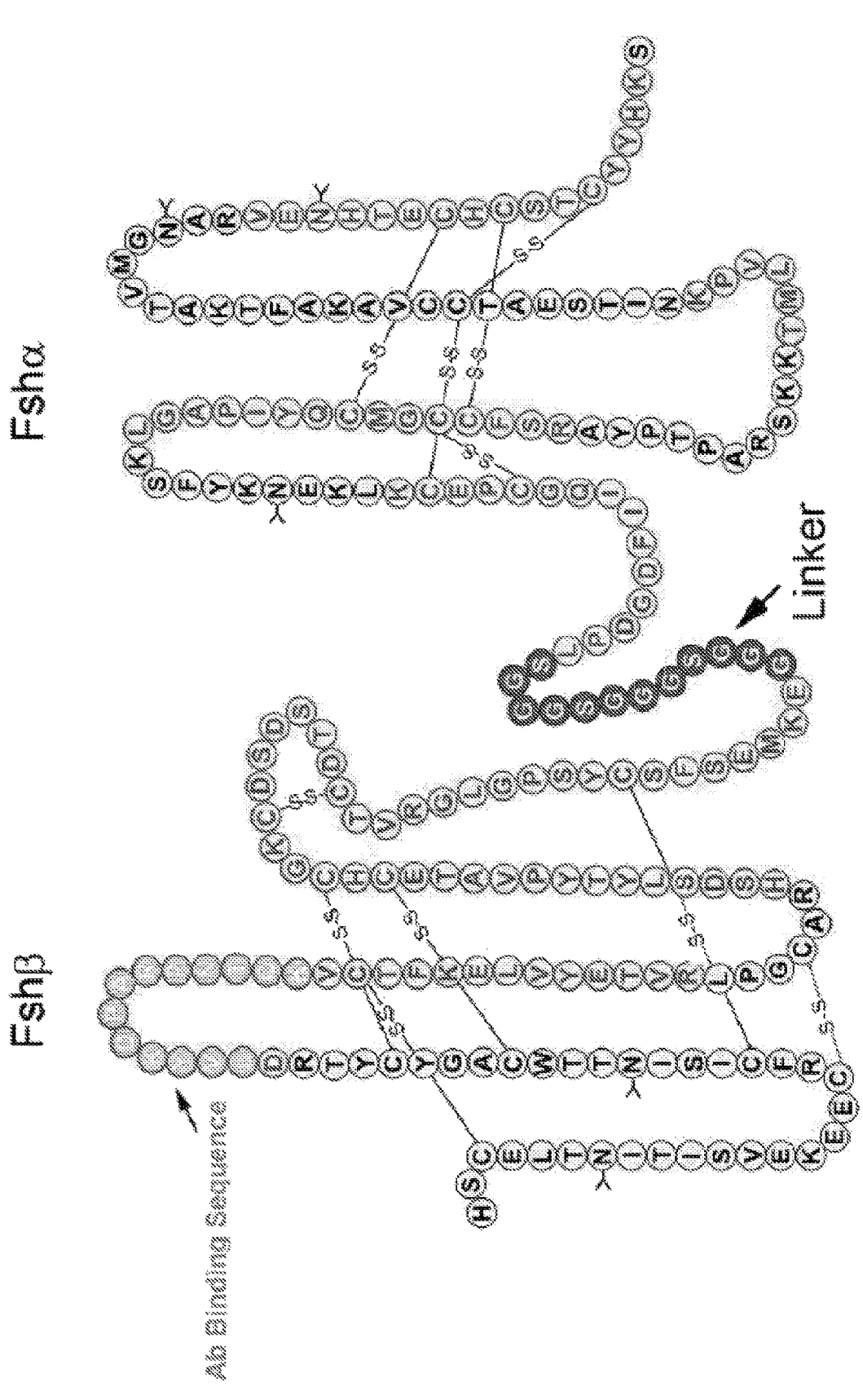
FIG. 2 (Cont'd) Mass Spectrometry

COMPOSITIONS AND METHODS FOR REDUCING ADIPOSITY BY INHIBITING FSH/FSHR

CROSS-REFERENCE TO RELATED APPLICATIONS

The present application claims priority to U.S. Provisional Patent Application Ser. No. 62/368,651, filed Jul. 29, 2016, the disclosure of which is hereby incorporated by reference in its entirety, and to U.S. Provisional Patent Application Ser. No. 62/510,087, filed May 23, 2017, the disclosure of which is hereby incorporated by reference in its entirety.

STATEMENT REGARDING FEDERAL FUNDING

This invention was made with government support under grant numbers DK080459, DK113627, AG040132, AG023176, AR065932, and AR067066 awarded by the National Institutes of Health. The government has certain rights in the invention.

FIELD OF THE INVENTION

The field of the invention is to compositions and methods for reducing adiposity in a subject in need thereof.

BACKGROUND

The perimenopausal transition in women is associated with increases in total body fat and decrements in energy expenditure and physical activity, all of which impact quality of life. Late perimenopause in particular is characterized by a sharp increase in visceral adiposity, which coincides with the emergence of disrupted energy balance and reduced physical activity. Perimenopause is also characterized by relatively stable estrogen and rising levels of follicle stimulating hormone (FSH), which become elevated as the ability to procreate ceases. FSH is a glycoprotein hormone synthesized and secreted by the pituitary. It causes the synthesis and secretion of estrogen by interacting with its receptor, the FSH receptor, on the follicular cell of the ovary. Estrogen levels, in turn, control FSH release from the pituitary through a well-known feedback mechanism. Thus, when estrogen rises, FSH falls. FSH has, however, never been implicated directly in causing an increase in adiposity. Accordingly, there exists a need to identify additional factors that contribute to increase in visceral adiposity and an urgent need for treatments to reduce such.

SUMMARY OF THE INVENTION

The present disclosure relates to the surprising discovery that inhibiting follicle stimulating hormone (FSH) from binding to its receptor (FSHR) reduces adiposity in a subject in need thereof by reducing white adipose tissue (WAT) and increasing thermogenic "beige" adipose tissue, as well monoclonal antibodies and antigen-binding portions thereof that specifically bind to, and inhibit, FSH.

In some embodiments, the present disclosure comprises an anti-FSH antibody or antigen-binding portion thereof. In some embodiments, the anti-FSH antibody is a monoclonal antibody or antigen-binding portion thereof. In some embodiments, the anti-FSH antibody or antigen-binding portion thereof comprises Hf2 or an antigen-binding portion thereof. In some embodiments, the anti-FSH antibody or antigen-binding portion thereof specifically binds to an epitope within SEQ ID NO: 1. In some embodiments, the anti-FSH antibody or antigen-binding portion thereof specifically binds to an epitope within SEQ ID NO: 2.

In some embodiments, the anti-FSH antibody has a variable heavy chain region. In some embodiments, the variable heavy chain region comprises SEQ ID NO: 7. In some embodiments, the anti-FSH antibody has a variable heavy chain region having at least 70%, at least 75%, at least 80%, at least 85%, at least 90%, at least 95%, or at least 99% identity with SEQ ID NO: 7. In some embodiments, SEQ ID NO: 7 has at least one conservative substitution. In some embodiments, the anti-FSH antibody has a variable light chain region. In some embodiments, the variable light chain region comprises SEQ ID NO: 8. In some embodiments, the anti-FSH antibody has a variable light chain region having at least 70%, at least 75%, at least 80%, at least 85%, at least 90%, at least 95%, or at least 99% identity with SEQ ID NO: 8. In some embodiments, SEQ ID NO: 8 has at least one conservative substitution.

In some embodiments, the anti-FSH antibody or antigen-binding portion thereof has one or more complementarity-determining regions (CDRs) of the variable heavy chain region comprising one or more of SEQ ID NO: 9, SEQ ID NO: 10, and SEQ ID NO: 11. In some embodiments, one or more of the CDRs of the variable heavy chain region has at least 70%, at least 75%, at least 80%, at least 85%, at least 90%, at least 95%, or at least 99% identity with one or more of SEQ ID NO: 9, SEQ ID NO: 10, and SEQ ID NO: 11. In some embodiments, one or more of SEQ ID NO: 9, SEQ ID NO: 10, and SEQ ID NO: 11 has at least one conservative substitution.

In some embodiments, the anti-FSH antibody or antigen-binding portion thereof has one or more complementarity-determining regions (CDRs) of the variable light chain region comprising one or more of SEQ ID NO: 12, SEQ ID NO: 13, and SEQ ID NO: 14. In some embodiments, one or more of the CDRs of the variable light chain region has at least 70%, at least 75%, at least 80%, at least 85%, at least 90%, at least 95%, or at least 99% identity with one or more of SEQ ID NO: 12, SEQ ID NO: 13, and SEQ ID NO: 14. In some embodiments, one or more of SEQ ID NO: 12, SEQ ID NO: 13, and SEQ ID NO: 14 has at least one conservative substitution.

In some embodiments, the anti-FSH antibody or antigen-binding portion thereof has a heavy chain variable region that comprises CDRH1, CDRH2, and CDRH3, wherein the CDRH1, CDRH2, and CDRH3 comprise the respective sequences of SEQ ID NO: 9, SEQ ID NO: 10, and SEQ ID NO: 11, or sequences consisting essentially of SEQ ID NO: 9, SEQ ID NO: 10, and SEQ ID NO: 11, but having at least one conservative substitution among one or more of SEQ ID NO: 9, SEQ ID NO: 19, and SEQ ID NO: 11. In some embodiments, the anti-FSH antibody or antigen-binding portion thereof has a light chain variable region that comprises CDRL1, CDRL2, and CDRL3, wherein the CDRL1, CDRL2 and CDRL3 comprise the respective sequences of SEQ ID NO: 12, SEQ ID NO: 13, and SEQ ID NO: 14, or sequences consisting essentially of SEQ ID NO: 12, SEQ ID NO: 13, and SEQ ID NO: 14, but having at least one conservative substitution among one or more of SEQ ID NO: 12, SEQ ID NO: 13, and SEQ ID NO: 14.

In some embodiments, the present disclosure comprises a nucleic acid sequence. In some embodiments, the nucleic acid sequences encode a heavy and/or light chain of an anti-FSH antibody or antigen-binding portion thereof. In some embodiments, the nucleic acids have one or more conservative substitutions. In some embodiments, the nucleic acids are codon optimized. In some embodiments, the nucleic acid sequence comprises SEQ ID NO: 3. In some embodiments, the nucleic acid has at least 70%, at least 75%, at least 80%, at least 85%, at least 90%, at least 95%, or at least 99% identity with SEQ ID NO: 3. In some embodiments, SEQ ID NO: 3 has at least one conservative substitution. In some embodiments, SEQ ID NO: 3 is codon optimized. In some embodiments, the nucleic acid sequence comprises SEQ ID NO: 4. In some embodiments, the nucleic acid has at least 70%, at least 75%, at least 80%, at least 85%, at least 90%, at least 95%, or at least 99% identity with SEQ ID NO: 4. In some embodiments, SEQ ID NO: 4 has at least one conservative substitution. In some embodiments, SEQ ID NO: 4 is codon optimized.

In some embodiments, the present disclosure comprises a vector or system of vectors containing one or more nucleic acid sequences encoding a heavy and/or light chain of an anti-FSH antibody or antigen-binding portion thereof of the present disclosure. In some embodiments, the vector or vector system comprises a nucleic acid sequence coding for a variable heavy chain region of an anti-FSH antibody or antigen-binding portion thereof of the present disclosure. In some embodiments, the vector or vector system comprises a nucleic acid sequence coding for a variable light chain region of an anti-FSH antibody or antigen-binding portion thereof of the present disclosure. In some embodiments, a nucleic acid sequence coding for a heavy chain is on the same vector as a nucleic acid sequence coding for a light chain. In some embodiments, a nucleic acid sequence coding for a variable heavy chain region is on a different vector than a nucleic acid sequence coding for a variable light chain region. In some embodiments, the vector or system of vectors is a plasmid or plasmids. In some embodiments, the vector or a system of vectors is a phage vector or vectors. In some embodiments, the phage vector is a γ phage. In some embodiments, the vector or vectors comprises a cosmid or cosmids. In some embodiments, the vector or system of vectors is a recombinant chromosome or recombinant chromosomes. In some embodiments, the vector system is a combination of different vectors. In some embodiments, expression of the different nucleic acid sequences may be concomitant. In other embodiments, expression of the different nucleic acid sequences may be separately inducible. In another embodiment, the present disclosure is directed to a vector or system of vectors containing one or more nucleic acid sequences encoding one or more complementarity determining regions (CDRs) of one or more heavy and/or light chains of an anti-FSH antibody or antigen-binding portions thereof of the present disclosure. In some embodiments, the present disclosure is directed to a cell transformed with a vector or vector system of the present disclosure. In some embodiments, the cell is a bacterial cell, a yeast cell, a plant cell, or a mammalian cell. In some embodiments, the mammalian cell is one of a Chinese hamster ovary (CHO) cell, including DUXB11, DG44 and CHOK1 lineages, a NSO murine myeloma cell, a PER.C6 cell, and a human embryonic kidney (HEK) cell, including HEK293 lineages.

In some embodiments, the present disclosure comprises a method of making a recombinant anti-FSH antibody or antigen-binding portion thereof. In some embodiments, the recombinant antibody is a chimeric antibody. In some embodiments, the recombinant antibody is a humanized antibody. In some embodiments, the method includes the steps of (i) transforming a host cell with at least one vector containing at least one nucleic acid sequence encoding at least one of 1) a heavy chain and a light chain of an anti-FSH antibody or antigen-binding portion thereof of the present disclosure or 2) at least one or more complementarity determining regions (CDRs) of one or more heavy and/or light chains of an anti-FSH antibody or antigen binding portion thereof of the present disclosure, (ii) expressing at least one nucleic acid sequence to create a recombinant anti-FSH antibody or antigen-binding portion thereof, and iii. recovering the recombinant antibody or antigen-binding portion thereof.

In some embodiments, the present disclosure is directed to a kit comprising one or more of the anti-FSH antibodies or antigen-binding portions thereof of the present disclosure.

In some embodiments, the present disclosure comprises a method of reducing adiposity in a subject in need thereof. In some embodiments, the method of reducing adiposity comprises a method of reducing white adipose tissue (WAT) in a subject in need thereof. In some embodiments, the method of reducing adiposity comprises a method of inducing thermogenic adipose tissue in a subject in need thereof. In some embodiments, the present disclosure comprises a method of reducing visceral adiposity. In some embodiments, the present disclosure comprises a method of treating obesity. In some embodiments, the present disclosure comprises a method of treating obesity-related disorders. In some embodiments, the obesity-related disorder is polycystic ovary syndrome (PCOS).

In some embodiments, the method comprises administering to said subject a therapeutically effective amount of a composition comprising an FSH inactivating agent. In some embodiments, the method comprises administering to said subject a therapeutically effective amount of a composition comprising an FSHR inactivating agent. In some embodiments, the FSH inactivating agent is a peptide. In some embodiments, the FSH inactivating agent is a nucleic acid. In some embodiments, the FSH inactivating agent is siRNA. In some embodiments, the FSH inactivating agent is a molecule. In some embodiments, the FSHR inactivating agent is a peptide. In some embodiments, the FSHR inactivating agent is a nucleic acid. In some embodiments, the FSHR inactivating agent is siRNA. In some embodiments, the FSHR inactivating agent is a molecule. In some embodiments, the FSHR inactivating agent is an antibody or an antigen-binding portion thereof. In some embodiments, the composition further comprises a pharmaceutically acceptable carrier or diluent.

In some embodiments, the anti-FSH antibody or antigen-binding portion thereof is a polyclonal antibody. In some embodiments, the anti-FSH antibody or antigen-binding portion thereof is a monoclonal antibody. In some embodiments, the anti-FSH antibody or antigen-binding portion thereof is a recombinant antibody. In some embodiments, the anti-FSH antibody or antigen-binding portion thereof comprises Hf2 or an antigen-binding portion thereof. In some embodiments, the anti-FSH antibody or antigen-binding portion thereof is an anti-FSH antibody or antigen-binding portion thereof of the present disclosure. In some embodiments, the anti-FSH antibody or antigen-binding portion thereof is a humanized antibody. In some embodiments, the anti-FSH antibody or antigen-binding portion thereof is a chimeric antibody. In some embodiments, the anti-FSH antibody or antigen-binding portion thereof is a human antibody. In some embodiments, the anti-FSH antibody or antigen-binding portion thereof is a single-chain variable fragment (scFv).

In some embodiments, the antibody or antigen-binding portion thereof specifically binds to FSH. In some embodiments, the antibody or antigen-binding portion thereof specifically binds to FSHR. In some embodiments, the antibody or antigen-binding portion thereof specifically binds to one or more epitopes within the β subunit of FSH. In some embodiments, the antibody or antigen-binding portion thereof specifically binds to one or more epitopes within SEQ ID NO: 1. In some embodiments, the antibody or antigen-binding portion thereof specifically binds to one or more epitopes within SEQ ID NO: 2. In some embodiments, SEQ ID NO: 1 has conservative substitutions. In some embodiments, SEQ ID NO: 2 has conservative substitutions. In some embodiments, the antibody or antigen-binding portion thereof comprises any anti-FSH antibody or antigen-binding portion thereof of the present invention. In some embodiments, the anti-FSH antibody or antigen-binding portion thereof comprises Hf2 or an antigen-binding portion thereof.

In some embodiments, the subject is a human subject. In some embodiments, the subject is a human female. In some embodiments, the subject is a human male. In some embodiments, the subject is a menopausal human female. In some embodiments, the subject is a premenopausal human female. In some embodiments, the subject is a perimenopausal human female.

In some embodiments, the present disclosure comprises a composition for use in the manufacture of a medicament for reducing adiposity in a human subject. In some embodiments, the medicament is for reducing white adipose tissue. In some embodiments, the medicament is for inducing thermogenic adipose tissue in a human subject. In some embodiments, the composition comprises an FSH inactivating agent according to any aspect of the present disclosure. In some embodiments, the composition comprises an FSHR inactivating agent according to any aspect of the present disclosure.

BRIEF DESCRIPTION OF THE FIGURES

FIGS. 1A, 1B, 1C and 1D show effects of ~9-week exposure to Hf2 or mouse IgG (200 µg per day per mouse, intraperitoneally), injected daily into 6-month-old male C57BL/6J mice pair-fed on high-fat diet (see Methods). FIG. 1A shows Food intake; FIG. 1B shows body weight; FIG. 1C shows fat mass, FM/TM and LM/TM (quantitative NMR); FIG. 1D shows TFV, SFV and VFV (micro-CT, coronal and transverse sections; (n=5 per group for FIGS. 1A, 1B, 1C, and 1D). FIG. 1E shows fluorescence and bright-field micrographs showing Ucp1 immunostaining in frozen sections of vWAT. DAPI: nuclear staining. Negative control: irrelevant IgG in place of first antibody in Hf2-treated mice. There was a marked increase in Ucp1 immunostaining with Hf2 treatment in vWAT, together with cell condensation, reminiscent of beiging. Two-tailed Student's t-test, **$P \leq 0.01$; mean±s.e.m. For body weight changes, see Source Data.

FIG. 2A represents recombinant mouse FSH (FSHα-FSHβ chimera, 2 µg) was passed through resin with immobilized polyclonal anti-FSH antibody or goat IgG. Elution (Eluate), flow-through (Flow), and consecutive wash fractions (Wash) were collected and immunoblotted, as shown, with the monoclonal anti-FSH antibody Hf2. FIG. 2B represents the linear sequence of the FSHα-FSHβ chimera (SEQ ID NO: 17). Peptides from the trypsinized eluate matched by mass spectrometry are marked in red, with the linker peptide shown as red solid circles. The polyclonal anti-FSH antibody was raised against LVYKDPARPNTQK (SEQ ID NO: 2). FIG. 2C represents the crystal structure of the human FSH-FSHR complex (PDB code 4AY9; FSHα not shown for clarity) indicates that the loop from the FSHβ subunit, containing the sequence LVYKDPARPKIQK (SEQ ID NO: 1), tucks into a small groove generated by the FSHR (i). Computational modelling of FSH bearing the peptide sequence LVYKDPARPNTQK (SEQ ID NO: 2) shows an identical binding mode (ii). Positively charged residues of the peptide surface complement the negatively charged residues of the FSHR binding site to generate strong electrostatic interactions at the binding surface (arrow) (iii). Given the small size of the groove (iv), binding of antibody to the peptide sequence will completely shield FSHβ from entering the FSHR binding pocket. FIG. 2D represents experimental confirmation that the anti-FSH antibody blocked FSH action using Thermo cells, which have a Luc2-T2A-tdTomato transgene inserted at the initiation codon of the Ucp1 gene10. Thermo cells retain BAT capacity and report Ucp1 activation using Luc2 as reporter. The effect of Fsh (30 ng ml$^{-1}$) and anti-FSH antibody (concentrations as noted) on Ucp1 expression was tested without fetal bovine serum (no endogenous FSH) with the Arb3 agonist CL-316,243 (10$^{-7}$ M). Notably, 1 µg ml$^{-1}$ anti-FSH antibody abolished the inhibitory effect of near-circulating levels of FSH on Ucp1 expression. Mean s.d.; *$P \leq 0.05$, **$P \leq 0.01$; in triplicate. FIG. 2E represents anti-FSH antibody measured as goat IgG in mouse serum (ELISA) following single injection of antibody (100 µg, intraperitoneally) yielded serum goat IgG (antibody) concentrations that were 10-20-fold higher than those required to inhibit FSH action in vitro (t1/2=25.6 h) n=3 per group (two-tailed Student's t-test, mean±s.e.m.).

FIG. 3A represents dual energy X-ray absorptiometry (DXA) (n=12 or 11 per group). FIGS. 3B and 3C represents tissue weight measurements for iWAT, gonadal WAT (gWAT) and BAT (n=9 or 10 per group). FIG. 3D represents effects of anti-FSH antibody on body fat under thermoneutral (30° C.) conditions. Three-month-old male mice were housed at 30° C., fed on a high-fat diet, and injected with antibody or IgG (200 µg per mouse per day, intraperitoneally) for 3 weeks for measurements of body weight and fat and lean mass (by qNMR) (n=3 or 4 per group). FIG. 3E represents plasma noradrenaline levels (HPLC) measured in samples from groups of 3-month-old female mice treated with antibody or goat IgG (200 µg per mouse per day, intraperitoneally) for 7 weeks, following which half the animals within the respective groups were killed, and the other half were treated with the tyrosine hydroxylase inhibitor α-methyl-p-tyrosine (AMPT, 250 mg kg$^{-1}$, injection repeated after 2 h with 125 mg kg$^{-1}$, intraperitoneally) (n=7 or 8 per group). Blood was drawn 2 h after the last AMPT injection. FIG. 3F represents plasma irisin levels (ELISA kit, Phoenix EK-067-29) measured following treatment of 3-month-old mice with antibody or goat IgG (200 μg per mouse per day, intraperitoneally, 5 and 7 per group for IgG and anti-FSH antibody, respectively). Serum meteorinlike (metrnl) was also measured (ELISA kit, R&D, DY7867); all samples were below assay detection. FIG. 3G represents measurement of GTT. FIG. 3H represents measurement of ITT. FIG. 3I represents hormone measurement. FIG. 3J represents lipid measurement. FIG. 3K represents E2 measurement. Two-tailed Student's t-test; * P≤0.05, **P≤0.01, ^P=0.0588, ^^P=0.065, or as shown; mean±s.e.m. FIG. 3L represents decomposition of TEE with p-Spline regression. Continuous time estimates of the RMR and AEE (PA) (shown as AEE) are shown for a typical calorimetry and activity dataset. The p-Spline regression model estimates the RMR from the correlation in time between the activity and energy expenditure data by minimizing the difference between the actual and predicted energy expenditure (AEE+RMR). By using a spline function instead of a constant intercept in the regression model, natural time variations that occur in the RMR can be determined and accurate estimates of the average RMR and AEE are obtained.

FIG. 4A represents food intake and body weight correlation. FIG. 4B represents fat mass, FM/TM and LM/TM measured by quantitative NMR (n=4 or 5 mice per group). FIG. 4C represents TFV, SFV and VFV measured by micro-CT (representative coronal and transverse sections from the same experiment; visceral, red; subcutaneous, yellow) (n=5 mice per group). Two-tailed Student's t-test; * P≤0.05, ** P≤0.01; mean±s.e.m.

FIG. 5A represents food intake and body weight. FIG. 5B represents fat mass, FM/TM, and LM/TM. FIG. 5C represents coronal and transverse sections; visceral, subcutaneous. Two-tailed Student's t-test; * P≤0.05, **P≤0.01; mean±s.e.m.

FIG. 6A represents total mass (TM), fat mass (FM), and FM/TM (quantitative NMR). FIG. 6B represents TFV, SFV and VFV (micro-CT, coronal and transverse sections). FIG. 6C represents Ucp1 immunostaining of sWAT sections showed smaller and densely staining beige-like cells in Fshr+/− mice and in antibody-treated wild-type mice. Two-tailed Student's t-test; * P≤0.05, **P≤0.01; mean±s.e.m.

FIG. 7A represents food intake and body weight (n=5 per group). FIG. 7B represents plasma FSH and oestrogen (E2) levels (plasma E2 mostly undetectable after ovariectomy) (n=4 or 5 per group). FIG. 7C represents anti-FSH antibody or IgG did not alter plasma glucose, total cholesterol, triglycerides or free fatty acids (n=4 or 5 mice per group). Two-tailed Student's t-test; **P≤0.01, or as shown.

FIG. 8A represents fat mass, FM/TM and LM/TM (n=5 or 9 mice per group, pooled), as measured by quantitative NMR. FIG. 8B represents TFV, VFV and SFV in mice fed ad libitum (transverse sections; pink, visceral; white, subcutaneous) (n=4 mice per group) measured by micro-CT. FIG. 8C represents Bone marrow adipose tissue (MAT; white) quantified as MAT/total volume (TV) at two voxels of interest (VOI1 and VOI2) (n=3 mice per group) measured by osmium micro-CT. Images in FIG. 8B and FIG. 8C are representative images from the respective experiments. Two-tailed Student's t-test; ^P=0.067, *P≤0.05, **P≤0.01; mean±s.e.m.

FIG. 10A represents total RNA was extracted from adipocytes derived from mesenchymal stem cells (MSC-ad) that were isolated from mouse ear lobes or 3T3.L1 cells and cultured in differentiation medium (MDI, containing IBMX, dexamethasone, and insulin). Total RNA was reverse transcribed and PCR performed using overlapping primer sets (bold lines) to amplify three large cDNA fragments. Overlapping regions covered by primers for Sanger sequencing are shown by arrows. The sequence of the Fshr in MSC-ad cells was identical to mouse ovarian Fshr (GenBank ID: NM_013523.3). The 3T3.L1 cell Fshr lacked exon 2 (red box) and displayed three amino acid variations (H158Y, F190L and K243E), but was fully functional in terms of its ability to reduce cAMP levels and Ucp1 expression in response to FSH. FIG. 10B represents that FSH also triggered upregulation of the lipogenic genes Fas and Lpl with a marginal increase in Pparg (** P Ü≤0.01, fold-change; qPCR, three biological replicates, in triplicate). The presence of a signalling-efficient FSHR in adipocytes is consistent with FSHR gene expression in human adipose tissue in GTex and GeneCard databases. It was likewise found that Fshr expression in WAT was lower than in the ovary: 1.00±0.47 versus 13.8±1.31 (fold-change, qPCR, P≤0.01, n=3 or 4 mice per group, measurements in triplicate). Two-tailed Student's t-test, mean±s.e.m.

FIG. 11A represents immunostaining with an anti-Fshr antibody of iWAT, vWAT and BAT sections (representative from 4 mice per group). FIG. 11B represents Cyclic AMP levels in differentiated 3T3.L1 cells (3 biological samples, in duplicate). PTX, pertussis toxin. FIG. 11C represents Luc2 activity in Thermo cells cultured in 10% (v/v) FBS (containing Fsh) (three biological replicates). FIG. 11D represents Luc2 radiance in nu/nu mice (fed on normal chow) injected with anti-FSH antibody or IgG (200 μg per day, intraperitoneal, 8 weeks) after implantation of $1.5 \times 10^6$ Thermo cells into both flanks (two mice were also transplanted into the upper trunk) (3 or 4 mice per group). Ctrl: two non-transgenic mice injected with d-luciferin. FIG. 11E represents tdTomato fluorescence in frozen sections of cell-implanted areas from the experiment in FIG. 11D. Two-tailed Student's t-test, *P≤0.05, **P≤0.01, ^P=0.0756; mean±s.e.m.

FIG. 12D represents relative expression of genes in BAT and WAT after 1 and 3 months (1M and 3M) of antibody or IgG treatment (normalized to housekeeping genes and to IgG) (3 or 6 biological replicates, in triplicate, by qPCR). Two-tailed Student's t-test; mean±s.e.m.; *P≤0.05, **P≤0.01.

FIG. 13A illustrates relative expression of genes (names noted) in BAT versus WAT (normalized to housekeeping genes and iWAT). FIG. 13B illustrates consistent with adipocyte beiging was enhanced brown gene expression (qPCR) in iWAT and BAT at 1 or 3 months (normalized to housekeeping genes and to IgG). Two-tailed Student's t-test; mean±s.e.m.; * P≤0.05 (qPCR, n=3 or 6 biological replicates, measured in triplicate).

FIG. 14C illustrates the construct used to generate the PhAM$^{excised}$ mouse (mito:Cox8 mito-chondria-localizing signal). Fluorescence captured in sWAT, vWAT and BAT after 2 weeks of antibody or IgG treatment. Representative images from experiment using three mice per group.

DETAILED DESCRIPTION

Figure 1:
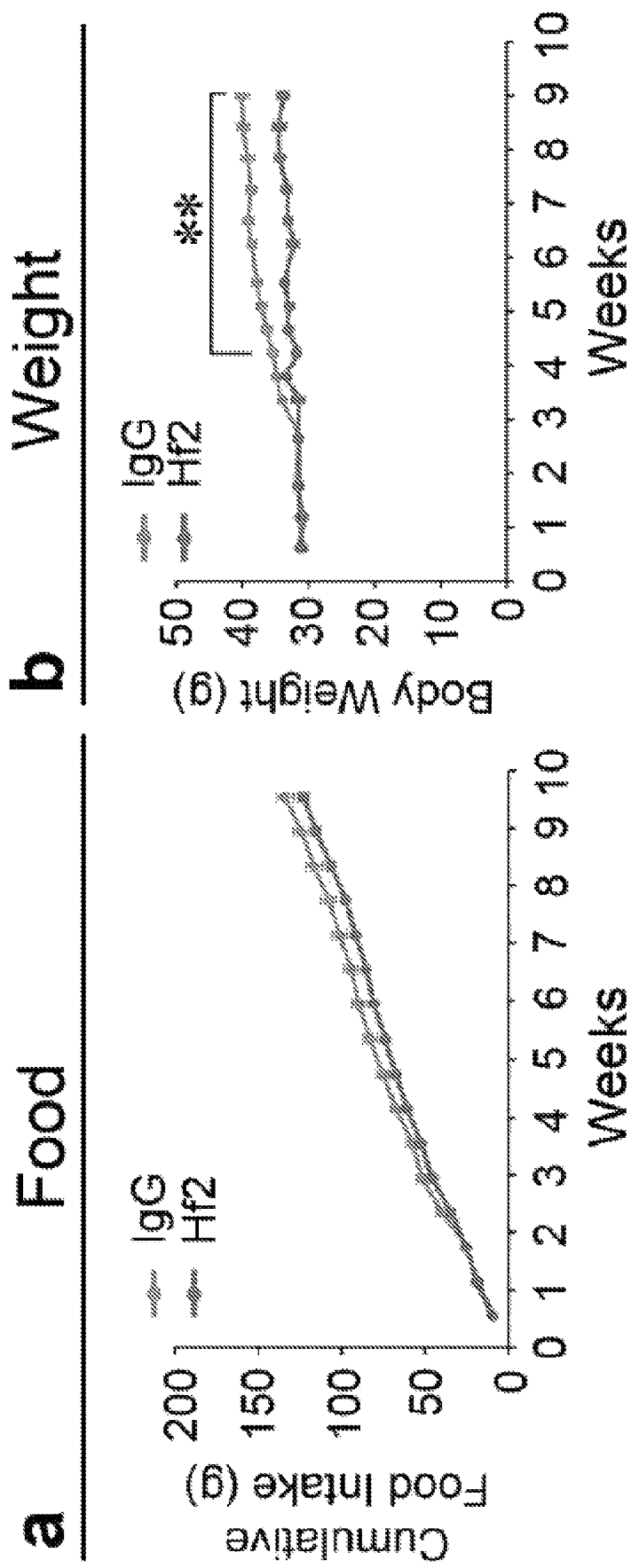
FIGS. 1A, 1B, 1C, 1D and 1E represent that the monoclonal anti-FSH antibody Hf2 (which was raised against a human FSHβ epitope, SEQ ID NO: 1), markedly reduces body weight and WAT and induces beiging in mice fed on a high-fat diet. The monoclonal antibody Hf2 was raised against a motif with the 13-amino-acid-long human FSHβ sequence LVYKDPARPKIQK (SEQ ID NO: 1) which corresponds to the mouse FSHβ sequence LVYKDPARPNTQK (SEQ ID NO: 2) against which the polyclonal antibody used in Example 2 was raised. Hf2 specifically binds human FSHβ in an ELISA. Sequence data of Hf2 is shown in Example 1.
Figure 1:
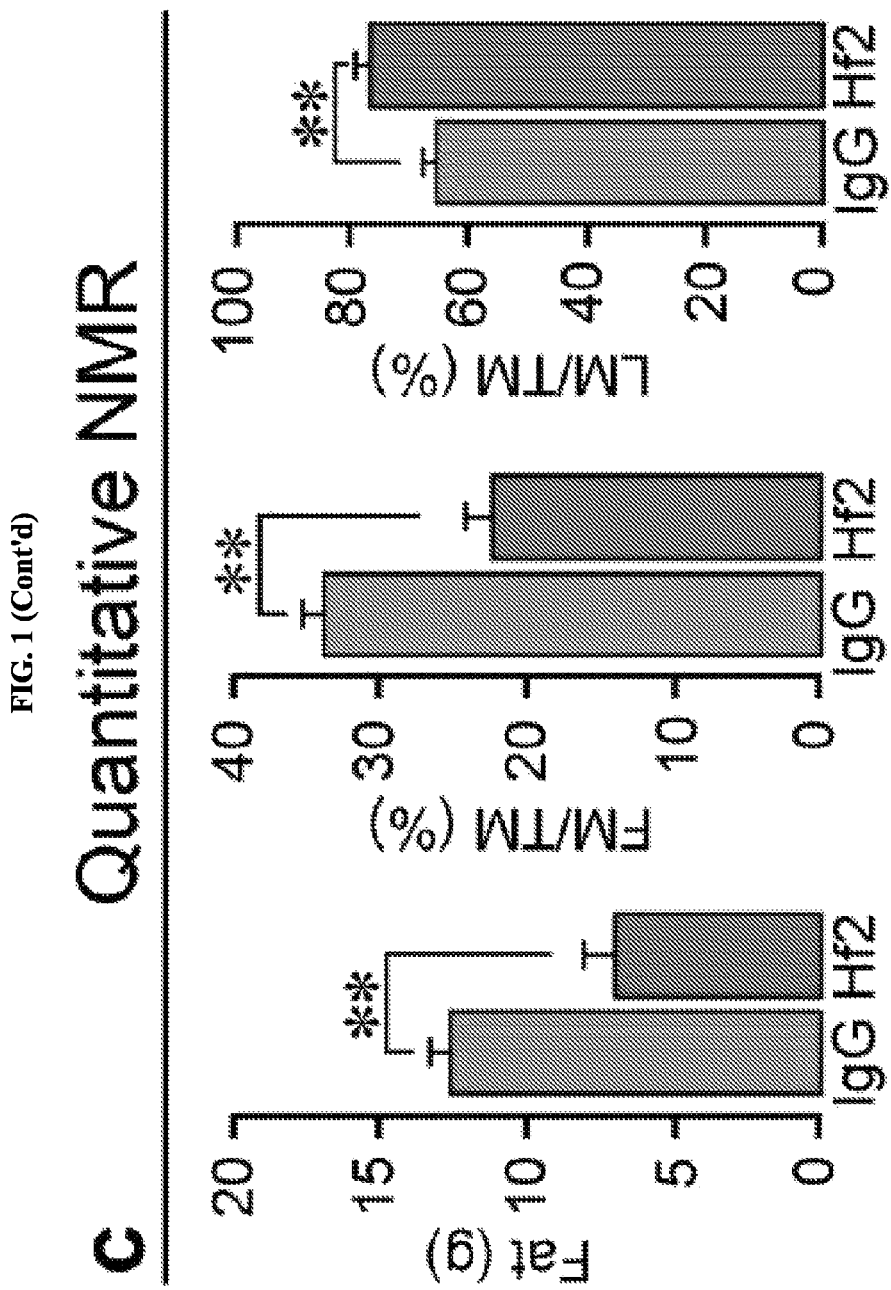
Figure 1:
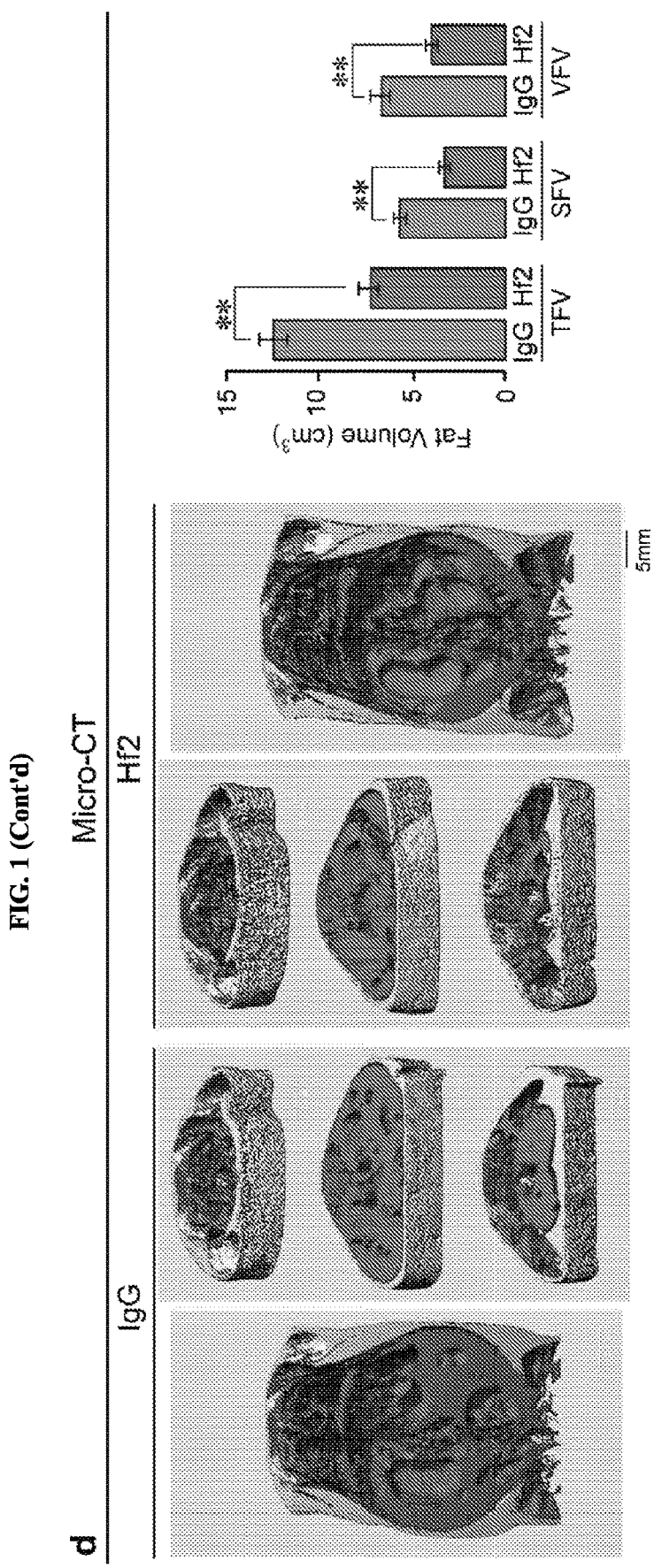
Figure 1:
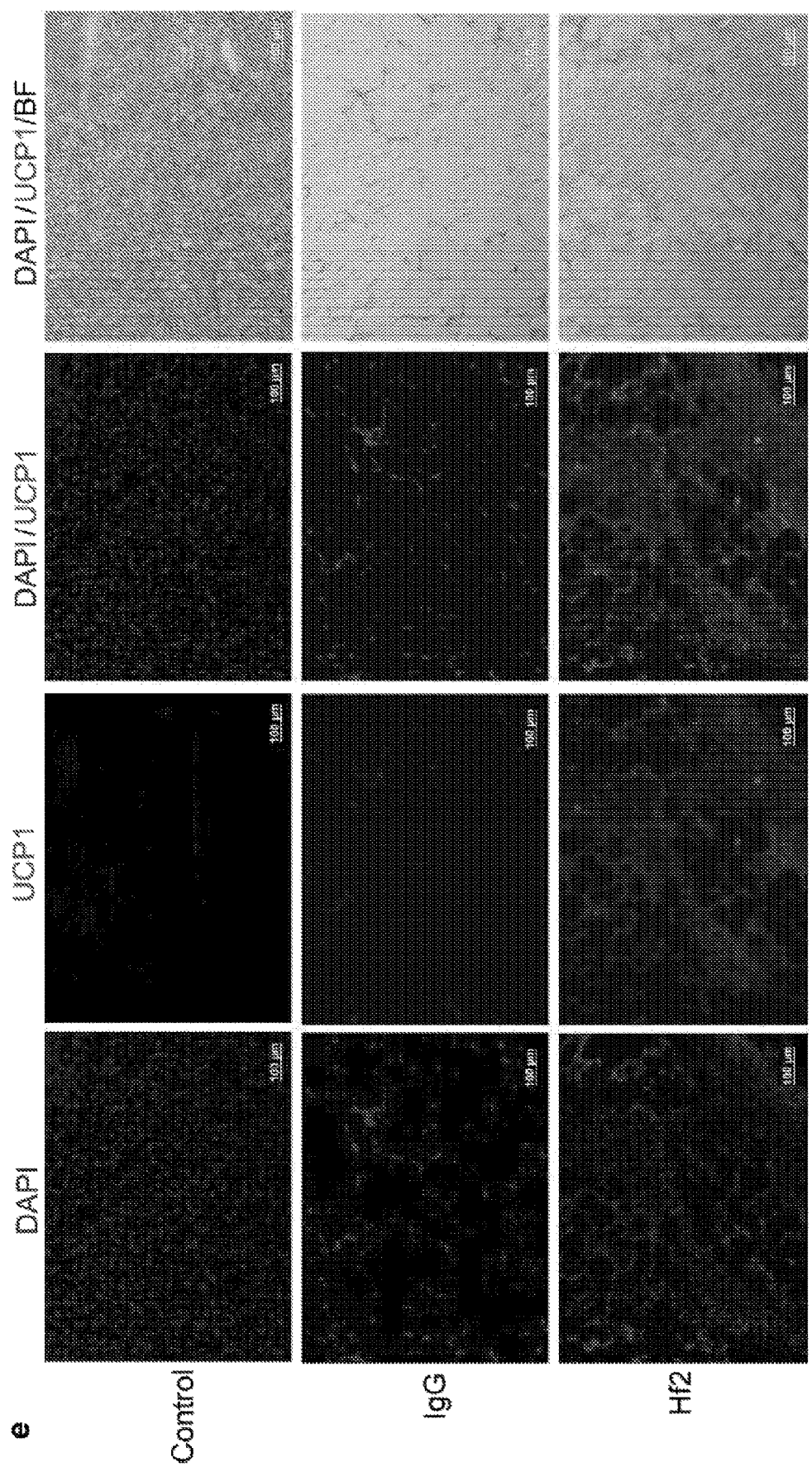

As used herein, the term "antibody" (Ab) is used in the broadest sense and specifically may include any immuno-globulin, whether natural or partly or wholly synthetically produced, including but not limited to monoclonal antibodies, polyclonal antibodies, multispecific antibodies (for example, bispecific antibodies and polyreactive antibodies), and antibody fragments. Thus, the term "antibody" as used in any context within this specification is meant to include, but not be limited to, any specific binding member, immunoglobulin class and/or isotype (e.g., IgG1, IgG2a, IgG2b, IgG3, IgG4, IgM, IgA1, IgA2, IgD, and IgE) and biologically relevant fragment or specific binding member thereof, including but not limited to Fab, F(ab')$_2$, scFv (single chain or related entity) and (scFv)$_2$.

As used herein, the term "antibody fragments" may include those antibody fragments obtained using techniques readily known and available to those of ordinary skill in the art, as reviewed herein. Therefore, in addition to the definition for "antibody" presented supra, the term "antibody" may further encompass any polypeptide or protein comprising a portion of an intact antibody, such as the antigen binding or variable region of the intact antibody. These can be derived from natural sources, or they may be partly or wholly synthetically produced. Examples of antibody fragments include, but are not limited to, Fab, Fab', F(ab')$_2$, and Fv fragments; diabodies; and linear antibodies.

The terms "specific binding," "selective binding," "selectively binds," and "specifically binds," may refer to antibody binding to an epitope on a predetermined antigen but not to other antigens. Typically, the antibody binds with an equilibrium dissociation constant ($K_D$) of approximately less than $10^{-6}$ M, such as approximately less than $10^{-7}$ M, $10^{-8}$ M, $10^{-9}$ M or $10^{-10}$ M or even lower when determined by, e.g., equilibrium dialysis or surface plasmon resonance (SPR) technology in a BIACORE® 2000 surface plasmon resonance instrument using the predetermined antigen, e.g., an epitope on FSH and/or FSHR, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen.

As used herein, the term "epitope" may refer to the region of an antigen to which an antibody or T cell binds, e.g. a region within the beta (β) subunit of FSH, including but not limited to an epitope within SEQ ID NO: 1 and/or SEQ ID NO: 2. An "antigen" refers to a substance that elicits an immunological reaction or binds to the products of that reaction.

As used herein, the terms "follicle stimulating hormone" and/or "FSH" may refer to a gonadotropin, a type of glycoprotein polypeptide hormone. FSH is synthesized and secreted by the gonadotropic cells of the anterior pituitary gland and is implicated in regulating the development, growth, maturation, and reproductive processes of the body. FSH is a 35.5 kDa glycoprotein heterodimer, having two polypeptide units, an alpha (α) and beta (β) subunit. FSH is similar in structure to luteinizing hormone (LH), thyroid-stimulating hormone (TSH), and human chorionic gonadotropin (hCG), sharing an identical alpha (α) subunit, but having variations in the beta (β) subunit. This makes the beta (β) subunit an attractive therapeutic target for FSH inhibitors as the inhibitors targeting the beta (β) subunit, e.g. one or more epitopes located within the beta (β) subunit, can be specific to inhibiting FSH. An exemplary gene encoding the beta (β) subunit of human FSH may be accessed at, e.g., Accession No. NM_000510. An exemplary gene encoding the beta (β) subunit of murine FSH may be accessed at, e.g., NM_008045. One of ordinary skill in the art will be able to reach predicted amino acid sequences from the provided nucleotide sequences.

As used herein, the terms "follicle stimulating hormone receptor" and/or "FSHR" may refer to a transmembrane receptor that interacts with FSH. FSHR is a G protein-coupled receptor (GPCR). Activation of FSHR is necessary for the hormonal functioning of FSH. The beta (β) subunit of FSH is necessary for binding to FSHR, and thus the beta (β) subunit confers upon FSH its specific biological action. Therefore, because the biological activity of FSH relies upon binding to FSHR, inhibiting the biological activity of FSH may be achieved either by directly inactivating FSH, e.g. by binding to the beta (β) subunit of FSH, or by directly inactivating FSHR. This is because inactivating FSHR will result in a loss of biological activity similar to that of inactivating FSH as the biological activity relies on binding between FSH and FSHR. An exemplary gene encoding human FSHR may be accessed at, e.g., Accession No. XM_011532734 (transcript variant X2) or XM_011532733 (transcript variant X1). An exemplary gene encoding FSHR may be accessed at, e.g., Accession No. NM_013523.3. One of ordinary skill in the art will be able to reach predicted amino acid sequences from the provided nucleotide sequences.

As used herein, the term "FSH inactivating agent" is defined as an agent that reduces the bioactivity or bioavailability of FSH. The FSH inactivating agent may achieve the reduction by binding directly or indirectly to FSH, such as in the case of anti-FSH antibodies or similar peptides or molecules, or the agent may prevent release of FSH from the anterior pituitary gland. In the case of siRNAs, FSH inactivating agents may prevent translation of mRNA encoding FSH. As used herein, the term "FSHR inactivating agent" is defined as an agent that reduces or prevents downstream signaling by the FSHR. The FSHR inactivating agent may achieve the reduction or prevention by blocking the receptor and preventing FSH from binding to FSHR, e.g. by binding directly or indirectly to FSHR, such as in the case of anti-FSHR antibodies or similar peptides or molecules, or the agent may allow FSH to bind to FSHR but otherwise blocks downstream signaling. In the case of siRNAs, FSHR inactivating agents may prevent translation of mRNA encoding FSHR.

As used herein, the term "carriers" may include pharmaceutically acceptable carriers, excipients, or stabilizers that are nontoxic to the cell or mammal being exposed thereto at the dosages and concentrations employed. Often the pharmaceutically acceptable carrier is an aqueous pH buffered solution. Examples of physiologically acceptable carriers include, but not limited to, buffers such as phosphate, citrate, and other organic acids; antioxidants including, but not limited to, ascorbic acid; low molecular weight (less than about 10 residues) polypeptide; proteins, such as, but not limited to, serum albumin, gelatin, or immunoglobulins; hydrophilic polymers such as, but not limited to, polyvinylpyrrolidone; amino acids such as, but not limited to, glycine, glutamine, asparagine, arginine or lysine; monosaccharides, disaccharides, and other carbohydrates including, but not limited to, glucose, mannose, or dextrins; chelating agents such as, but not limited to, EDTA; sugar alcohols such as, but not limited to, mannitol or sorbitol; salt-forming counterions such as, but not limited to, sodium; and/or nonionic surfactants such as, but not limited to, TWEEN; polyethylene glycol (PEG), and PLURONICS. Any combination of such components, including probable inclusion of a bacteriostat, may be useful to fill the formulations of the present disclosure.

As used herein, the term "treating" or "treatment" of a disease may refer to executing a protocol, which may include administering one or more drugs to a patient (human or otherwise), in an effort to alleviate signs or symptoms of the disease. Thus, in the case of treating adiposity, including visceral and/or central adiposity, "treating" or "treatment" may arise in a situation where a course of treatment is advanced to reduce adiposity in a patient as measured by e.g. a reduction in total or gross white adipose tissue and/or an increase in thermogenic beige adipose tissue. Alleviation can occur prior to signs or symptoms of the disease appearing as well as after their appearance. Thus, "treating" or "treatment" includes "preventing" or "prevention" of disease. The terms "prevent" or "preventing" refer to prophylactic and/or preventative measures, wherein the object is to prevent or slow down the targeted pathologic condition or disorder. For example, in the case of preventing adiposity, including visceral and/or central adiposity, "preventing" or "preventing" may arise in a situation where a course of treatment is advanced in order to prevent or stall increase in adiposity as measured by e.g. a reduction or slowdown in buildup of white adipose tissue. In addition, "treating" or "treatment" does not require complete alleviation of signs or symptoms, does not require a cure, and specifically includes protocols that may have only a marginal effect on the patient.

The term "homology" as used herein may refer to the existence of shared structure between two compositions. The term "homology" in the context of proteins may refer to the amount (e.g. expressed in a percentage) of overlap between two or more amino acid and/or peptide sequences. In the context of nucleic acids, the term may refer to the amount (e.g. expressed in a percentage) of overlap between two or more nucleic acid sequences. As used herein, the percent (%) homology between two sequences is equivalent to the percent identity between the two sequences. The percent identity between the two sequences is a function of the number of identical positions shared by the sequences (i.e., % homology=# of identical positions/total # of positions ×100), taking into account the number of gaps, and the length of each gap, which need to be introduced for optimal alignment of the two sequences. The comparison of sequences and determination of percent identity between two sequences can be accomplished using a mathematical algorithm. Such homology is well-represented in the art via local alignment tools and/or algorithms, and may include pairwise alignment, multiple sequence alignment methods, structural alignment methods, and/or phylogenetic analysis methods. Where sequences differ in conservative substitutions, the percent sequence identity may be, but not necessarily is, adjusted upwards to correct for the conservative nature of the substitution. Means for making this adjustment are well known to those of skill in the art. Typically, but not necessarily, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1.

The terms "co-administration," "co-administered," and "in combination with" as used herein may refer to the administration of at least two agents or therapies to a subject. In some embodiments, the co-administration of two or more agents/therapies is concurrent. In other embodiments, a first agent/therapy is administered prior to a second agent/ therapy. Those of skill in the art understand that the formulations and/or routes of administration of the various agents/therapies used may vary.

The terms "conservative sequence modifications" or "conservative substitutions" as used herein may refer to amino acid modifications to a target epitope or antibodies and antigen-binding portions thereof of the disclosure that does not significantly affect or alter the binding characteristics of the anti-FSH antibodies, for example but not necessarily Hf2 and antigen-binding portions thereof, or anti-FSHR antibodies to the epitope(s), including but not limited to SEQ ID NO: 1 and SEQ ID NO: 2. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a target epitope that the anti-FSH or anti-FSHR antibodies of the disclosure specifically bind to, e.g. epitopes on the beta (β) subunit of FSH for some anti-FSH antibodies, can be replaced with other amino acid residues from the same side chain family and the antibodies of the present disclosure can be tested against the target epitope can be tested, for example using functional assays described herein or otherwise known in the art. Likewise, one or more amino acid residues within the CDR regions of an antibody of the invention, e.g. Hf2, can be replaced with other amino acid residues from the same side chain family and the altered antibody can be tested for retained function using the functional assays described herein.

As used herein, the term "patient" may refer to a biological system to which a treatment can be administered. A biological system can include, for example, an individual cell, a set of cells (e.g., a cell culture), an organ, a tissue, or a multi-cellular organism. A "patient" can refer to a human patient or a non-human patient. In some embodiments, the term "patient" means a female patient. In some embodiments, the term "patient" means a male patient. In some embodiments, the term "patient" means a menopausal female patient. In some embodiments, the term "patient" means a premenopausal female patient. In some embodiments, the term "patient" means a perimenopausal female patient.

As used herein, the terms "purified" or "isolated" antibody, peptide, polypeptide, or protein may refer to a peptide, polypeptide, or protein, that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide/protein (e.g., anti-FSH or anti-FSHR antibodies) described in the disclosure can be produced by recombinant DNA techniques.

The present disclosure provides for agents that are capable of binding to and/or inactivating or inhibiting follicle stimulating hormone (FSH) and/or the follicle stimulating hormone receptor (FSHR). In some embodiments, the present disclosure provides for a method of reducing adiposity in a subject in need thereof comprising administering a therapeutically effective amount of a FSH inhibiting agent and/or an FSHR inhibiting agent. In some embodiments reduction of adiposity occurs by reduction in visceral body fat. In some embodiments, the reduction of adiposity occurs by reduction in white adipose tissue (WAT). In some embodiments, the reduction in adiposity occurs by an increase in thermogenic adipose tissue.

One exemplary type of inhibiting agent is anti-FSH and anti-FSHR antibodies, for example Hf2 and antigen-binding portions thereof, discussed in greater detail herein. However, the disclosure is explicitly not limited as such. FSH/FSHR inhibiting agents may include small molecules, proteins, peptides, nucleic acids, antibodies and the like. Nucleic acids encoding FSH and the FSH receptor are known. Thus, antisense molecules directed to either or both find use in the disclosure. Similarly, siRNA directed to FSHR finds use in the disclosure to reduce the level of FSH receptor on adipocytes thereby reducing adiposity. In addition, Arey et al. have described a novel synthetic molecule capable of inhibiting the action of FSH. This compound (7-[4-[Bis-(2-carbamoyl-ethyl-amino]-6-chloro-(1,3,5)-triazin-2-ylamino)-4-hydroxy-3-(4-methoxy-phenylazo)-naphthalene]-2-sulfonic acid, sodium salt) is a selective, noncompetitive inhibitor of the FSHR and is described in more detail Arey et al (*Endocrinology*, 2002 October; 143 (10):3822-9. In addition, U.S. Pat. No. 6,426,357 describes a class of small molecule thiazolidinone FSH receptor antagonists. In addition, such agents may be delivered by a fusion construct to a bisphosphonate or like compound to target it to bone or to TAT, a short peptide for intracellular delivery (2001 July; 24(3):247-56; Methods Enzymol. 2001; 332:36-49. In addition U.S. Pat. No. 6,583,179 describes a series of novel substituted aminoalkylamide derivatives that are antagonists of FSH.

In exemplary embodiments, the present disclosure provides for anti-FSH and anti-FHSR antibodies and antigen-binding fragments thereof. An anti-FSH or anti-FSHR antibody may take one of numerous forms in the art, as disclosed herein. Antibodies are in part defined by the antigens to which they bind, thus, an "anti-FSH antibody" is any such antibody which specifically binds at least one epitope found on FSH, and an "anti-FSHR antibody" is any such antibody which specifically binds at least one epitope found on FSHR. In some embodiments, the epitope is located in the beta (β) subunit of FSH. In some embodiments, the epitope is located within LVYKDPARPKIQK (SEQ ID NO: 1). In some embodiments, the epitope is located within LVYKDPARPNTQK (SEQ ID NO: 2). It is understood in the art that an antibody is a glycoprotein comprising at least two heavy (H) chains and two light (L) chains inter-connected by disulfide bonds, or an antigen binding portion thereof. A heavy chain comprises a heavy chain variable region (VH) and a heavy chain constant region (CH1, CH2 and CH3). A light chain comprises a light chain variable region (VL) and a light chain constant region (CL). The variable regions of both the heavy and light chains comprise framework regions (FWR) and complementarity determining regions (CDR). The four FWR regions are relatively conserved while CDR regions (CDR1, CDR2 and CDR3) represent hypervariable regions and are arranged from $NH_2$ terminus to the COOH terminus as follows: FWR1, CDR1, FWR2, CDR2, FWR3, CDR3, FWR4. The variable regions of the heavy and light chains contain a binding domain that interacts with an antigen while, depending of the isotype, the constant region(s) may mediate the binding of the immunoglobulin to host tissues or factors. It is known in the art that it is possible to manipulate monoclonal and other antibodies and use techniques of recombinant DNA technology to produce other antibodies or chimeric molecules which retain the specificity of the original antibody. Such techniques may evolve introducing DNA encoding the immunoglobulin variable region, or CDRs, of an antibody to the constant regions, or constant regions plus framework regions, of a different immunoglobulin.

An exemplary anti-FSH antibody or antigen-binding portion thereof of the present disclosure comprises Hf2 or antigen-binding portion thereof, characterized in Example 1 infra. Hf2 has a variable heavy chain region comprising SEQ ID NO: 7 and a variable light chain region comprising SEQ ID NO: 8. Hf2 has a CDRH1 comprising SEQ ID NO: 9, a CDRH2 comprising SEQ ID NO: 10, a CDRH3 comprising SEQ ID NO: 11, a CDRL1 comprising SEQ ID NO: 12, a CDRL2 comprising SEQ ID NO: 13, and a CDRL3 comprising SEQ ID NO: 14. However, the anti-FSH antibodies or antigen-binding portions thereof of the present disclosure are not limited as such. For example, in some embodiments, the anti-FSH antibody has a variable heavy chain region having at least 70%, at least 75%, at least 80%, at least 85%, at least 90%, at least 95%, or at least 99% identity with SEQ ID NO: 7. In some embodiments, SEQ ID NO: 7 has at least one conservative substitution. In some embodiments, the anti-FSH antibody has a variable light chain region having at least 70%, at least 75%, at least 80%, at least 85%, at least 90%, at least 95%, or at least 99% identity with SEQ ID NO: 8. In some embodiments, SEQ ID NO: 8 has at least one conservative substitution. In some embodiments, one or more of the CDRs of the variable heavy chain region has at least 70%, at least 75%, at least 80%, at least 85%, at least 90%, at least 95%, or at least 99% identity with one or more of SEQ ID NO: 9, SEQ ID NO: 10, and SEQ ID NO: 11. In some embodiments, one or more of SEQ ID NO: 9, SEQ ID NO: 10, and SEQ ID NO: 11 has at least one conservative substitution. In some embodiments, one or more of the CDRs of the variable light chain region has at least 70%, at least 75%, at least 80%, at least 85%, at least 90%, at least 95%, or at least 99% identity with one or more of SEQ ID NO: 12, SEQ ID NO: 13, and SEQ ID NO: 14. In some embodiments, one or more of SEQ ID NO: 12, SEQ ID NO: 13, and SEQ ID NO: 14 has at least one conservative substitution.

The antibodies of the disclosure may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the FSH or FSHR polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the FSH or FSHR polypeptide or a fusion protein thereof. The immunizing agent may comprise an antigenic fragment of the beta (β) subunit of FSH. The immunizing agent may be a peptide sequence comprising SEQ ID NO:1 or SEQ ID NO: 2 or a peptide sequence consisting essentially of SEQ ID NO:1 or SEQ ID NO:2 but having conservative substitutions. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing c ells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63]. The culture medium in which the hybridoma cells are cultured can then be assayed for the presence of monoclonal antibodies directed against FSH or FSHR. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, Anal. Biochem., 107:220 (1980).

After the desired hybridoma cells are identified, the clones may be subcloned by limiting dilution procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the disclosure can be readily isolated and sequenced using conventional procedures (e.g., by using oligonucleotide probes that are capable of binding specifically to genes encoding the heavy and light chains of murine antibodies). The hybridoma cells of the disclosure serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, as in U.S. Pat. No. 4,816,567, or by covalently joining to the immunoglobulin coding sequence all or part of the coding sequence for a non-immunoglobulin polypeptide. Such a non-immunoglobulin polypeptide can be substituted for the constant domains of an antibody of the disclosure, or can be substituted for the variable domains of one antigen-combining site of an antibody of the disclosure to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The antibodies of the disclosure may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Techniques for humanization of murine antibodies are known to one of ordinary skill in the art and are generally reviewed in Safdari et al., (2013) Biotechnol. Genet. Eng. Rev., 29: 175-86, hereby incorporated by reference in its entirety. Humanization of antibodies generally comprises grafting of CDRs (for example, but not necessarily, one or more of SEQ ID NO: 9, SEQ ID NO: 10, SEQ ID NO: 11, SEQ ID NO: 12, SEQ ID NO: 13 and/or SEQ ID NO: 14, or one or more conservative substituted variants thereof, into an appropriate human variable region framework, for example, as disclosed in Jones et al. (1986) Nature 321, 522-525, hereby incorporated by reference in its entirety. Common methods used include, but are not limited to, framework-homology-based humanization, germline humanization, complementary determining regions (CDR)-homology-based humanization and specificity determining residues (SDR) grafting. Proper orientation of the CDRs in the humanized antibody is typically necessary and can be determined by, for example, evaluating the crystal structure of the humanized antibody. The principal advantage of humanized antibodies comes from significantly reduced immunogenicity when compared to a murine monoclonal antibody, particularly the constant domain (Fc region) of a murine antibody, although humanizing the variable domains also leads to reduced immunogenicity. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications:

Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, Intern. Rev. Immunol. 13 65-93 (1995).

Some embodiments of the invention are directed to vectors and vector systems containing nucleotide sequences that code for the variable regions of anti-FSH antibodies or antigen-binding portions thereof of the present disclosure, e.g. Hf2 or antigen-binding portions thereof, as well as cells transformed with such vectors and/or vector systems. The vector may be, for example but not necessarily, a plasmid; other explicitly non-limiting recombinant vectors are known in the art and may include, e.g. phage vectors such as a λ phage vector, other viral vectors such as non-replicating adenoviral vector, lentiviral vector, pSV, pCMV series of plasmid vectors, vaccinia and retroviral vectors, baculoviral vectors, cosmids, artificial chromosomes. The vector may be a mammalian expression vectors; for example, vectors may be transfected into mammalian cells and the DNA may be integrated into the genome by homologous recombination in the case of stable transfection, or alternatively the cells may be transiently transfected. Common to most engineered vectors are origin of replications, multicloning sites, and selectable markers, so as long as a vector (including systems of vectors, e.g. multiple plasmids) contain such a system they are considered to be covered by the scope of this invention. Common promoters for mammalian expression vectors include CMV and SV40 promoters; nonviral promoters such as EF-1 promoters are also known.

A vector or vector system that codes for one or both variable region(s) of Hf2 may contain one of or both of SEQ ID NO: 3 and SEQ ID NO: 4 or a nucleotide sequence or sequences that shares or share a degree of identity with SEQ ID NO: 3 and/or SEQ ID NO: 4, e.g. at least 70%, at least 75%, at least 80%, at least 85% at least 90%, at least 95%, or more than 95% identity with either or both of SEQ ID NO: 3 and SEQ ID NO: 4. Independent of such identity, SEQ ID NO: 3 and/or SEQ ID NO: 4 may have conservative substitutions and/or may be codon optimized and such would be considered to be within the scope of this invention. As discussed herein, the nucleotide sequences coding for the variable regions may or may not be on the same vector and expression of such may or may not be separately inducible.

Some embodiments of the present disclosure are directed to methods of making a recombinant anti-FSH antibody, e.g. a chimeric anti-FSH antibody or a humanized anti-FSH antibody or antigen-binding portion thereof. In the case of a chimeric antibody, a host cell (e.g. a yeast cell or an *E. coli* cell) is transfected (e.g. by a phage) by a vector, including those discussed supra, containing genes coding for the variable heavy/light regions of one or more anti-HCMV antibodies, e.g. SEQ ID NO: 3 and/or SEQ ID NO:4 in the case of Hf2 or antigen-binding portions thereof. In the case of humanized antibodies, the host cell may be transfected by a vector or system of vectors that contains nucleotides coding for CDRs of the variable heavy/light regions of Hf2, e.g. nucleotide sequence or sequence coding for one or more of SEQ ID NO: 9, SEQ ID NO: 10, SEQ ID NO: 11, SEQ ID NO: 12, SEQ ID NO: 13, and/or SEQ ID NO: 14. These nucleotides coding for CDRs may have conservative substitutions and, independent of such conservative substitutions, may share a certain degree of identity (i.e. at least 70%, at least 75%, at least 80%, at least 85%, at least 90%, at least 95%, or more than 95% identity) with the nucleotide sequences coding for one or more of SEQ ID NO: 9, SEQ ID NO: 10, SEQ ID NO: 11, SEQ ID NO: 12, SEQ ID NO: 13, and/or SEQ ID NO: 14. Additionally, one or more of these nucleotide sequences may or may not be codon optimized. With either chimeric or humanized antibodies, the Fc region will remain human. The transformed host cell will then be induced to produce the recombinant antibodies, which may assemble the antibodies from heavy/light chains in the host cell and then transport the antibodies out of the cell, or the antibodies may self-assemble outside the host cell and be exported as heavy/light chains. Common host cells may include yeast cells, e.g. *S. cerevisiae, S. pombe* and *P. pastoris*, bacteria, e.g. *E. coli*, and mammalian cells, e.g. Chinese hamster ovary (CHO) cells, including DUXB11, DG44 and CHOK1 lineages, NSO murine myeloma cells, PER.C6 human cells, and human embryonic kidney (HEK) cells, e.g. HEK293. Other less common host cells, but still included within the scope of the invention, include plant cells, for example, those based on the Ti plasmid of *Agrobacterium tumefaciens*. Cell-free expression systems also exist, for example, based on *E. coli* cell lysate, containing cellular components necessary for transcription/translation. Eukaryotic and mammalian cell-free systems are also known in the art, for example wheat germ cell-free expression system, and those described in Brodel et al. (2015), *Methods Mol Bio.* 1261: 129-40, hereby incorporated by reference in its entirety. Some recombinant antibody production systems express the recombinant antibodies on the surface of the host cell before harvesting, others simply release the antibodies into a medium for collection. Such variations are intended to be within the scope of the present disclosure.

The compositions of the present disclosure, either alone or in combination, may be used in vitro, ex vivo, and in vivo depending on the particular application. In accordance, the present disclosure provides for administering a pharmaceutical composition comprising a pharmaceutically acceptable carrier and a pharmacologically effective amount of one or more of the subject peptides, or suitable salts thereof. The pharmaceutical composition may be formulated as powders, granules, solutions, suspensions, aerosols, solids, pills, tablets, capsules, gels, topical cremes, suppositories, transdermal patches, etc.

Pharmaceutically acceptable salts are intended to include any art recognized pharmaceutically acceptable salts including organic and inorganic acids and/or bases. Examples of salts include sodium, potassium, lithium, ammonium, calcium, as well as primary, secondary, and tertiary amines, esters of lower hydrocarbons, such as methyl, ethyl, and propyl. Other salts may include organic acids, such as acetic acid, propionic acid, pyruvic acid, maleic acid, succinic acid, tartaric acid, citric acid, benzoic acid, cinnamic acid, salicylic acid, etc.

The pharmaceutically acceptable composition may be in liquid form or solid form. A solid formulation is generally, but not necessarily, lyophilized and brought into solution prior to administration for either single or multiple dosing. The formulations should not be exposed to extreme temperature or pH so as to avoid thermal denaturation. Thus, it may be important to formulate a composition of the present disclosure within a biologically relevant pH range. A solution buffered to maintain a proper pH range during storage is often necessary, especially for liquid formulations stored for longer periods of time between formulation and administration. Typically, both liquid and solid formulations require storage at lower temperatures (usually, but not necessarily, between 2-8° C.) in order to retain stability for longer periods. Formulated compositions, especially liquid formulations, may contain a bacteriostat to prevent or minimize proteolysis during storage, including but not limited to effective concentrations (usually <1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component.

Additional components may be added to either a buffered liquid or solid formulation, including but not limited to sugars as a cryoprotectant (including but not necessarily limited to polyhydroxy hydrocarbons such as sorbitol, mannitol, glycerol and dulcitol and/or disaccharides such as sucrose, lactose, maltose or trehalose) and, in some instances, a relevant salt (including but not limited to NaCl, KCl or LiCl). Such formulations, especially liquid formulations slated for long term storage, will rely on a useful range of total osmolarity to both promote long term stability at temperature of, e.g. 2-8° C., or higher, while also making the formulation useful for parenteral injection. For example, but not necessarily, an effective range of total osmolarity (the total number of molecules in solution) may be from about 200 mOs/L to about 800 mOs/L. It will be apparent that the amount of a cyroprotectant, such as sucrose or sorbitol, may depend upon the amount of salt in the formulation in order for the total osmolarity of the solution to remain within an appropriate range. Therefore a salt free formulation may, but not necessarily, contain from about 5% to about 25% sucrose.

Alternatively, a salt free sorbitol-based formulation may, but not necessarily, contain sorbitol within a range from about 3% to about 12%. Salt-free formulations may warrant increased ranges of the respective cryoprotectant in order to maintain effective osmolarity levels. These formulation may also contain a divalent cation (including but not necessarily limited to $MgCl_2$, $CaCl_2$ and $MnCl_2$); and a non-32 ionic surfactant (including but not necessarily limited to Polysorbate-80 (Tween 80®), Polysorbate-60 (Tween 60®), Polysorbate-40 (Tween 40®) and Polysorbate-20 (Tween 20®), polyoxyethylene alkyl ethers, including but not limited to Brij 58®, Brij 35®, as well as others such as Triton X-100®, Triton X 114®, NP406, Span 85 and the Pluronic series of non-ionic surfactants (e.g., Pluronic 121)). Any combination of such components, including probable inclusion of a bacteriostat, may be useful to fill the antibody-containing formulations of the present disclosure. The compositions of the present disclosure may also be a "chemical derivative", which describes compositions that contain additional chemical moieties which are not normally a part of the original compound (e.g., pegylation). Such moieties may improve the solubility, half-life, absorption, etc. of the base FSH/FSHR inactivating agents. Alternatively the moieties may attenuate undesirable side effects of the base molecule or decrease the toxicity of the base FSH/FSHR inactivating agents.

Suitable formulations may be found in, among others, Remington's Pharmaceutical Sciences, 17*th* edition, Mack Publishing Co., Philadelphia, Pa., 1985 and Handbook of Pharmaceutical Excipients, 3rd Ed, Kibbe, A. H. ed., Washington D.C., American Pharmaceutical Association, 2000; hereby incorporated by reference in their entirety. The pharmaceutical compositions described herein can be made in a manner well known to those skilled in the art (e.g., by means conventional in the art, including mixing, dissolving, granulating, levigating, emulsifying, encapsulating, entrapping or lyophilizing processes).

Additionally, the FSH/FSHR inactivating agents may also be introduced or encapsulated into the lumen of liposomes for delivery and for extending life time of the peptide formulations ex vivo or in vivo. As known in the art, liposomes can be categorized into various types: multilamellar (MLV), stable plurilamellar (SPLV), small unilamellar (SUV) or large unilamellar (LUV) vesicles. Liposomes can be prepared from various lipid compounds, which may be synthetic or naturally occurring, including phosphatidyl ethers and esters, such as phosphotidylserine, phosphotidylcholine, phosphatidyl ethanolamine, phosphatidylinositol, dimyristoylphosphatidylcholine; steroids such as cholesterol; cerebrosides; sphingomyelin; glycerolipids; and other lipids (see for example, U.S. Pat. No. 5,833,948).

Cationic lipids are also suitable for forming liposomes. Generally, the cationic lipids have a net positive charge and have a lipophilic portion, such as a sterol or an acyl or diacyl side chain. Preferably, the head group is positively charged. Typical cationic lipids include 1,2-dioleyloxy-3-(trimethylamino)propane; N-[1-(2,3,-ditetradecyclyoxy)propyl]-N,N-dimethyl-N-N-hydroxyethylammonium bromide; N-[1-(2,3-dioleyloxy)propyl]-N,N-dimethyl-N-hydroxy ethylammonium bromide; N-[1-(2,3-dioleyloxy)propyl]-N,N,N-trimethylammonium chloride; 3-[N-(N',N'-dimethylaminoethane)carbamoyl]cholesterol; and dimethyldioctadecylammonium. Of particular interest are fusogenic liposomes, which are characterized by their ability to fuse with a cell membrane upon appropriate change in physiological condition or by presence of fusogenic component, particularly a fusogenic peptide or protein. In one aspect, the fusogenic liposomes are pH and temperature sensitive in that fusion with a cell membrane is affected by change in temperature and/or pH (see for example, U.S. Pat. Nos. 4,789,633 and 4,873,089). Generally, pH sensitive liposomes are acid sensitive. Thus, fusion is enhanced in physiological environments where the pH is mildly acidic, for example the environment of a lysosome, endosome and inflammatory tissues. This property allows direct release of the liposome contents into the intracellular environment following endocytosis of liposomes (see Mizoue, T. Int. *J. Pharm.* 237: 129-137 (2002)).

Another form of fusogenic liposomes comprises liposomes that contain a fusion enhancing agent. That is, when incorporated into the liposome or attached to the lipids, the agents enhance fusion of the liposome with other cellular membranes, thus resulting in delivery of the liposome contents into the cell. The agents may be fusion enhancing peptides or proteins, including hemagglutinin HA2 of influenza virus (Schoen, P. *Gene Ther.* 6: 823-832 (1999)); Sendai virus envelope glycoproteins (Mizuguchi, H. *Biochem. Biophys. Res. Commun.* 218: 402-407 (1996)); vesicular stomatitis virus envelope glycoproteins (VSV-G) glycoprotein (Abe, A. et al. J Virol 72: 6159-63 (1998)); peptide segments or mimics of fusion enhancing proteins; and synthetic fusion enhancing peptides (Kono, K. et al. Biochim. Biophys. Acta. 1164: 81-90 (1993); Pecheur, E. I. *Biochemistry* 37: 2361-71 (1998); U.S. Pat. No. 6,372,720).

Liposomes also include vesicles derivatized with a hydrophilic polymer, as provided in U.S. Pat. Nos. 5,013,556 and 5,395,619, hereby incorporated by reference, (see also, Kono, K. et al. *J. Controlled Release* 68: 225-35 (2000); Zalipsky, S. et al. *Bioconjug. Chem.* 6: 705-708 (1995)) to extend the circulation lifetime in vivo. Hydrophilic polymers for coating or derivation of the liposomes include polyethylene glycol, polyvinylpyrrolidone, polyvinylmethyl ether, polyaspartamide, hydroxymethyl cellulose, hydroxyethyl cellulose, and the like. In addition, as described above, attaching proteins that bind a cell surface protein which is endocytosed, e.g., capsid proteins or fragments thereof tropic for a particular cell types and antibodies for cell surface proteins which undergo internalization, may be used for targeting and/or facilitating uptake of the liposomes to specific cells or tissues.

Liposomes are prepared by ways well known in the art (see for example, Szoka, F. et al. *Ann. Rev. Biophys. Bioeng.* 9: 467-508 (1980)). One typical method is the lipid film hydration technique in which lipid components are mixed in an organic solvent followed by evaporation of the solvent to generate a lipid film. Hydration of the film in aqueous buffer solution, preferably containing the subject peptide or nucleic acid, results in an emulsion, which is sonicated or extruded to reduce the size and polydispersity. Other methods include reverse-phase evaporation (see Pidgeon, C. et al. *Biochemistry* 26: 17-29 (1987); Duzgunes, N. et al. *Biochem. Biophys. Acta.* 732: 289-99 (1983)), freezing and thawing of phospholipid mixtures, and ether infusion.

In another preferred embodiment, the carriers are in the form of microparticles, microcapsules, microspheres and nanoparticles, which may be biodegradable or non-biodegradable (see for example, *Microencapsulates: Methods and Industrial Applications, Drugs and Pharmaceutical Sciences, Vol* 73, Benita, S. ed, Marcel Dekker Inc., New York, 1996). The substance may be within the core of the particle or attached to the particle's polymer network.

Generally, the difference between microparticles (or microcapsules or microspheres) and nanoparticles may be one of size.

A variety of materials are useful for making microparticles. Non-biodegradable microcapsules and microparticles include, but are not limited to, those made of polysulfones, poly(acrylonitrile-co-vinyl chloride), ethylene-vinyl acetate, and hydroxyethylmethacrylate-methyl-methacrylate copolymers. These are useful for implantation purposes where the encapsulated FSH/FSHR inactivating agent diffuses out from the capsules. In another aspect, the microcapsules and microparticles are based on biodegradable polymers, preferably those that display low toxicity and are well tolerated by the immune system. These include protein based microcapsulates and microparticles made from fibrin, casein, serum albumin, collagen, gelatin, lecithin, chitosan, alginate or poly-amino acids such as poly-lysine. Biodegradable synthetic polymers for encapsulating may comprise polymers such as polylactide (PLA), polyglycolide (PGA), poly (lactide-co-glycolide) (PLGA), poly(caprolactone), polydioxanone trimethylene carbonate, polyhydroxyalkonates (e.g., poly((3-hydroxybutyrate)), poly(β-ethyl glutamate), poly(DTH iminocarbony (bisphenol A iminocarbonate), poly (ortho ester), and polycyanoacrylate. Various methods for making microparticles containing the subject compositions are well known in the art, including solvent removal process (see for example, U.S. Pat. No. 4,389,330); emulsification and evaporation (Maysinger, D. et al. *Exp. Neuro.* 141: 47-56 (1996); Jeffrey, H. et al. *Pharm. Res.* 10: 362-68 (1993)), spray drying, and extrusion methods.

Another type of carrier is nanoparticles, which are generally suitable for intravenous administrations. Submicron and nanoparticles are generally made from amphiphilic diblock, triblock, or multiblock copolymers as is known in the art. Polymers useful in forming nanoparticles include, but are not limited to, poly(lactic acid) (PLA; see Zambaux et al., *J. Control Release* 60: 179-188 (1999)), poly(lactide-co-glycolide), blends of poly(lactide-co-glycolide) and polycarprolactone, diblock polymer poly(l-leucine-block-l-glutamate), diblock and triblock poly(lactic acid) (PLA) and poly(ethylene oxide) (PEO) (see De Jaeghere, F. et al., *Pharm. Dev. Technol.;* 5: 473-83 (2000)), acrylates, arylamides, polystyrene, and the like. As described for microparticles, nanoparticles may be non-biodegradable or biodegradable. Nanoparticles may be also be made from poly (alkylcyanoacrylate), for example poly(butylcyanoacrylate), in which the FSH/FSHR inactivating agent is absorbed onto the nanoparticles and coated with surfactants (e.g., polysorbate 80). Methods for making nanoparticles are similar to those for making microparticles and may include, among others, emulsion polymerization in continuous aqueous phase, emulsification-evaporation, solvent displacement, and emulsification-diffusion techniques (see Kreuter, J. "Nano-particle Preparation and Applications, In Microcapsules and nanoparticles in medicine and pharmacy," (M. Donbrow, ed.), pg. 125-148, CRC Press, Boca Rotan, Fla., 1991).

Hydrogels are also useful in delivering the FSH/FSHR inactivating agents into a host. Generally, hydrogels are cross linked, hydrophilic polymer networks permeable to a wide variety of drug compounds, including peptides. Hydrogels have the advantage of selective trigger of polymer swelling, which results in controlled release of the entrapped drug compound. Depending on the composition of the polymer network, swelling and subsequent release may be triggered by a variety of stimuli, including pH, ionic strength, thermal, electrical, ultrasound, and enzyme activities. Non-limiting examples of polymers useful in hydrogel compositions include, among others, those formed from polymers of poly(lactide-co-glycolide), poly(N-isopropylacrylamide); poly(methacrylic acid-g-polyethylene glycol); polyacrylic acid and poly(oxypropylene-co-oxyethylene) glycol; and natural compounds such as chrondroitan sulfate, chitosan, gelatin, or mixtures of synthetic and natural polymers, for example chitosan-poly(ethylene oxide).

The gel polymers may be acrylic acid polymers, preferably carbomers (e.g., carboxypolymethylene), such as Carbopol (e.g. Carbopol 420-430, 475, 488, 493, 910, 934P, 974P, and the like; Brock et al., Pharmacotherapy 14: 430-437 (1994)), which are non-linear polymers of acrylic acid cross linked with polyalkenyl polyether. Other types of carbomers include acrylic acids cross linked with polyfunctional compounds, such as polyallysucrose. In addition to the advantage of hydrating and swelling to a gel, which entraps the subject compounds and limits their release, carbomer gels are mucoadhesive.

For the purposes of this disclosure, the method of administration is chosen depending on the condition being treated, the form of the subject compositions, and the pharmaceutical composition. Administration of the FSH/FSHR inactivators can be done in a variety of ways, including, but not limited to, cutaneously, subcutaneously, intravenously, orally, topically, transdermally, intraperitoneally, intramuscularly, nasally, and rectally (e.g., colonic administration). For example, microparticle, microsphere, and microencapsulate formulations are useful for oral, intramuscular, or subcutaneous administrations. Liposomes and nanoparticles are additionally suitable for intravenous administrations. Administration of the pharmaceutical compositions may be through a single route or concurrently by several routes. For instance, oral administration can be accompanied by rectal or topical administration to the affected area. Alternatively, oral administration is used in conjunction with intravenous or parenteral injections.

The delivery systems also include sustained release or long term delivery methods, which are well known to those skilled in the art. By "sustained release" or "long term release" as used herein is meant that the delivery system administers a pharmaceutically therapeutic amount of subject compounds for more than a day, preferably more than a week, and most preferable at least about 30 days to 60 days, or longer. Long term release systems may comprise implantable solids or gels containing the subject peptide, such as biodegradable polymers described above; pumps, including peristaltic pumps and fluorocarbon propellant pumps; osmotic and mini-osmotic pumps; and the like. Peristaltic pumps deliver a set amount of drug with each activation of the pump, and the reservoir can be refilled, preferably percutaneously through a port. A controller sets the dosage and can also provide a readout on dosage delivered, dosage remaining, and frequency of delivery. Fluorocarbon propellant pumps utilize a fluorocarbon liquid to operate the pump. The fluorocarbon liquid exerts a vapor pressure above atmospheric pressure and compresses a chamber containing the drug to release the drug. Osmotic pumps (and mini-osmotic pumps) utilize osmotic pressure to release the drug at a constant rate. The drug is contained in an impermeable diaphragm, which is surrounded by the osmotic agent. A semipermeable membrane contains the osmotic agent, and the entire pump is housed in a casing. Diffusion of water through the semipermeable membrane squeezes the diaphragm holding the drug, forcing the drug into bloodstream, organ, or tissue. These and other such implants are particularly useful in treating a disease condition, especially those manifesting recurring episodes or which are progressive in nature, by delivering the FSH/FSHR inactivating agents of the disclosure via systemic (e.g., intravenous or subcutaneous) or localized doses (e.g., intracerebroventricular) in a sustained, long term manner.

In one preferred embodiment, the method of administration is by oral delivery, in the form of a powder, tablet, pill, or capsule. Pharmaceutical formulations for oral administration may be made by combining one or more peptide with suitable excipients, such as sugars (e.g., lactose, sucrose, mannitol, or sorbitol), cellulose (e.g., starch, methyl cellulose, hydroxylmethyl cellulose, carboxymethyl cellulose, etc.), gelatin, glycine, saccharin, magnesium carbonate, calcium carbonate, polymers such as polyethylene glycol or polyvinylpyrrolidone, and the like. The pills, tablets, or capsules may have an enteric coating, which remains intact in the stomach but dissolves in the intestine. Various enteric coating are known in the art, a number of which are commercially available, including, but not limited to, methacrylic acid-methacrylic acid ester copolymers, polymer cellulose ether, cellulose acetate phthalate, polyvinyl acetate phthalate, hydroxypropyl methyl cellulose phthalate, and the like. Alternatively, oral formulations of the compositions are in prepared in a suitable diluent. Suitable diluents include various liquid form (e.g., syrups, slurries, suspensions, etc.) in aqueous diluents such as water, saline, phosphate buffered saline, aqueous ethanol, solutions of sugars (e.g. sucrose, mannitol, or sorbitol), glycerol, aqueous suspensions of gelatin, methyl cellulose, hydroxylmethyl cellulose, cyclodextrins, and the like. As used herein, diluent or aqueous solutions also include infant formula. In some embodiments, lipohilic solvents are used, including oils, for instance vegetable oils, peanut oil, sesame oil, olive oil, corn oil, safflower oil, soybean oil, etc.); fatty acid esters, such as oleates, triglycerides, etc.; cholesterol derivatives, including cholesterol oleate, cholesterol linoleate, cholesterol myristilate, etc.; liposomes; and the like.

In one embodiment, administration is done rectally. This may use formulations suitable for topical application in the form of salves, tinctures, cremes, or for application into the lumen of the intestine by use of compositions in the form of suppositories, enemas, foams, etc. Suppositories may contain conventional suppository bases such as cocoa butter, carbowaxes, polyethylene glycols, or glycerides, which are solid or semi-solid at room temperature but liquid at body temperature.

In yet another preferred embodiment, the administration is carried out cutaneously, subcutaneously, intraperitoneally, intramuscularly or intravenously. As discussed above, these are in the form of peptides dissolved or suspended in suitable aqueous medium, as discussed above. Additionally, the pharmaceutical compositions for injection may be prepared in lipophilic solvents, which include, but is not limited to, oils, such as vegetable oils, olive oil, peanut oil, palm oil soybean oil, safflower oil, etc.; synthetic fatty acid esters, such as ethyl oleate or triglycerides; cholesterol derivatives, including cholesterol oleate, cholesterol linoleate, cholesterol myristilate, etc.; or liposomes, as described above. The compositions may be prepared directly in the lipophilic solvent or preferably, as oil/water emulsions, (see for example, Liu, F. et al. *Pharm. Res.* 12: 1060-1064 (1995); Prankerd, R. J. J. *Parent. Sci. Tech.* 44: 139-49 (1990); U.S. Pat. No. 5,651,991).

The dose and dosage regimen depends upon a variety of factors readily determined by a physician, such as the nature of the infection, for example, its therapeutic index, the patient, and the patient's history. Generally, a therapeutically effective amount of a composition is administered to a patient. In some embodiments, the amount of composition administered is in the range of about 0.001 mg/kg to about 1000 mg/kg of patient body weight, and any range in between. Depending on the severity of condition, about 0.1 mg/kg to about 50 mg/kg body weight (for example, about 0.1-15 mg/kg/dose, more usually from about 1-25 mg/kg body weight) of composition is an initial candidate dosage for administration to the patient, whether, for example, by one or more separate administrations, or by continuous infusion. The compositions may be delivered relatively low volume rates, for example but not necessarily from about 0.001 ml/day to 10 ml/day so as to minimize tissue disturbance or trauma near the site where the formulation is released. The formulation may be released at a rate of, depending on the specific biological agent(s), at a low dose, e.g., from about 0.01 µg/hr or 0.1 µg/hr, 0.25 µg/hr, 1 µg/hr, generally up to about 200 µg/hr, or the formulation is delivered at a low volume rate e.g., a volume rate of from about 0.001 ml/day to about 1 ml/day, for example, 0.01 micrograms per day up to about 20 milligrams per day. Dosage depends on a number of factors such as potency, bioavailability, and toxicity of the active ingredient and the requirements of the subject. The progress of this therapy is readily monitored by conventional methods and assays and based on criteria known to the physician or other persons of skill in the art. The above parameters for assessing successful treatment and improvement in the disease are readily measurable by routine procedures familiar to a physician.

The delivery systems also include sustained release or long term delivery methods, which are well known to those skilled in the art. By "sustained release or" "long term release" as used herein is meant that the delivery system administers a pharmaceutically therapeutic amount of subject compounds for more than a day, preferably more than a week, and most preferable at least about 30 days to 60 days, or longer. Long term release systems may comprise implantable solids or gels containing the subject peptide, such as biodegradable polymers described above; pumps, including peristaltic pumps and fluorocarbon propellant pumps; osmotic and mini-osmotic pumps; and the like. Peristaltic pumps deliver a set amount of drug with each activation of the pump, and the reservoir can be refilled, preferably percutaneously through a port. A controller sets the dosage and can also provide a readout on dosage delivered, dosage remaining, and frequency of delivery. Fluorocarbon propellant pumps utilize a fluorocarbon liquid to operate the pump. The fluorocarbon liquid exerts a vapor pressure above atmospheric pressure and compresses a chamber containing the drug to release the drug. Osmotic pumps (and mini-osmotic pumps) utilize osmotic pressure to release the drug at a constant rate. The drug is contained in an impermeable diaphragm, which is surrounded by the osmotic agent. A semipermeable membrane contains the osmotic agent, and the entire pump is housed in a casing. Diffusion of water through the semipermeable membrane squeezes the diaphragm holding the drug, forcing the drug into bloodstream, organ, or tissue. These and other such implants are particularly useful in treating an inflammatory disease condition, especially those manifesting recurring episodes or which are progressive in nature, by delivering the FSH/FSHR inactivators of the disclosure via systemic (e.g., intravenous or subcutaneous) or localized doses in a sustained, long term manner.

The present disclosure also encompasses the therapeutic combinations disclosed herein in the form of a kit or packaged formulation. A kit or packaged formulation as used herein includes one or more dosages of a subject peptide, and salts thereof, in a container holding the dosages together with instructions for simultaneous or sequential administration to a patient. For example, the package may contain the peptides along with a pharmaceutical carrier combined in the form of a powder for mixing in an aqueous solution, which can be ingested by the afflicted subject. The package or kit includes appropriate instructions, which encompasses diagrams, recordings (e.g., audio, video, compact disc), and computer programs providing directions for use of the combination therapy. The foregoing descriptions of specific embodiments of the present disclosure have been presented for purposes of illustration and description. They are not intended to be exhaustive or to limit the disclosure to the precise forms disclosed, and obviously many modifications and variations are possible in light of the above teaching.

Where a value of ranges is provided, it is understood that each intervening value, to the tenth of the unit of the lower limit unless the context clearly dictates otherwise, between the upper and lower limit of that range and any other stated or intervening value in that stated range is encompassed within the disclosure. The upper and lower limits of these smaller ranges which may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference in their entireties.

As used herein and in the appended claims, the singular forms "a", "and" and "the" include plural references unless the context clearly dictates otherwise The term "about" refers to a range of values which would not be considered by a person of ordinary skill in the art as substantially different from the baseline values. For example, the term "about" may refer to a value that is within 20%, 15%, 10%, 9%, 8%, 7%, 6%, 5%, 4%, 3%, 2%, 1%, 0.5%, 0.1%, 0.05%, or 0.01% of the stated value, as well as values intervening such stated values, for which context will define.

Publications disclosed herein are provided solely for their disclosure prior to the filing date of the present disclosure. Nothing herein is to be construed as an admission that the present disclosure is not entitled to antedate such publication. Further, the dates of publication provided may be different from the actual publication dates which may need to be independently confirmed.

Each of the applications and patents cited in this text, as well as each document or reference, patent or non-patent literature, cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

The following non-limiting examples serve to further illustrate the present disclosure.

EXAMPLES

1. Characterization of the Monoclonal anti-FSH Antibody Hf2 and Antigen Binding Portions Thereof Total RNA was isolated from hybridoma cells following the technical manual of TRIzol® Reagent (Ambion, Cat. No.: 15596-026). Total RNA was then reverse transcribed into cDNA using isotype-specific anti-sense primers or universal primers following the technical manual of PrimeScript™ 1st Strand cDNA Synthesis Kit (Takara, Cat. No. 6110A). The antibody fragments of VH and VL were amplified according to the standard operating procedure (SOP) of rapid amplification of cDNA ends (RACE) of GenScript. Amplified antibody fragments were cloned into a standard cloning vector separately. Colony PCR was performed to screen for clones with inserts of correct sizes. No less than five colonies with inserts of correct sizes were sequenced for each fragment. The sequences of different clones were aligned and the consensus sequence of these clones was provided. Results are shown in TABLES 1, 2, 3, and 4 below.

TABLE 1

Nucleotide sequences encoding variable heavy/light chains of Hf2. Underlined sections represent leader sequences.

| DNA Sequence | Antibody Region |
|---|---|
| ATGAGAGTGCTGATTCTTTTGCGGCTGTTCACAGCCTTTCC<br>TGGTATCCTGTCTGATGTGCATCTTCAGGAGTCGGGACCTG<br>GCCTGGTGAAACCTTCTCAGTCTCTGTCCCTCACCTGCACT<br>GTCACTGGCTTCTCAATCACCAGTGATTATGCCTGGAACTG<br>GATCCGGCAGTTTCCAGGAAACAAACTGGAGTGGATGGGCT<br>CCATATTTTCCAGTGGTAGCATTAACTACAACCCATCTCTC<br>AAAAGTCGAATCTCTATCACTCGAGACACATCCAGGAACCA<br>GTTCTTCCTGCAGTTGAATTCTGTGACTACTGCGGACGCAG<br>GCACATATTACTGTGCAAGAGGGGTACTGGGACCGACTAC<br>TGGGGCCAAGGCACCACTCTCACAGTCTCCTCA<br>(SEQ ID NO: 3) | Hf2 Variable Heavy (V$_H$) Chain |
| ATGATGTCCTCTGCTCAGTTCCTTGGTCTCCTGTTGCTCTG<br>TTTTCAAGGTTCCAGATGTGATATCCAGATGACACAGACTA<br>CATCCTCCCTGTCTGCCTCTCTGGGAGACAGAGTCACCATC<br>AGTTGCAGGGCAAGTCAGGACATTAGCAATTATTTAAGCTG<br>GTATCAGCAGAAACCAGATGGAACTATTAAACTCCTGATCT<br>ACTACACATCACGATTACATTCAGGAGTCTCGTCAAGGTTC<br>AGTGGCAGTGGGTCTGGAACAGATTATTCTCTCACCATTAG<br>CAACCTGGAGCAAGAAGATTTTGCCACTTACTTTTGCCAAC<br>AGGGTCATACGCTTCCTCCCACGTTCGGAGGGGGGACCAAG<br>CTGGAAATAAAA<br>(SEQ ID NO: 4) | Hf2 Variable Light (Kappa) (V$_L$) Chain |

TABLE 2

Amino acid sequences of variable heavy/light chains of Hf2. Underlined sections represent leader sequences. Double underlined sections represent complementarity-determining regions (CDRs).

| Amino Acid Sequence | Antibody Region |
|---|---|
| MRVLILLRLFTAFPGILSDVHLQESGPGLVKpSQSLSLTCT<br>VTGFSITSDYAWNWIRQFPGNKLEWMGSIFSSGSINYNPSL<br>KSRISITRDTSRNQFFLQLNSVTTADAGTYYCARGGTGTDY<br>WGQGTTLTVSS<br>(SEQ ID NO: 5) | Hf2 Variable Heavy (V$_H$) Chain (including leader sequence) |
| MMSSAQFLGLLLLCFQGSRCDIQMTQTTSSLSASLGDRVTI<br>SCRASQDISNYLSWYQQKPDGTIKLLIYYTSRLHSGVSSRF<br>SGSGSGTDYSLTISNLEQEDFATYFCQQGHTLPPTFGGGTK<br>LEIK<br>(SEQ ID NO: 6) | Hf2 Variable Light (Kappa) (V$_L$) Chain (including leader sequence) |
| DVHLQESGPGLVKPSQSLSLTCTVTGFSITSDYAWNWIRQF<br>PGNKLEWMGSIFSSGSINYNPSLKSRISITRDTSRNQFFLQ<br>LNSVTTADAGTYYCARGGTGTDYWGQGTTLTVSS<br>(SEQ ID NO: 7) | Hf2 Variable Heavy (V$_H$) Chain |
| DIQMTQTTSSLSASLGDRVTISCRASQDISNYLSWYQQKPD<br>GTIKLLIYYTSRLHSGVSSRFSGSGSGTDYSLTISNLEQED<br>FATYFCQQGHTLPPTFGGGTKLEIK<br>(SEQ ID NO: 8) | Hf2 Variable Light (Kappa) (V$_L$) Chain |

TABLE 3

Complementarity-Determining Regions (CDRs) of Hf2.

| Amino Acid Sequence | Antibody Region |
|---|---|
| SDYAWN<br>(SEQ ID NO: 9) | Hf2 Heavy Chain CDR1 (CDRH1) |
| SIFSSGSINYNPSLKS<br>(SEQ ID NO: 10) | Hf2 Heavy Chain CDR2 (CDRH2) |
| GGTGTDY<br>(SEQ ID NO: 11) | Hf2 Heavy Chain CDR3 (CDRH3) |
| RASQDISNYLS<br>(SEQ ID NO: 12) | Hf2 Light Chain CDR1 (CDRL1) |
| YTSRLHS<br>(SEQ ID NO: 13) | Hf2 Light Chain CDR2 (CDRL2) |

TABLE 3-continued

Complementarity-Determining Regions (CDRs) of Hf2.

| Amino Acid Sequence | Antibody Region |
|---|---|
| QQGHTLPPT (SEQ ID NO: 14) | Hf2 Light Chain CDR3 (CDRL3) |

TABLE 4

IMGT Analysis of V(D)J Junctions of Hf2.

| Sequence | V-GENE and allele | Functionality | V-Region Identity % (nt) | J-gene and allele | D-gene and allele | AA junction | Junction Frame |
|---|---|---|---|---|---|---|---|
| $V_H$ | Musmus IGHV3-2*02 F | Productive | 95.49% (275/288 nt) | Musmus IGHJ2*01 F(a) | Musmus IGHD4-1*01 F | CARGGTGTDYV (SEQ ID NO: 15) | In-frame |
| $V_L$ | Musmus IGKV10-96*01 F | Productive | 97.13% (271/279 nt) | Musmus IGKJ2*01 F | — | CQQGHTLPPTF (SEQ ID NO: 16) | In-frame |

In view of the evidence put forth in Example 2 infra that polyclonal anti-FSH antibody induces WAT beiging and reduced adiposity, a monoclonal antibody, Hf2, was raised to the human FSHβ epitope, LVYKDPARPKIQK, (SEQ ID NO: 1). SEQ ID NO: 1 differs by two amino acids from the mouse epitope (SEQ ID NO: 2). It was found that Hf2 binds both human and mouse FSHβ, and its injection into mice on a high-fat diet phenocopies the effects of the polyclonal anti-FSH antibody used in Example 2 in not only reducing subcutaneous and visceral fat, but also inducing beiging (FIG. 1), similarly to polyclonal anti-FSH antibody used in Example 2, thus indicating therapeutic potential of Hf2/antigen-binding portions thereof.

2. Blocking FSH with Anti-FSH Antibody Induces Thermogenic Adipose Tissue and Reduces Body Fat Methods and Materials FSH Peptides: Recombinant mouse FSH was obtained from R&D (8576-FS). For the cyclic AMP assay, fully glycosylated FSH24 was used. It was important for bone and fat assays to use the fully glycosylated form of FSH, owing to sub-optimal actions of the hypoglycosylated glycoform.

Immunoprecipitation: Recombinant mouse follicle stimulating hormone (FSH) (FSHα-FSHβ chimera, 2 μg) was passed through resin (Pierce Co-Immunoprecipitation Kit, 26149, Thermo Scientific) with immobilized anti-FSH antibody or goat IgG. Elution, flow-through, and consecutive wash fractions were collected and immunoblotted with a monoclonal anti-FSH antibody (Hf2).

Mass Spectrometry: The immunoprecipitated eluate was reduced (DTT, Sigma), alkylated (iodoaceteamide, Sigma), and trypsinized (trypsin, Promega). Peptides were analyzed by reversed phased (12 cm/75 μm, 3 μm $C_{18}$ beads, Nikkyo Technologies) LC-MS/MS (Ultimate 3000 nano-HPLC system coupled to Q-Exactive Plus mass spectrometer, Thermo Scientific). Peptides were separated using a gradient increasing from 6% buffer B/94% buffer A to 50% buffer B/50% buffer A in 34 minutes (buffer A: 0.1% formic acid; buffer B: 0.1% formic acid in 80% acetonitrile) and analyzed in a combined data dependent (DDA)/parallel reaction monitoring (PRM) experiment. Six FSH peptides were targeted. Tandem MS spectra were recorded at a resolution of 17,500 with m/z of 100 as the lowest mass. Normalized collision energy was set at 27, with automatic gain control (AGC) target and maximum injection time being $2 \times 10^5$ and 60 ms, respectively. Tandem MS data were extracted and queried against a protein database containing the FSHα-FSHβ chimera sequence concatenated with an E. coli background database and known common contaminants using Proteome Discoverer 1.4 (Thermo Scientific) and MASCOT 2.5.1 (Matrix Science). Acetyl (Protein N-term) and Oxidation (M) were chosen as variable modifications while all cysteines were considered carbamidomethylated. 10 ppm and 20 mDa were used as mass accuracy for precursors and fragment ions, respectively. Matched peptides were filtered using 1% False Discovery Rate calculated by Percolator and, in addition, required that a peptide was matched as rank 1 and that precursor mass accuracy was better than 5 ppm. The area of the three most abundant peptides per protein was used to estimate approximately the abundance of matched proteins.

Computational Modeling: The crystal structure of human FSH in complex with the entire ectodomain of the human FSHR was used as the template (PDB id 4AY9) for comparative modeling. The sequence of the epitope on mouse FSHβ differs by only two amino acids (LVYKDPARPKIQK (SEQ ID NO: 1)→LVYKDPARPNTQK (SEQ ID NO: 2). Several models of the modified FSβ epitope were constructed using the ICM software. Restrained minimization was carried out to remove any steric clashes. The final model was selected on the basis of the lowest Cα RMSD value after superimposition on the template structure (0.2 Å). The structure of FSHR resembles a right-hand palm, with the main body as the palm and the protruding hairpin loop as the thumb. The FSβ binds in the small groove generated between the palm and the thumb. The electrostatic surfaces generated reveal a complementary surface charge between the FSHR and F SHP.

Mice: Colonies of wild type C57BL/6 mice, Fshr[-/-] mice, ThermoMice and PhAM[excised] mice, originally obtained from Jackson Labs, were maintained in-house at Icahn School of Medicine at Mount Sinai and/or Maine Medical Center Research Institute. Mice were subjected to standard 12-hour light/dark cycles (6 am to 6 pm) and fed as below. For thermoneutrality experiments, mice were housed in temperature-controlled cages (30° C.). All protocols were approved by Institutional Animal Care and Use Committees of the respective institutions.

Pharmacokinetics: Three-month-old wild type C57BL/6 mice (n=15) were injected, i.p., with a single dose of anti-FSH antibody (100 μg/mouse), with groups of 3 mice being sacrificed at 0, 2, 6, 12 or 24 hours. Collected plasma was subject to in-house ELISA, in which two rabbit anti-goat IgGs, one of which was labeled with HRP (HRP-IgG from Jackson ImmunoResearch, Cat. #305-035-046 and unlabeled IgG from Thermo Scientific, Cat. #31133), were used to sandwich-capture goat IgG.

Pair-Feeding: Two to three-month-old C57BL/6 mice were pair-fed on high fat diet (DIO Formula D12492, 60% fat; Research Diets, Inc., New Brunswick, N.J.), or pair-fed or reverse pair-fed on normal chow (Laboratory Rodent Diet 5001; LabDiet, St Louis, Mo.) for up to 8 weeks, during which cumulative food intake was measured daily, in addition to measurements of body weight, twice-a-week. For pair-feeding, the amount of chow consumed ad libitum by the IgG group was given to the anti-FSH antibody-treated group. For the reverse pair-feeding, the anti-FSH antibody-treated group was allowed ad libitum access to food and the same amount of chow was given to IgG group, with the left-over chow being counted to determine food intake of the IgG group. Anti-FSH antibody was injected at doses between 100 and 400 μg/mouse. Experiments at Maine Medical Center were performed using a similar protocol, but both mouse groups were allowed ad libitum access to food. Numbers of mice per group are indicated in Figure Legends.

ITT and GTT: Mice were tested after 4 weeks of treatment with antibody or IgG for glucose and insulin tolerance. For GTT, mice were placed in a clean cage with water and starved overnight (16 h), following which glucose (1 g/kg) was administered intraperitoneally, and blood glucose levels measured at 0, 15, 30, 60, 90 and 120 min. post-injection using the OneTouch Ultra Glucometer (LifeScan, Inc.) per manufacturer's instructions. For ITT, antibody- or IgG-treated mice were fed ad libitum and injected intraperitoneally with insulin (1 U/kg). Glucose levels were measured at 0, 15, 30, 45, 60 and 120 min after injection.

Measurement of Body Fat: Several complementary approaches, namely quantitative nuclear magnetic resonance (qNMR), microcomputed tomography (μCT), dual energy X-ray absorptiometry (DXA), osmium μCT for bone marrow fat quantitation, and tissue weight measurements, were utilized to examine total body fat, as well as fat volume/weight in different adipose tissue compartments.

Quantitative Nuclear Magnetic Resonance: For qNMR, live mice were placed into a thin-walled plastic cylinder, with freedom to turn around. An Echo3-in-1 NMR analyzer (Echo Medical) was used to measure fat, lean and total mass, per manufacturer's instructions.

Micro-computed Tomography: For μCT, the protocol of Judex et al, Quantification of adiposity in small rodents using micro-CT. *Methods* 50, 14-19, doi:10.1016/j.ymeth.2009.05.017 (2010) was followed, hereby incorporated by reference in its entirety. A VivaCT-40 (Scanco AG, Bassersdorf, Switzerland) with a detector size of 1024×256 pixels was utilized for imaging fat and measuring fat volume in thoracolumbar compartments. Mice were anaesthetized by purging the chamber with 5% isoflurane and $O_2$ for 5 to 10 minutes (X.E.G.) or with Avertin (C.J.R.) and positioned with both legs extended. The torso of each mouse was scanned at an isotropic voxel size of 76 μm (45 kV, 133 μA) and a 200 ms integration time. Two-dimensional gray scale image slices were reconstructed into a 3-dimensional tomogram, with a Gaussian filter ($\sigma=0.8$, support=1) applied to reduce noise. Scans were reconstructed between the proximal end of L1 and the distal end of L5. The head and feet were not scanned and/or evaluated because of the relatively low amount of adiposity in these regions, and to allow for a decrease in scan time and radiation exposure to the animals. Regions of fat were manually traced and thresholded at 5% maximum grayscale value. The high resolution of this method allows for the imaging of both subcutaneous adipose tissue (SAT) and visceral adipose tissue (VAT). An automated algorithm was used to quantify the volume of VAT and SAT using previously described methods (DeMambro, V. E. et al. Igfbp2 Deletion in Ovariectomized Mice Enhances Energy Expenditure but Accelerates Bone Loss. *Endocrinology* 156, 4129-4140, doi:10.1210/en.2014-1452 (2015), Lublinsky, S., Ozcivici, E. & Judex, S. An automated algorithm to detect the trabecular-cortical bone interface in micro-computed tomographic images. Cakif Tissue Int 81, 285-293, doi:10.1007/s00223-007-9063-8 (2007, both references hereby incorporated by reference in their entireties)

Dual Energy X-Ray Absorptiometry: BMD and body fat measurements were performed using a Lunar Piximus DXA, with a precision of <1.5%. Anaesthetized mice were subject to measurements, with the cranium excluded. The instrument was calibrated each time before use by employing a phantom per manufacturer's recommendation.

Osmium Quantitation of Marrow Fat: Osmium staining for marrow fat was performed in collaboration with the Small Animal Imaging Core and the Physiology Core at Maine Medical Center Research Institute, using previously published methods; Scheller, E. L. et al. Use of osmium tetroxide staining with microcomputerized tomography to visualize and quantify bone marrow adipose tissue in vivo. Methods Enzymol 537, 123-139, (2014), hereby incorporated by reference in its entirety. Briefly, tibias were isolated, fixed with 10% formalin for 24 hours, washed, and then decalcified for 14 days in EDTA. Upon further washing, bones were stained for 48 hours in 1% osmium tetraoxide. Following subsequent washes, bones were scanned in PBS with an energy level of 55 kVp, and intensity of 145 μA using the VivaCT-40 (Scanco AG). The integration time was set to 500 ms at a maximum isotropic voxel size of 10.5 μm at a high-resolution setting. Two voxels of interest (VOIs) were selected as shown in FIG. 8C.

Indirect calorimetry: Indirect calorimetry was performed using the Promethion Metabolic Cage System (Sable Systems) located in the Physiology Core of Maine Medical Center Research Institute. Data acquisition and instrument control were performed using MetaScreen software (v.2.2.18) and raw data processed using ExpeData (v.1.8.2) (Sable Systems). An analysis script detailing all aspects of data transformation was used. The study consisted of a 12-h acclimation period followed by a 72-h sampling duration. Each metabolic cage in the 16-cage system consisted of a cage with standard bedding, a food hopper, water bottle, and 'house-like enrichment tube' for body mass measurements, connected to load cells for continuous monitoring, as well as 11.5-cm running wheel connected to a magnetic reed switch to record revolutions. Ambulatory activity and position were monitored using XYZ beam arrays with a beam spacing of 0.25 cm. From these data, mouse pedestrial locomotion and speed within the cage were calculated. Respiratory gases were measured using the GA-3 gas analyzer (Sable Systems) equipped with a pull-mode, negative-pressure system. Air flow was measured and controlled by FR-8 (Sable Systems), with a set flow rate of 2,000 ml/min. Oxygen consumption ($VO_2$) and carbon dioxide production ($VCO_2$) (not shown) were reported in mL per minute. Water vapour was measured continuously and its dilution effect on $O_2$ and $CO_2$ were compensated mathematically in the analysis stream. Energy expenditure (EE) was calculated using: kcal/h=60* (0.003941* $VO_2$+0.001106*$VCO_2$) (Weir Equation) and respiratory quotient (RQ) was calculated as $VCO_2/VO_2$. Ambulatory activity and wheel running were determined simultaneously with the collection of the calorimetry data. Two independent methods were used to derive resting energy expenditure (REE) and active energy expenditure from the time-dependent calorimetry and activity data. First, REE was determined as the average EE of 30-min intervals of no activity, and active EE as the average EE of 15 min. of the most active states. Second, penalized spline regression was used to estimate the continuous REE (or resting metabolic rate (RMR)) and active EE related to physical activity (AEE (PA)), using four equidistant knots per day in the spline function and optimizing the activity-related preprocessing parameters with respect to the regression residuals. Sleep hours were determined as any inactivity lasting greater than 40 s or more. This latter analysis provided an independent verification for a lack of relationship between physical activity and EE; shown in FIG. 3L.

In Vivo Luciferase Imaging: In the ThermoMouse, a luciferase reporter construct, Luc2-T2A-tdTomato, is inserted into the Ucp1 locus on the Y-chromosome (see FIG. 2D). Activation of Ucp1 expression leads to upregulation of Luc2, which can be quantitated in vivo by radiance measurements using IVIS Spectrum In Vivo Imaging System (Perkin Elmer) following the injection of D-Luciferin (10 μL/g). 3 month-old male ThermoMice were treated with anti-FSH antibody or goat IgG (200 μg/day/mouse) for 2 or 8 weeks while being pair-fed on high fat diet, followed by D-Luciferin injection and radiance capture from dorsal and/or ventral surfaces of entire body, inguinal white adipose tissue and interscapular brown adipose tissue regions. In separate experiments, Thermo cells ($1.5 \times 10^6$) were implanted into both flanks of nu/nu mice, which were fed on normal chow and injected with anti-FSH antibody (200 μg/mouse/day) for 8 weeks, following which Luc2 radiance was quantitated post D-Luciferin using IVIS. As basal levels of Ucp1 expression can be variable in transgenic mice, and could therefore confound data interpretation, an early time point for radiance capture at 5 min post-d-luciferin was routinely performed. This allowed for evaluation of 'basal' Ucp1 expression, and mice whose measured total flux and/or average radiance at the 5-min time point is more than 1 s.d. from the mean of group were excluded. For independent confirmation, frozen sections of resected areas where cells had been implanted were examined for tdTomato fluorescence.

Histology, Immunodetection and qPCR: Tissues were subject to haematoxylin and eosin staining or immunocytochemistry. Images were captured using the Keyence or Zeiss microscope. Immunocytochemistry for FSHR used standard protocols and a commercially available anti-Fshr antibody (Lifespan, Cat. #LS-A4004). tdTomato and mito-Dendra2 fluorescence was examined in frozen, 15-μm sections. Quantitative PCR was performed using appropriate primer sets using Prism 7900-HT (Applied Biosystems Inc.). For cAMP measurements, cells were treated for 20 min with Fsh and/or CL-316,243, with or without a 16-h pre-incubation with pertussis toxin (100 ng mL$^{-1}$; European Pharmacopoeia) (in the presence of 0.1 mM IBMX). Cyclic AMP was measured in cell extracts using an ELISA kit (Cayman, 581001). For irisin and metrnl measurements, commercially available ELISA was used (Phoenix, EK-067-29 and R&D, DY7867, respectively). Plasma FSH and E2 levels were measured by ELISAs (Biotang, M7581 and M7619, respectively).

Noradrenaline Levels: Thirty-two mice fed on a high-fat diet were treated with antibody or IgG (200 μg per mouse per day) for 7 weeks. Half of each group was killed at the outset following blood draw, and the other half was injected with α-methyl-p-tyrosine (AMPT; 250 mg kg$^{-1}$), with a supplementary dose (125 mg kg$^{-1}$) 2 h later. After a further 2 h, both groups were killed following blood draw. Extraction and HPLC were conducted at the Core CTSI Laboratory at Yale Medical School.

Statistics: From preliminary micro-CT data, a marked, up to threefold, difference in fat volumes with 4 or 5 mice per group was found. Using a pre-specified effect size (x1-x2)/s of 3, a normalized Z-score at α=0.05 (Za) of 1.96, and assuming that standard deviation (5) is half the width of the confidence interval (W) [$N=4Z^2 a S^2/W^2$], 4 mice per group was calculated to be sufficient for 95% statistical significance at 0.8 power (α=0.05, β=0.20). Statistically significant differences between any two groups were examined using a two-tailed Student's t-test, given equal variance. P values were considered significant at or below 0.05.

Randomization, Blinding, and Exclusion: Mice were randomly picked for injection with IgG or antibody to ensure equal distribution of body weight across the groups. Technicians who generated and analysed micro-CT and qNMR data at Columbia University and Mount Sinai, respectively, were blind to the mouse groups (FIGS. 1, 4, 5, 6, 8, and 9). Additionally, the technician at the Mount Sinai Imaging Core Facility who generated data with Thermo mice (FIG. 14) and Thermo cell implants into nu/nu mice (FIG. 11D) was also blind to the mouse groups. The fundamental data were confirmed at Maine Medical Center. For experiments with Thermo mice, basal Luc2 measurements following d-luciferin injections were made before sampling. Luc2 radiance at 5 min is expected to be low. A pre-specified determination was made that if Luc2 radiance in a given mouse exceeded 1 standard deviation of the mean, that mouse was excluded. One mouse was excluded on the basis of this criterion.

Results and Discussion

Figure 2:
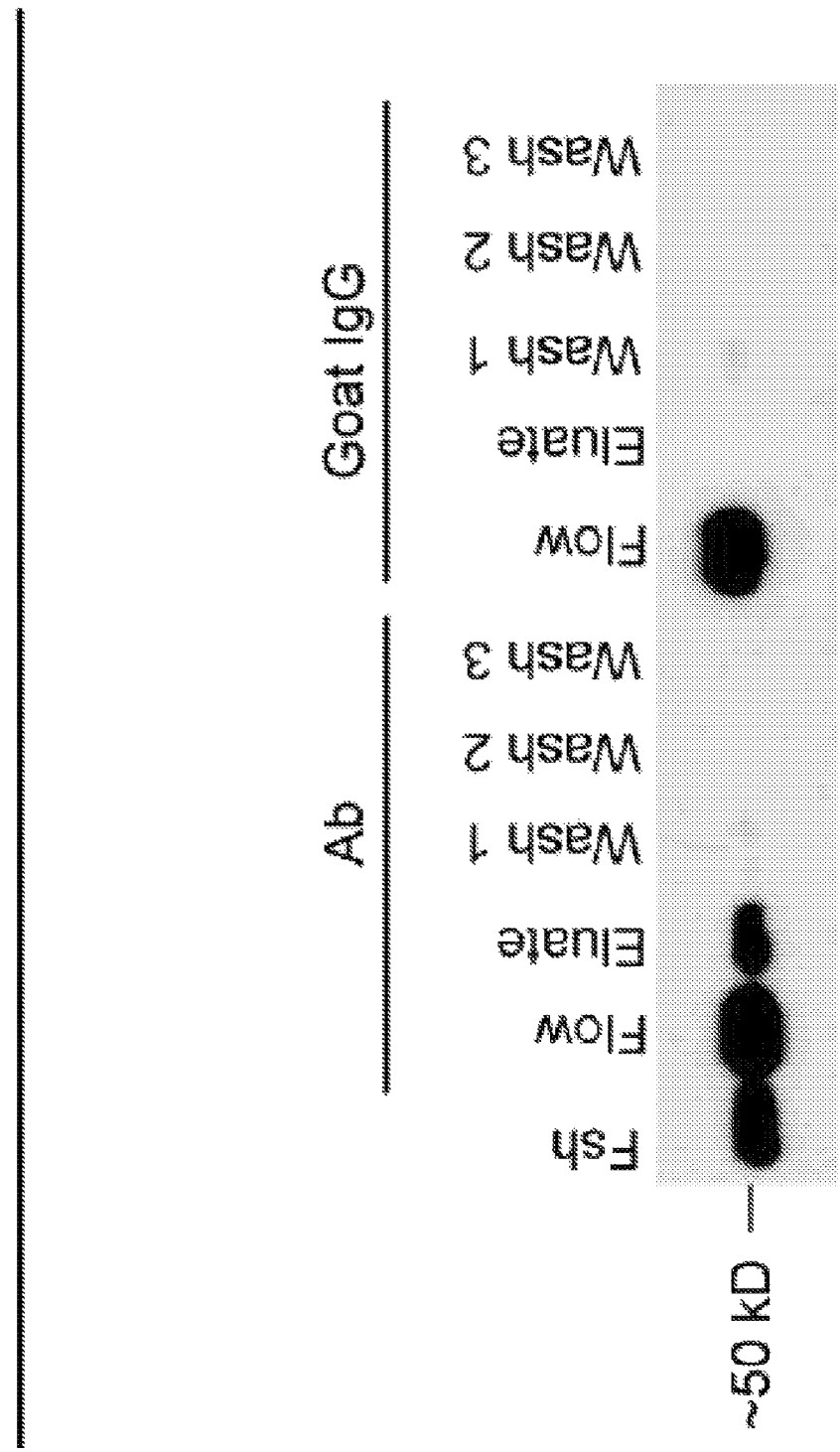
FIGS. 2A, 2B, 2C, 2D, and 2E represent that anti-FSH antibody blocks FSH-FSHR interaction at physiological FSH concentrations in plasma.
Figure 2:
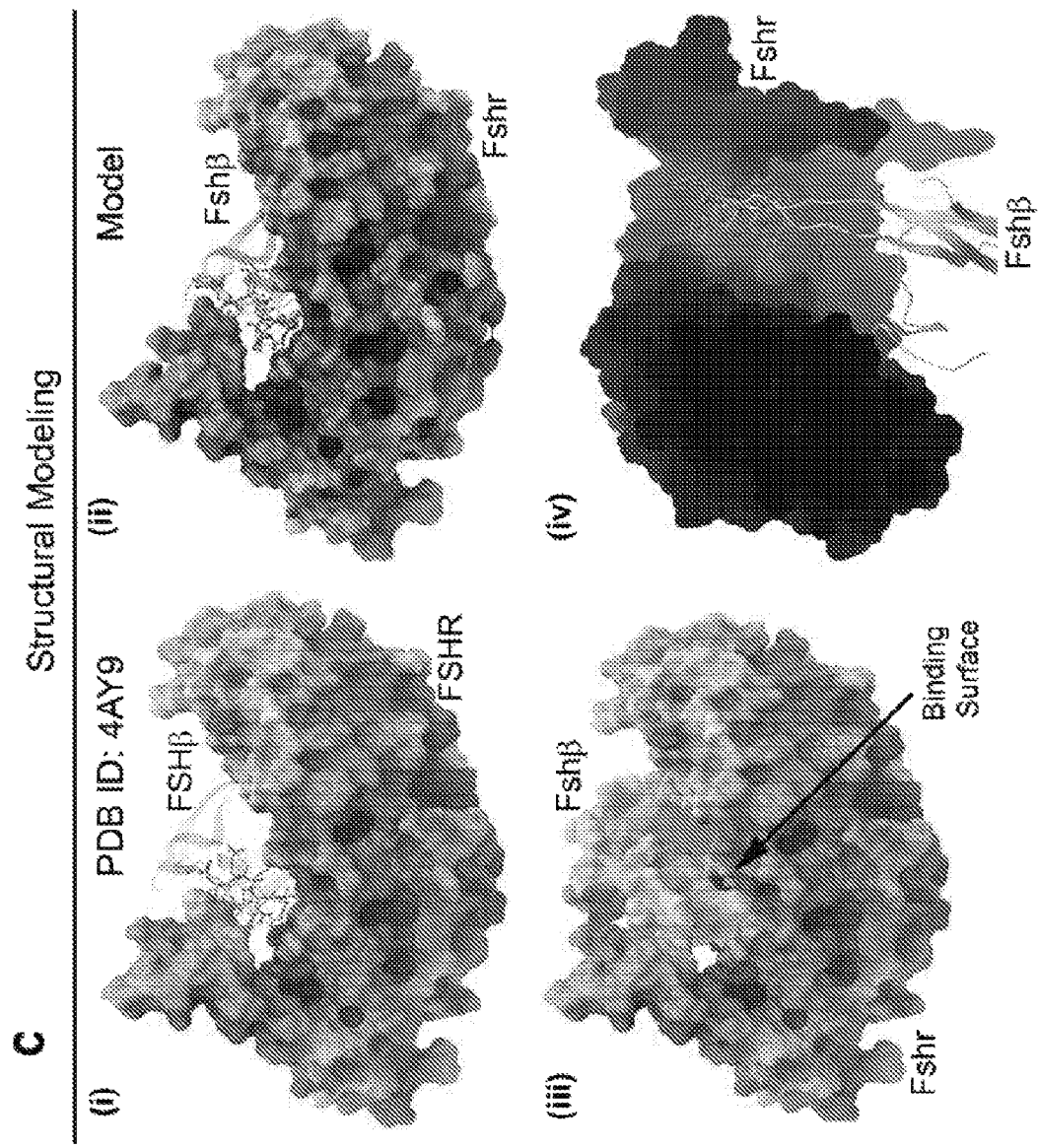
Figure 2:
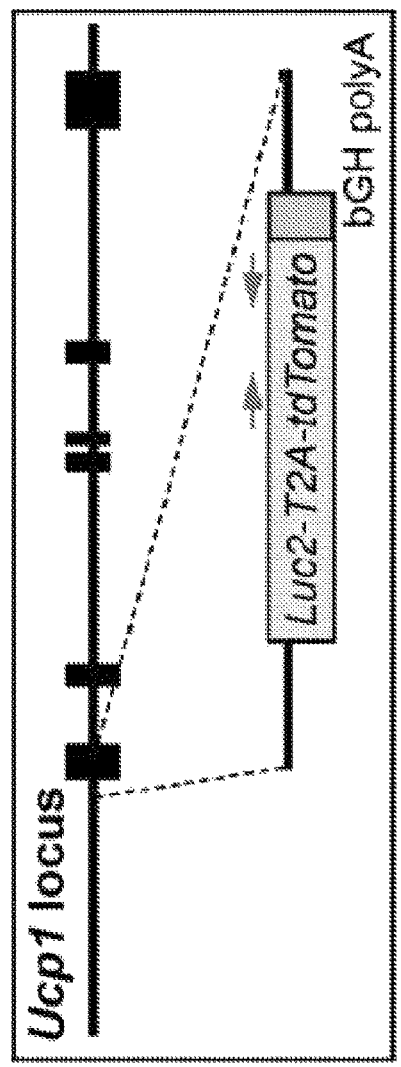
Figure 2:
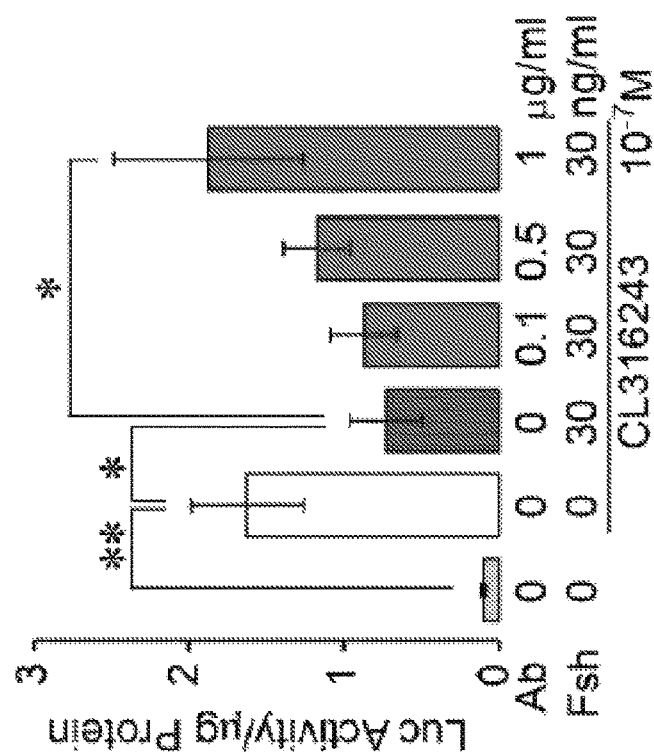
Figure 2:
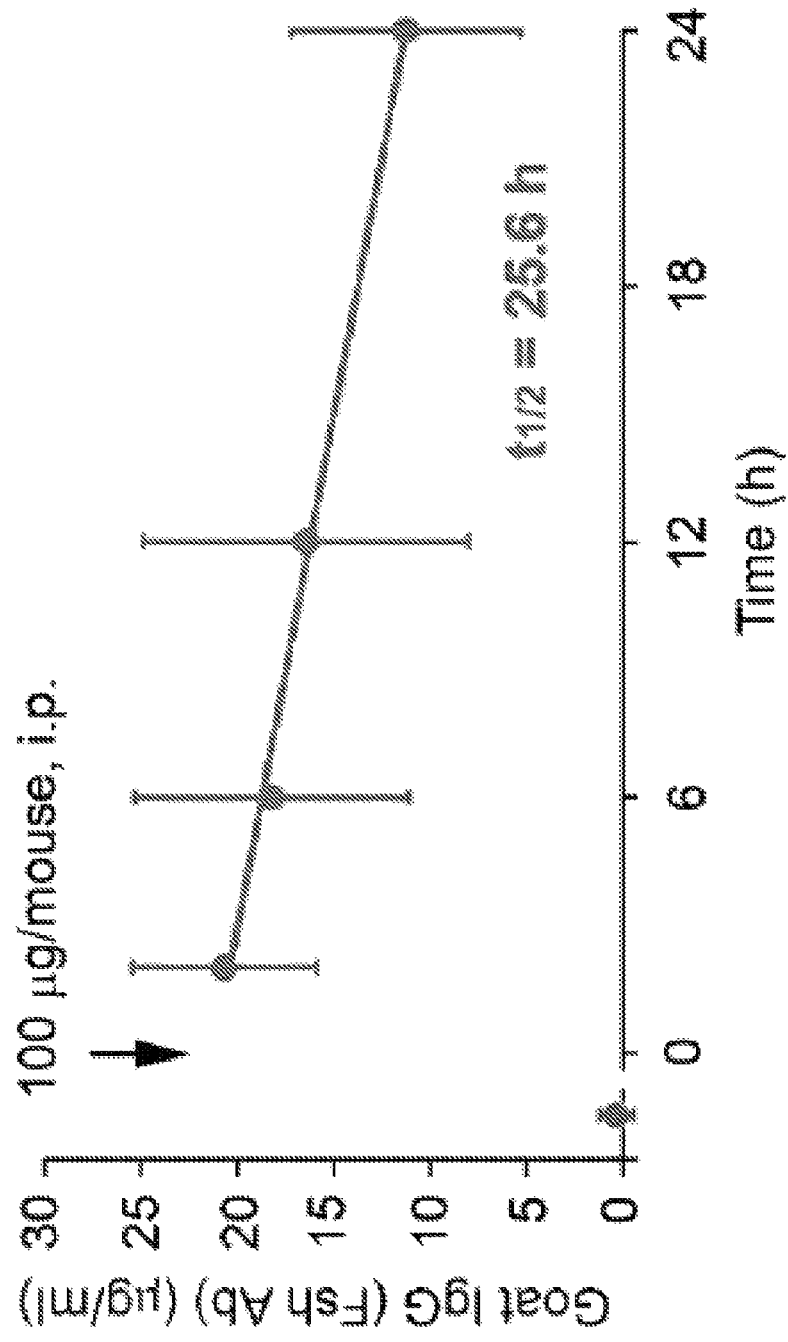

Anti-FSH Antibody Reduces High-Fat Diet-Induced Obesity:

It has been shown that a polyclonal antibody raised against a 13-amino acid sequence (LVYKDPARPNTQK, SEQ ID NO: 2) of the β-subunit of FSH (FSHβ) inhibits ovariectomy-induced bone loss in mice. To establish that the antibody binds to FSβ and interrupts the interaction of this subunit with its receptor, recombinant mouse FSH was passed through resin with immobilized FSH antibody or goat immunoglobulin G (IgG), and fractions immunoblotted with a new monoclonal FSH antibody, Hf2, raised against the corresponding human LVYKDPARPKIQK (SEQ ID NO: 1) motif. Characterization of Hf2 is found in Example 1 supra. FIG. 2A shows an approximately 50-kDa band in both elution and flowthrough fractions passed through immobilized FSH antibody, whereas with immobilized goat IgG, all protein appeared in the flow-through fraction. Liquid chromatography with tandem mass spectrometry (LC-MS/MS) of the antibody-immunoprecipitated eluate yielded 10 peptides corresponding to the murine FSHα-FSHβ chimera (SEQ ID NO: 17) (FIG. 2B, TABLE 5 below), definitively establishing that FSH was the binding target of the anti-FSH antibody.

Full-length murine FSHα-FSHβ chimera is reproduced below. SEQ ID NO: 2 is underlined:

```
                                          (SEQ ID NO: 17)
HSCELTNITISVEKEECRFCISINTTWCAGYCYTRDLVYKDPARPNTQKV

CTFKELVYETVRLPGCARHSDSLYTYPVATECHCGKCDSDSTDCTVRGLG
```

-continued

PSYCSFSEMKEGGGSGGGSGGGSLPDGDFIIQGCPECKLKENKYFSKLGA

PIYQCMGCCFSRAYPTPARSKKTMLVPKNITSEATCCVAKAFTKATVMGN

ARVENHTECHCSTCYYHKS.

TABLE 5

Tryptic Peptide Fragments Matching Mouse FSHα-FSHβ Chimera
(Oxidated methionine and carbamidomethylated cysteine are underlined.)

| SEQUENCE | Area | PEP | IonScore | Exp Value |
|---|---|---|---|---|
| EGGGSGGGSGGGSLPDGDFIQGCPECK (SEQ ID NO: 18) | 9.302e8 | 9.59e-10 | 167 | 1.959e-17 |
| VCTFKELVYETVR (SEQ ID NO: 19) | 7.910e7 | 1.58e-5 | 75 | 1.372e-7 |
| GLGPSYCSFSEMK (SEQ ID NO: 20) | 7.617e9 | 3.38e-4 | 70 | 1.028e-7 |
| CDSDSTDCTVR (SEQ ID NO: 21) | 1.533e8 | 1.366e-4 | 68 | 1.652e-7 |
| LGAPIYQCMGCCFSR (SEQ ID NO: 22) | 3.278e9 | 1.26e-5 | 67 | 2.046e-7 |
| GLGPSYCFSFEMK (SEQ ID NO: 23) | 3.055e9 | 1/14e-4 | 64 | 4.325e-7 |
| HSDSLYTYPVATECGCGK (SEQ ID NO: 24) | 6.766e9 | 1.5e-5 | 63 | 5.164e-7 |
| LGAPIYQCMGCCFSR (SEQ ID NO: 25) | 8.532e8 | 5.58e-5 | 58 | 1.507e-6 |
| VENHTECHCSTCYYHK (SEQ ID NO: 26) | 3.318e7 | 2.11e-5 | 25 | 3.4992e-3 |
| DLVYKDPARPNTQK (SEQ ID NO: 27) | 7.099e8 | 3.54e-3 | 13 | 0.29002 |
| ELVYETVR (SEQ ID NO: 28) | 3.388e10 | 1.3e-2 | 44 | 1.583e-4 |
| TMLVPK (SEQ ID NO: 29) | 2.256e10 | 2.28e-1 | 35 | 1.6717e-3- |

| SEQUENCE | Charge | MH+ [Da] | ΔM [ppm] | m/z [Da] |
|---|---|---|---|---|
| EGGGSGGGSGGGSLPDGDFIQGCPECK (SEQ ID NO: 18) | 2 | 2652.12920 | -0.39 | 1326.56824 |
| VCTFKELVYETVR (SEQ ID NO: 19) | 3 | 1643.84507 | -0.70 | 548.61987 |
| GLGPSYCSFSEMK (SEQ ID NO: 20) | 2 | 1462.363225 | -1.32 | 731.81976 |
| CDSDSTDCTVR (SEQ ID NO: 21) | 2 | 1315.48796 | -0.76 | 658.24762 |
| LGAPIYQCMGCCFSR (SEQ ID NO: 22) | 2 | 1819.77080 | -2.17 | 910.38904 |
| GLGPSYCFSFEMK (SEQ ID NO: 23) | 2 | 1478.62834 | -0.51 | 739.81781 |
| HSDSLYTYPVATECGCGK (SEQ ID NO: 24) | 3 | 2124.90799 | -1.60 | 708.97418 |
| LGAPIYQCMGCCFSR (SEQ ID NO: 25) | 2 | 1835.76677 | -1.57 | 918.38702 |
| VENHTECHCSTCYYHK (SEQ ID NO: 26) | 4 | 2124.83559 | 1.65 | 531.96436 |
| DLVYKDPARPNTQK (SEQ ID NO: 27) | 3 | 1644.86917 | -0.78 | 548.96124 |
| ELVYETVR (SEQ ID NO: 28) | 2 | 1008.53557 | -0.50 | 504.77142 |
| TMLVPK (SEQ ID NO: 29) | 2 | 668.40581 | -0.64 | 344.70654 |

It was investigated whether the polyclonal FSH antibody, which was raised against LVYKDPARPNTQK (SEQ ID NO: 2), could block the interaction of FSH with the mouse FSH receptor (FSHR) (FIG. 2C). The crystal structure of the human FSH-FSHR complex (Protein Data Bank (PDB) accession 4AY9) with the motif LVYKDPARPKIQK (SEQ ID NO: 1) was used to model mouse FSH-FSHR interactions (with the motif LVYKDPARPNTQK (SEQ ID NO: 2); FIG. 2C). Notably, the loop from FSIII3 containing this peptide sequence tucked into a small groove in the FSHR, so that binding of an antibody to this sequence would inevitably block access of FSHβ to its FSHR binding site (FIG. 2C). To test whether the antibody reversed FSH-induced inhibition of uncoupling protein 1 (Ucp1), a master regulator of adipocyte beiging and thermogenesis, immortalized dedifferentiated brown adipocytes derived from the Thermo-Mouse (also known as Thermo cells) were used, in which the Ucp1 promoter drives a Luc2-T2A-tdTomato reporter 10 (FIG. 2D). Exogenous FSH (30 ng ml$^{-1}$) inhibited Luc2 activity in medium devoid of FSH, and the FSH antibody reversed this inhibition in a concentration-dependent manner (complete at $1_{14}$ ml$^{-1}$ antibody). To determine whether a serum concentration of at least 1 μg ml$^{-1}$ would result from a single intraperitoneal injection of 100 μg antibody, enzyme-linked immunosorbent assays (ELISAs) were performed. Mice injected with antibody showed a sharp increase in plasma antibody levels, measured as goat IgG, 2 h after the injection and levels remained at 10 μg ml$^{-1}$ or more for up to at least 24 h (t 1/2=25.6 h) (FIG. 2E).

Figure 3:
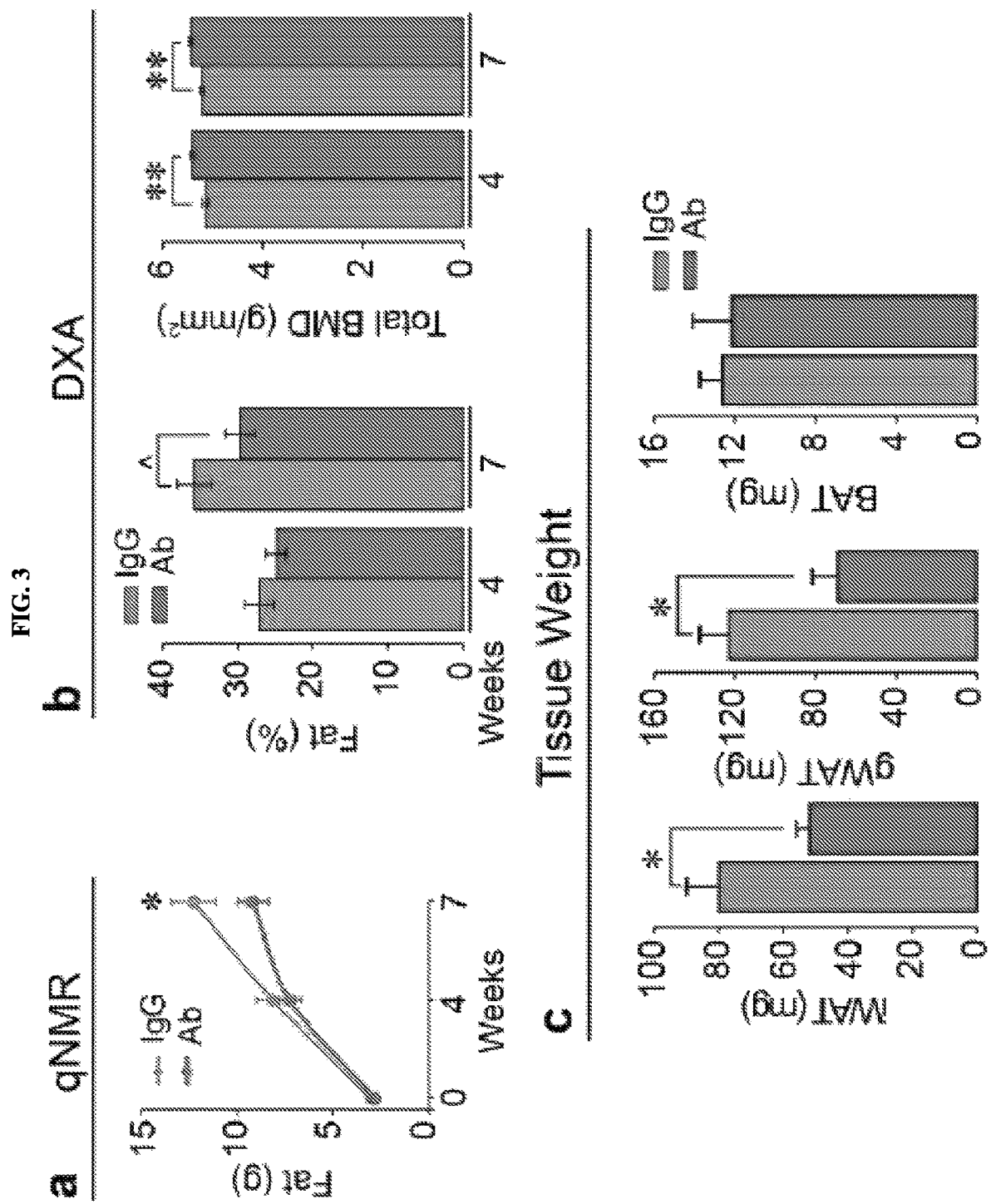
FIGS. 3A, 3B, 3C, 3D, 3E, 3F, 3G, 3H, 3I, 3J, 3K, and 3L represent the effects of anti-FSH antibody on body fat and energy homeostasis in mice fed on a high-fat diet.
Figure 3:
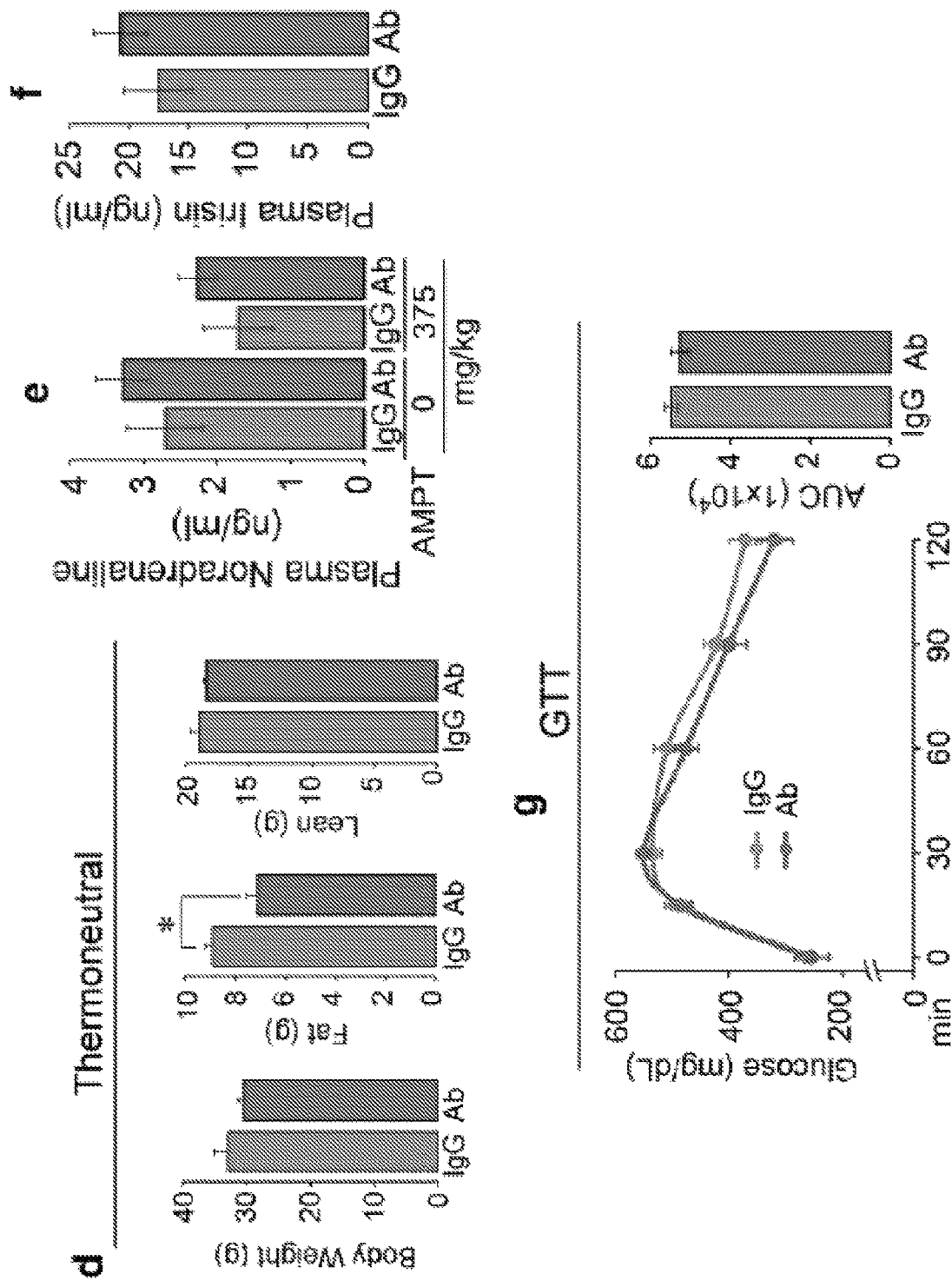
Figure 3:
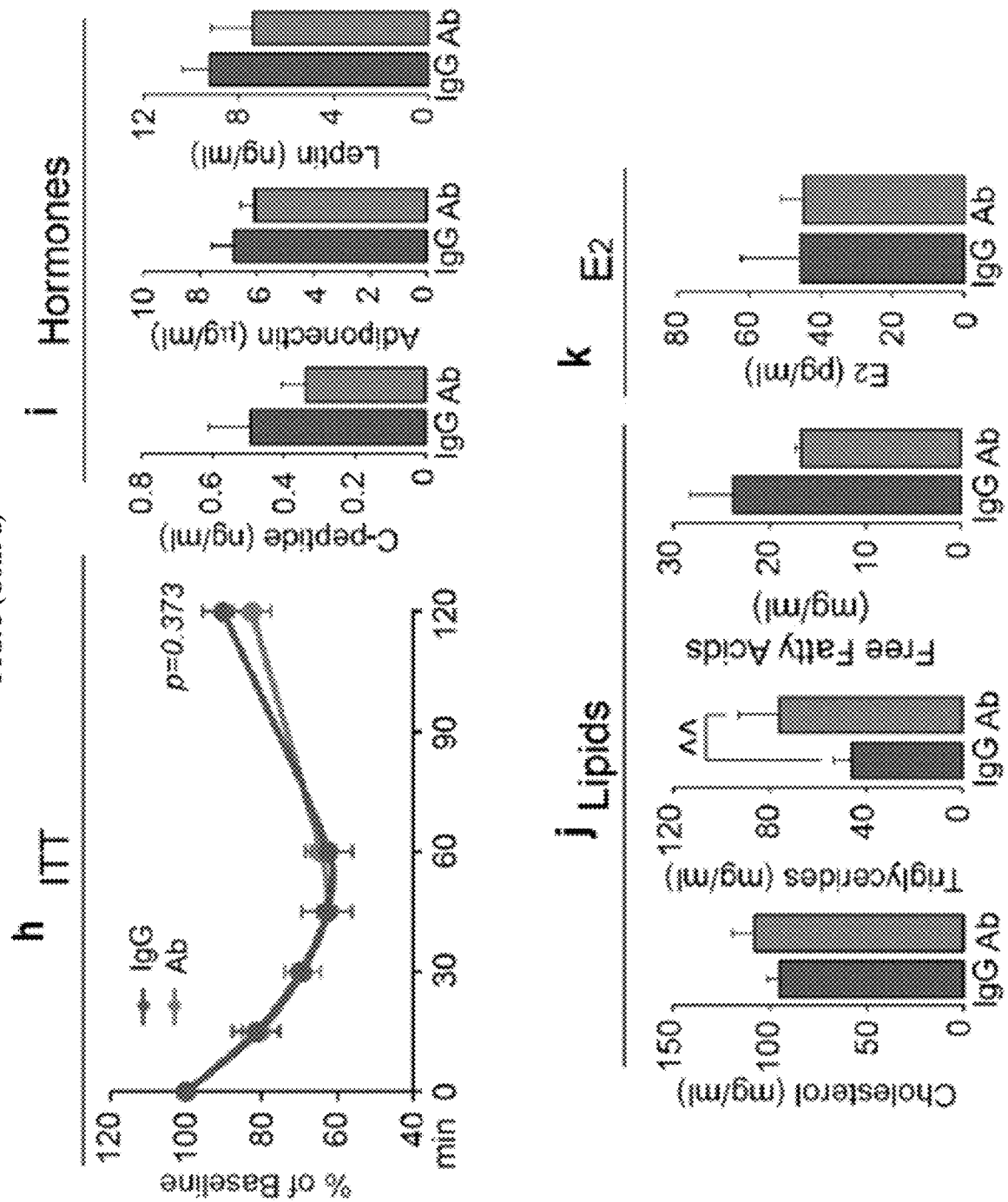
Figure 3:
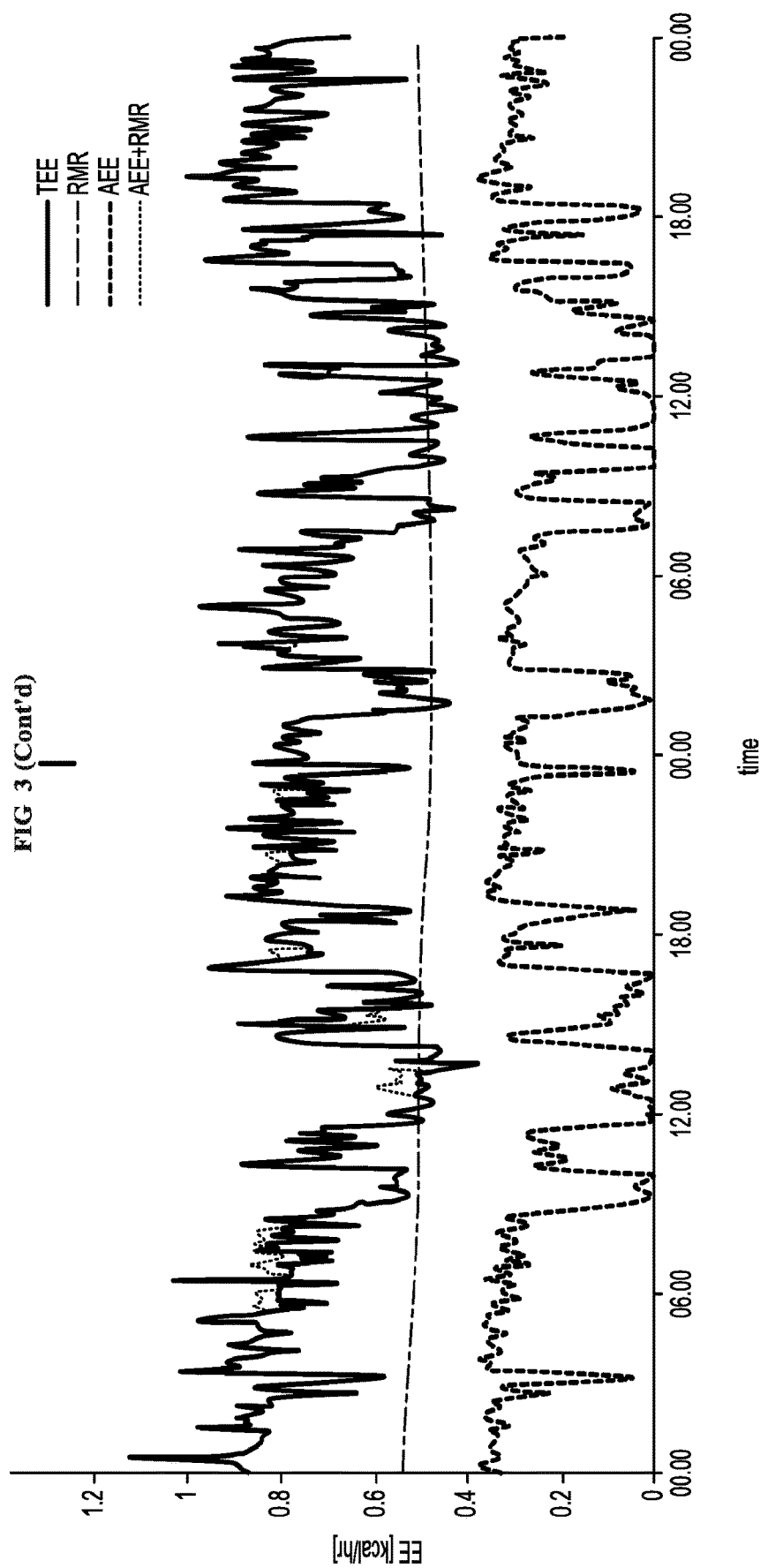
Figure 4:
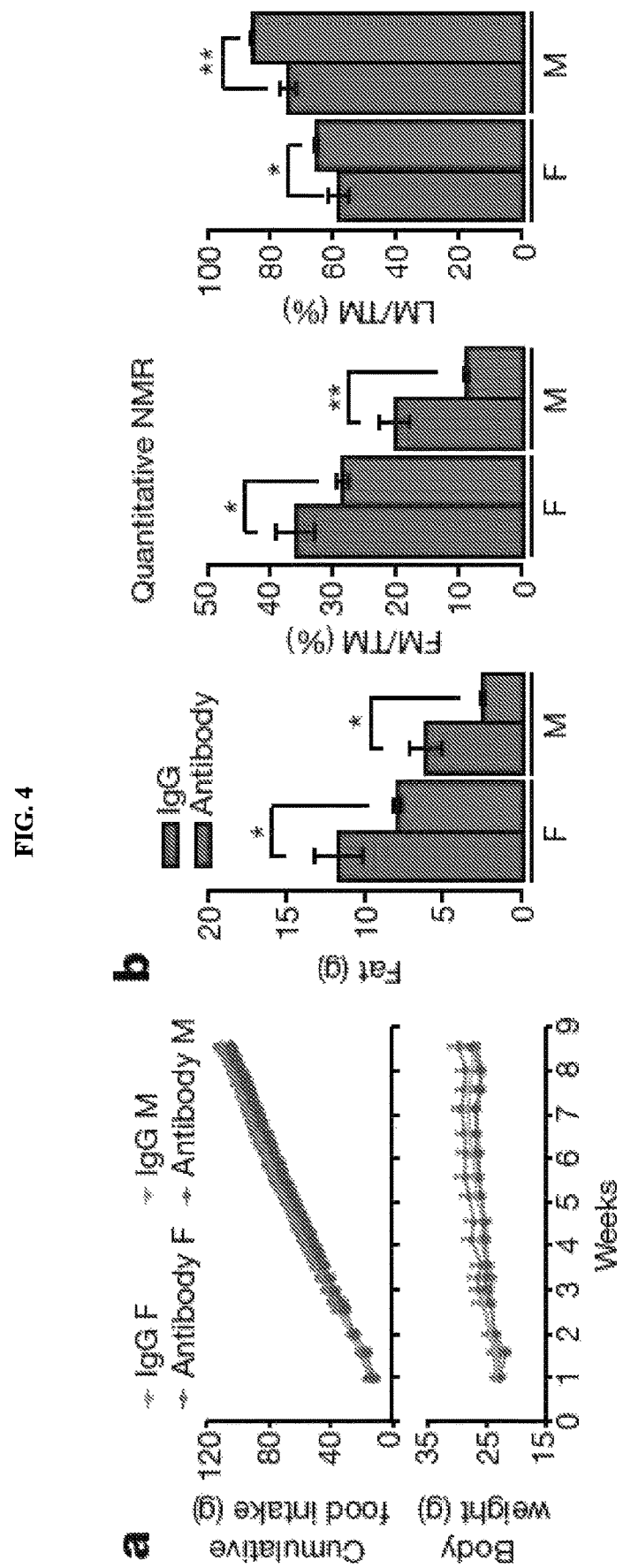
FIGS. 4A, 4B, and 4C represent that anti-FSH antibody reduces obesity in mice on a high-fat diet. Polyclonal anti-FSH antibody (Ab) or goat IgG ($200_{14}$ per day per mouse) was injected intraperitoneally for 8 weeks into 3-month-old female (F) and male (M) C57BL/6J mice pair-fed on high-fat diet.
Figure 4:
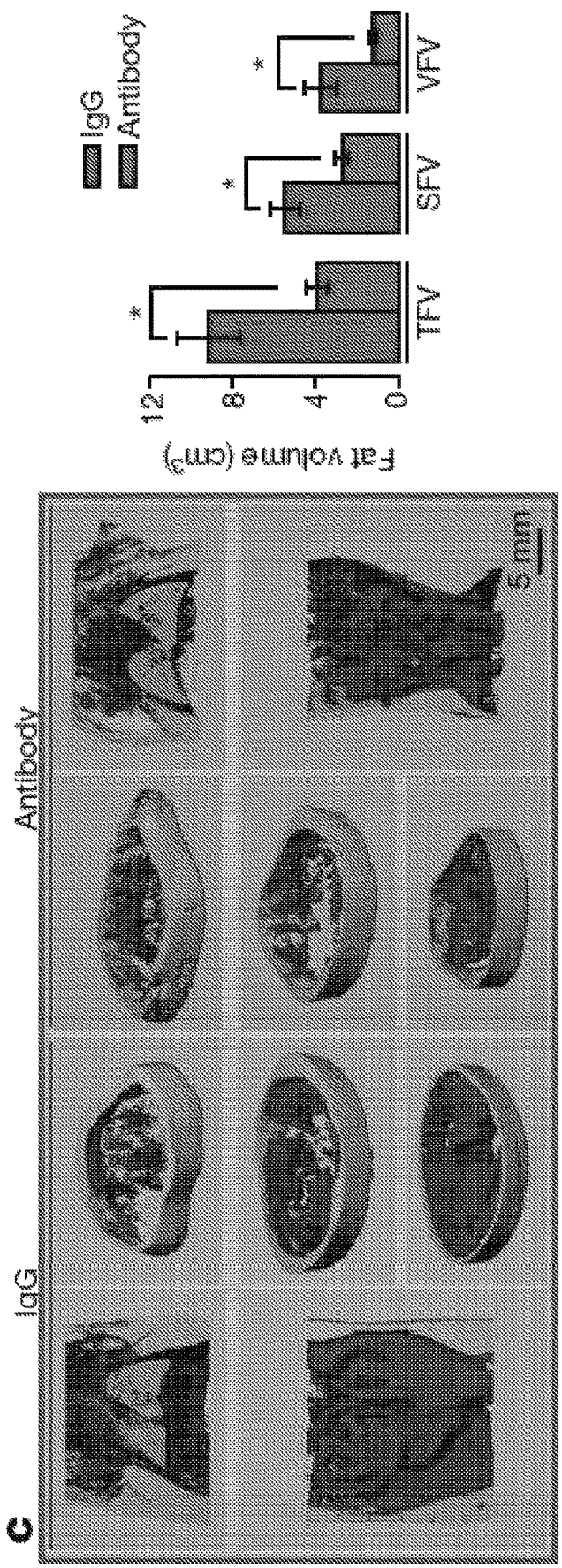
Figure 5:
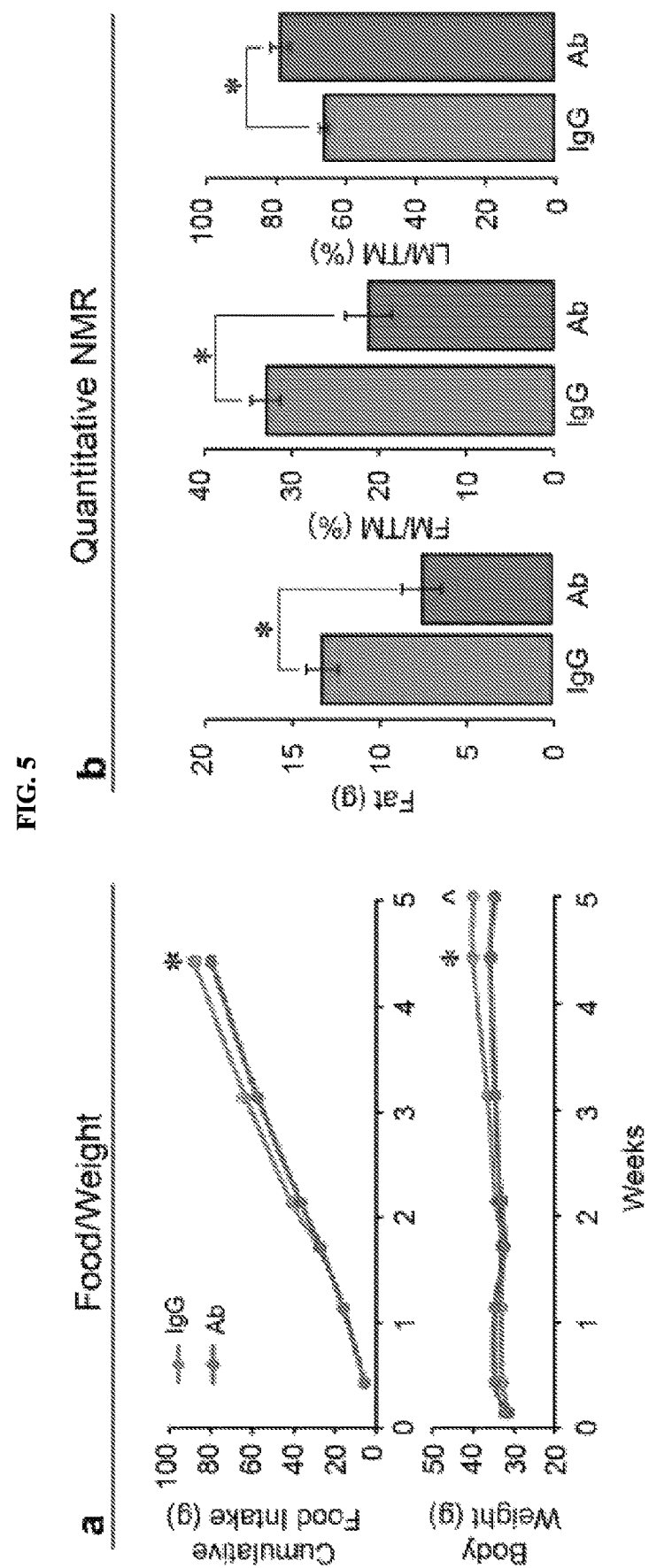
FIGS. 5A, 5B, and 5C represent that anti-FSH antibody reduces obesity in mice on a high-fat diet, measuring effect of anti-FSH antibody or goat IgG (200 μg per day per mouse, intraperitoneally) injected daily into 8-month-old C57BL/6 male mice pair-fed on high-fat diet (n=2 or 3 mice per group).
Figure 5:
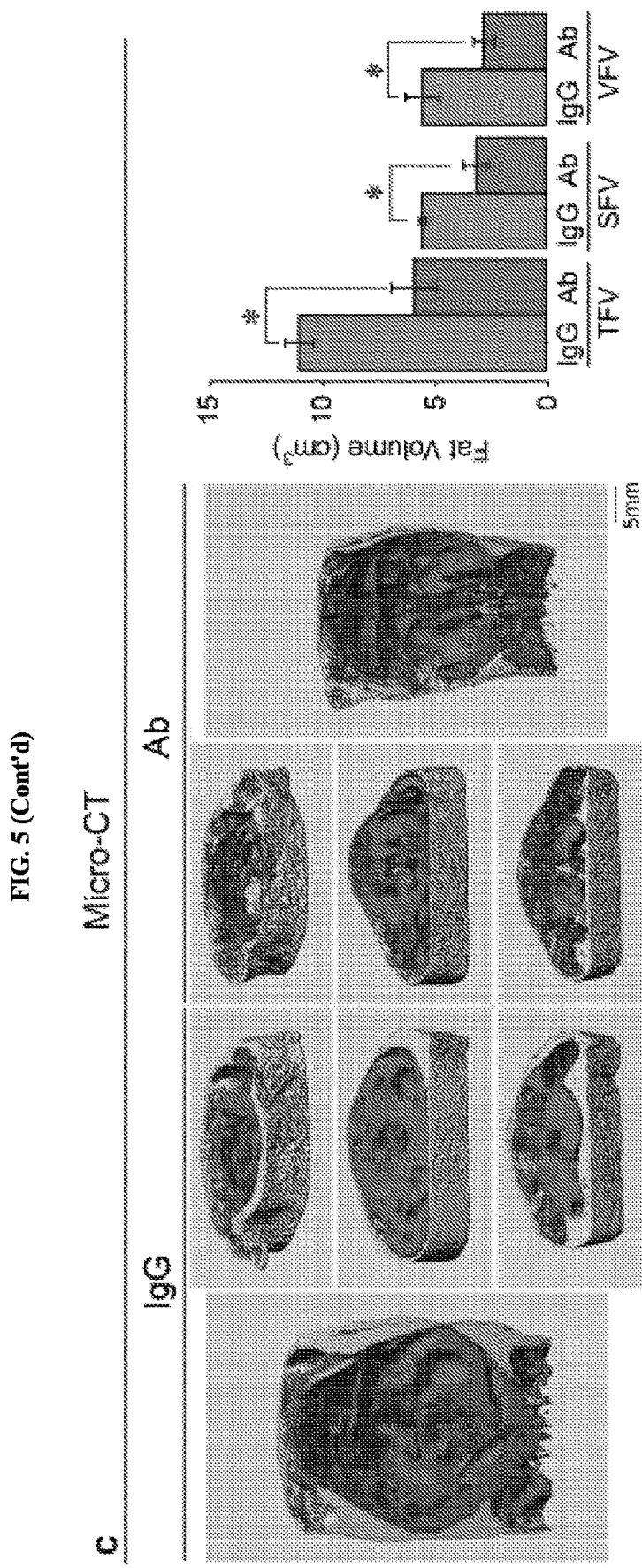
Figure 6:
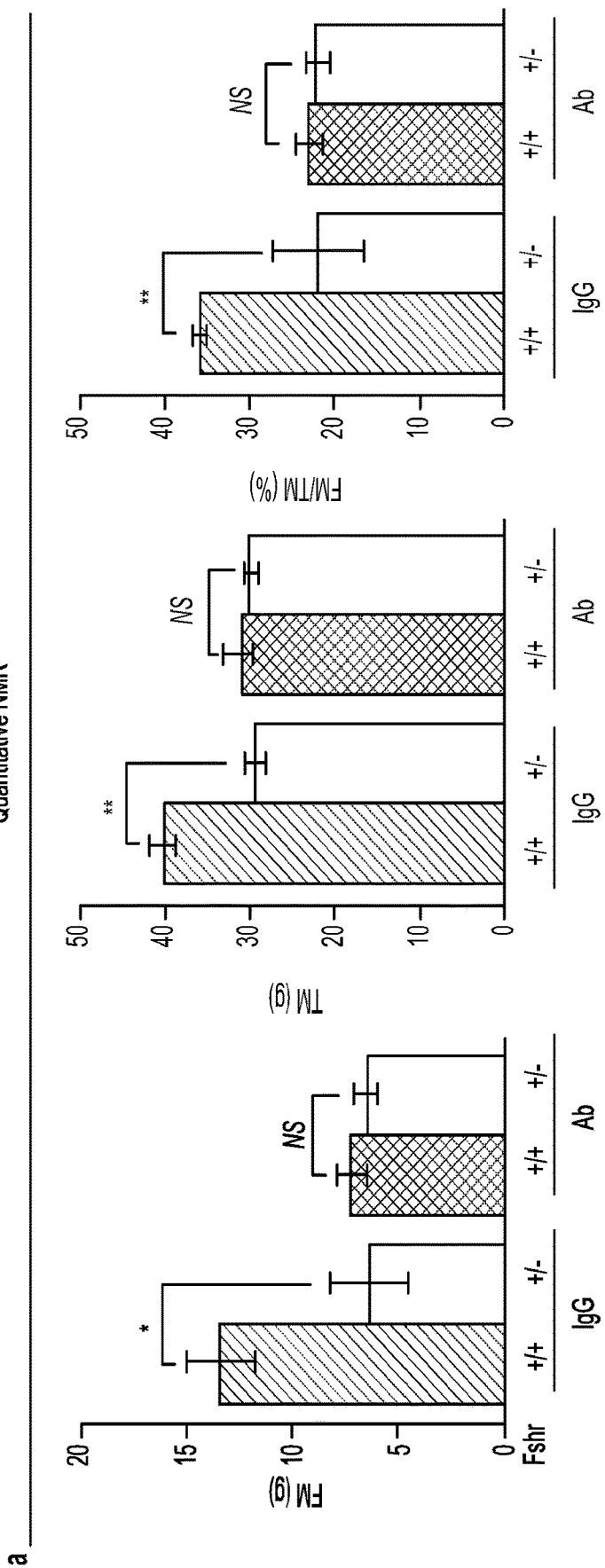
FIGS. 6A, 6B, and 6C represent Fshr-haploinsufficient male mice phenocopy the anti-adiposity action of anti-FSH antibody and fail to respond to the antibody, confirming in vivo antibody specificity.
Figure 6:
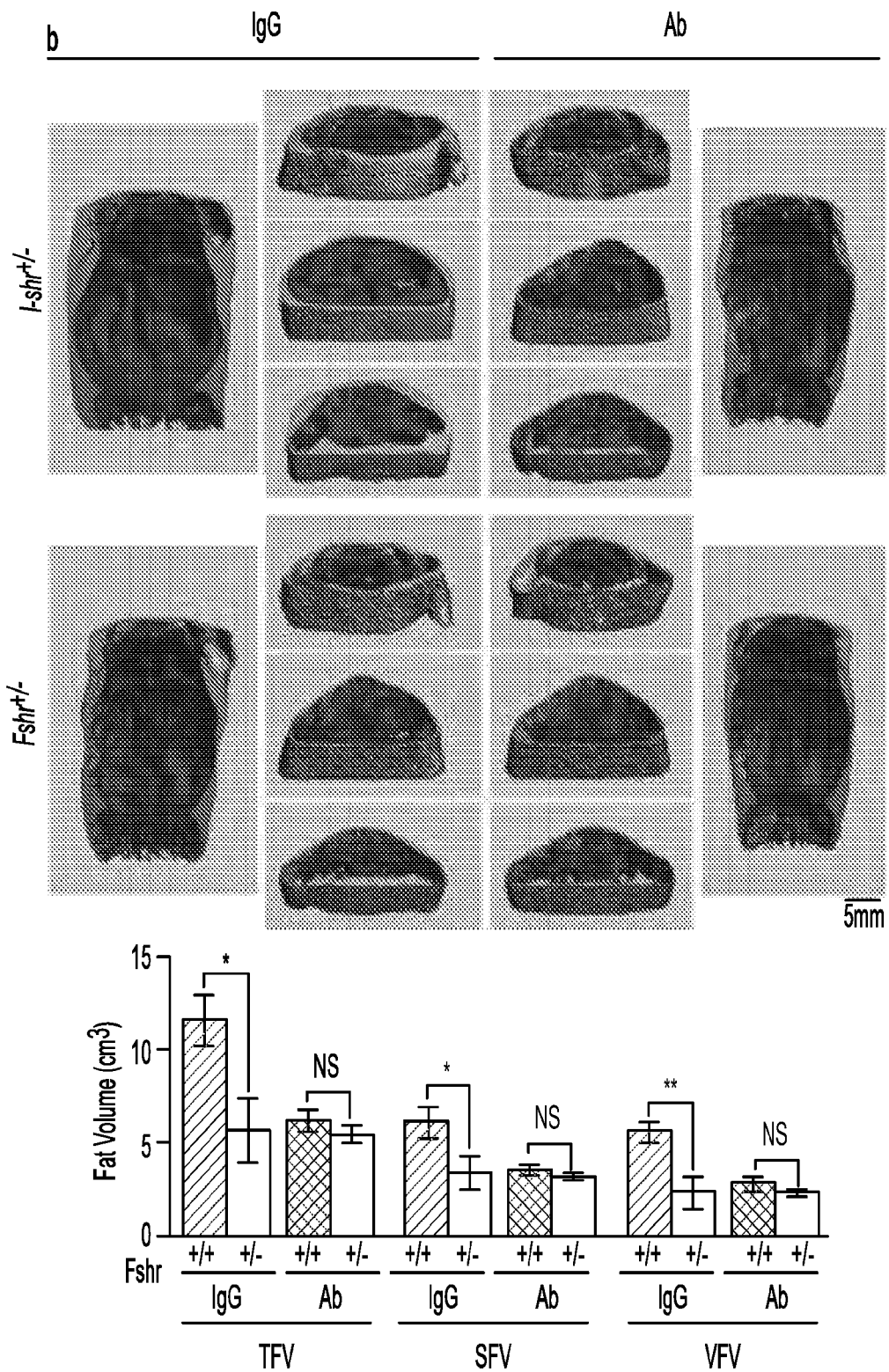
Figure 6:
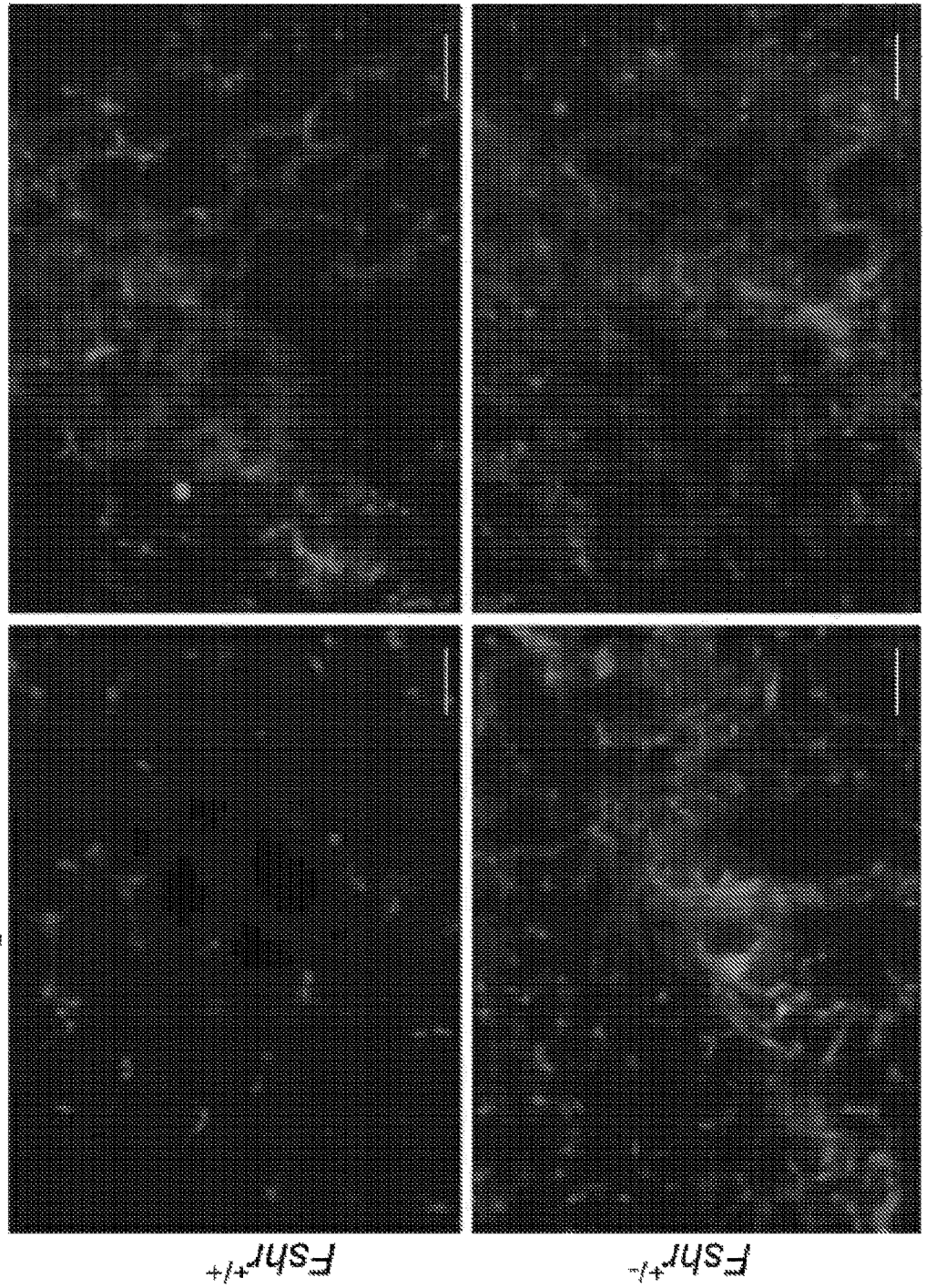

The effects of FSH antibody or goat IgG were examined, injected at 200 μg per day intraperitoneally on fat mass in 3-month-old wild-type male and female C57BL/6J mice, which were either pair-fed on, or allowed ad libitum access to, a high-fat diet. Body weight increased over 8 weeks with near equal food intake in both male and female mice, with no significant difference in either sex between antibody- and goat IgG-treated mice (FIG. 4A). Quantitative NMR (qNMR) showed a reduction in body fat and an increase in lean mass/total mass (LM/TM) ratio in mice treated with antibody (FIG. 4B). Data were reproduced using qNMR, dual energy X-ray absorptiometry (DXA) and tissue weight measurements at 7 weeks (FIG. 3A-C). DXA also showed a significant increase in bone mineral density at both 4 and 7 weeks (FIG. 3B). Micro-computed tomography (micro-CT) of distinct thoracoabdominal white adipose tissue (WAT) compartments revealed substantial decreases in visceral and subcutaneous adiposity in antibody-treated mice (FIG. 4C). Specifically, total (TFV), subcutaneous (SFV) and visceral fat volume (VFV) were all significantly reduced (P≤0.05) in antibody-treated mice than in IgG-treated mice (FIG. 4C). No difference was observed in interscapular brown adipose tissue (BAT) by weight (FIG. 3C). Similar results were obtained using 8-month-old mice (FIG. 5) and under thermoneutral conditions at 30° C. (FIG. 3D).

The hypotheses that Fshr-deficient mice would phenocopy the effect of antibody treatment and that the antiadiposity actions of the polyclonal FSH antibody would be attenuated in mice with a genetic Fshr deficiency was tested. IgG-treated male Fshr+/− mice showed reductions in total mass and fat mass measured by qNMR, and in TFV, SFV and VFV measured by micro-CT (FIG. 6A, B). There was no further reduction in any parameter when the Fshr+/− mice were treated with the FSH antibody (FIG. 6A, B), proving that the antibody acts by suppressing the FSH signalling axis in vivo. Furthermore, the fact that haploinsufficient Fshr+/− mice phenocopied the anti-adiposity actions of the FSH antibody illustrates that FSH is a dominant physiological regulator of fat mass.

In antibody-treated mice, indirect calorimetry using metabolic cages showed increases in energy expenditure and oxygen consumption ($VO_2$), which were accompanied by increased physical activity parameters, including X-beam breaks and walking distance and speed. Independently performed penalized spline (p-Spline) regression showed that physical activity, mainly consisting of walking (not running), did not contribute to the increased energy expenditure (TABLES 6, 7, 8 below). Specifically, energy expenditure due to physical activity (A-EE (PA)) did not differ between antibody and IgG-treated groups. Instead, mice displayed an elevated daytime resting energy expenditure (R-EE), which corresponded to the noted trend (P=0.08) in resting metabolic rate (RMR) on p-Spline regression. The latter findings together suggest that antibody-induced beiging, rather than physical activity, contributes to thermogenesis and leanness. This is fully consistent with antibody-induced increases in Ucp1 RNA and protein in both BAT and WAT.

TABLE 6

Indirect Calorimetry (24 Hour)

| | Indirect Calorimetry | | |
|---|---|---|---|
| | IgG | Anti-FSH Ab | P-value |
| Thermogenesis Parameters | | | |
| $VO_2$ (mL/min) | 2.14 ± 0.04 | 2.41 ± 0.08 | 0.03 |
| EE (Kcal/hr) | 0.61 ± 0.01 | 0.68 ± 0.02 | 0.03 |
| R-EE (Kcal/30 min) | 0.55 ± 0.03 | 0.58 ± 0.01 | NS |
| A-EE (Kcal/15 min) | 0.74 ± 0.02 | 0.80 ± 0.04 | NS |
| RQ (%) | 0.72 ± 0.02 | 0.68 ± 0.002 | NS |
| Activity Parameters | | | |
| Xbreaks (×10,000) | 1.37 ± 0.24 | 2.34 ± 0.10 | 0.01 |
| Ybreaks (×10,000) | 1.97 ± 0.18 | 2.28 ± 0.22 | NS |
| Zbreaks (×10,000) | 1.19 ± 0.53 | 0.59 ± 0.10 | NS |
| Wheel Meters (m, ×1000) | 2.84 ± 0.43 | 3.97 ± 0.34 | NS |
| Wheel Speed (m/s) | 0.17 ± 0.01 | 0.18 ± 0.01 | NS |
| Ped Meters (m) | 129 ± 9.70 | 189 ± 15.9 | 0.02 |
| Ped Speed (cm/s) | 1.24 ± 0.04 | 1.49 ± 0.06 | 0.01 |
| Food Intake | | | |
| Food (g) | 0.89 ± 0.34 | 1.60 ± 0.41 | NS |
| p-Spline Regression | | | |
| EE (Kcal/hr) | 0.61 ± 0.01 | 0.68 ± 0.02 | 0.03 |
| RMR (Kcal/hr) | 0.47 ± 0.02 | 0.52 ± 0.02 | NS |
| [A-EE (PA)] (Kcal/hr) | 0.14 ± 0.01 | 0.16 ± 0.02 | NS |

TABLE 7

Indirect Calorimetry (Day)

| | Indirect Calorimetry | | |
|---|---|---|---|
| | IgG | Anti-FSH Ab | P-value |
| Thermogenesis Parameters | | | |
| $VO_2$ (mL/min) | 1.86 ± 0.07 | 2.14 ± 0.11 | 0.08 |
| EE (Kcal/hr) | 0.53 ± 0.02 | 0.60 ± 0.03 | NS |
| R-EE (Kcal/30 min) | 0.52 ± 0.01 | 0.60 ± 0.02 | 0.03 |
| R-33 (Kca/15 min) | 0.71 ± 0.03 | 0.75 ± 0.05 | NS |
| RQ (%) | 0.71 ± 0.02 | 0.68 ± 0.002 | NS |
| Activity Parameters | | | |
| Xbreaks (×10,000) | 0.37 ± 0.08 | 0.88 ± 0.06 | <0.01 |
| Ybreaks (×10,000) | 0.59 ± 0.09 | 0.83 ± 0.08 | 0.09 |
| Zbreaks (×10,000) | 0.11 ± 0.03 | 0.15 ± 0.03 | NS |
| Wheel Meters (m, ×1000) | 0.07 ± 0.03 | 0.71 ± 0.31 | NS |
| Wheel Speed (m/s) | 0.14 ± 0.01 | 0.16 ± 0.02 | NS |
| Ped Meters (m) | 27.5 ± 3.82 | 61.3 ± 8.76 | 0.01 |
| Ped Speed (cm/s) | 1.17 ± 0.07 | 1.53 ± 0.14 | 0.053 |
| Food Intake | | | |
| Food (g) | 0.11 ± 0.02 | 0.39 ± 0.10 | 0.03 |
| p-Spline Regression | | | |
| EE (Kcal/hr) | 0.53 ± 0.02 | 0.60 ± 0.03 | NS |
| RMR (Kcal/hr) | 0.46 ± 0.02 | 0.51 ± 0.02 | 0.08 |
| [A-EE (PA)] (Kcal/hr) | 0.07 ± 0.03 | 0.09 ± 0.02 | NS |

TABLE 8

Indirect Calorimetry (Night)

| | Indirect Calorimetry | | |
|---|---|---|---|
| | IgG | Anti-FSH Ab | P-value |
| Thermogenesis Parameters | | | |
| $VO_2$ (mL/min) | 2.42 ± 0.07 | 2.69 ± 0.06 | 0.03 |
| EE (Kcal/hr) | 0.69 ± 0.02 | 0.76 ± 0.02 | 0.03 |
| R-EE (Kcal/30 min) | 0.57 ± 0.05 | 0.55 ± 0.02 | NS |
| R-EE (Kcal/15 min) | 0.77 ± 0.02 | 0.85 ± 0.04 | NS |
| RQ (%) | 0.73 ± 0.03 | 0.69 ± 0.002 | NS |
| Activity Parameters | | | |
| Xbreaks (×10,000) | 1.00 ± 0.18 | 1.47 ± 0.13 | 0.08 |
| Ybreaks (×10,000) | 1.38 ± 0.11 | 1.45 ± 0.19 | NS |
| Zbreaks (×10,000) | 1.08 ± 0.51 | 0.44 ± 0.08 | NS |
| Wheel Meters (m, ×1000) | 2.77 ± 0.53 | 3.26 ± 0.19 | NS |
| Wheel Speed (m/s) | 0.20 ± 0.01 | 0.19 ± 0.01 | NS |
| Ped Meters (m) | 101 ± 9.99 | 128 ± 18.0 | NS |
| Ped Speed (cm/s) | 1.31 ± 0.02 | 1.44 ± 0.05 | 0.06 |
| Food Intake | | | |
| Food (g) | 0.79 ± 0.32 | 1.21 ± 0.31 | NS |
| p-Spline Regression | | | |
| EE (Kcal/hr) | 0.69 ± 0.02 | 0.76 ± 0.31 | 0.02 |
| RMR (Kcal/hr) | 0.48 ± 0.02 | 0.53 ± 0.02 | NS |
| [A-EE (PA)] (Kcal/hr) | 0.48 ± 0.02 | 0.22 ± 0.02 | NS |

Known links of physical activity with endocrine mediators of beiging or leanness, which can also affect bone mass, were explored. Groups of mice fed on a high-fat diet were injected with polyclonal anti-FSH antibody or IgG (200 μg per mouse per day) for 7 weeks, after which half of each group received the tyrosine hydroxylase inhibitor α-methyl-p-tyrosine (AMPT). Plasma noradrenaline levels did not differ significantly between the IgG- and antibody-treated groups either without or following AMPT treatment (FIG. 3E). Likewise, plasma irisin levels were indistinguishable between IgG- and anti-FSH antibody-treated mice (FIG. 3F), and meteorin-like (Metrnl) remained undetectable in the plasma of both groups.

Both glucose tolerance testing (GTT) and insulin tolerance testing (ITT) showed no improvements after antibody treatment (FIG. 3G, H). Consistent with this, plasma C-peptide, adiponectin and leptin levels were unchanged (FIG. 3I). Circulating total cholesterol and free fatty acids were also unchanged, but there was a marginal increase in plasma triglycerides in antibody-treated mice (FIG. 3J). Antibody treatment also did not affect serum oestradiol (E2) levels (FIG. 3K).

Anti-FSH Antibody Reduces Adiposity in Ovariectomized Mice:

Clinical phenotype associated of perimenopausal transition has been documented in rodents post-ovariectomy, as well as in chronic hypooestrogenaemic models, such as in female Esr1 –/– (also known as Era –/–), Cyp19a1 (also known as aromatase –/–) and Fshr–/– mice, although in this Example, female Fshr –/– mice are not obese. Although genetic Fshr deficiency does not seem to protect against the pro-adiposity effects of severe chronic hypo-oestrogenaemia in female mice, it was investigated whether acute suppression of FSH by anti-FSH antibody can, through parallel mechanisms, not only attenuate bone loss, but also reduce body fat and improve energy homeostasis. Clinically, this is particularly important during the late perimenopause, when the onset of central adiposity is accompanied by relatively stable oestrogen and increasing FSH levels.

Figure 7:
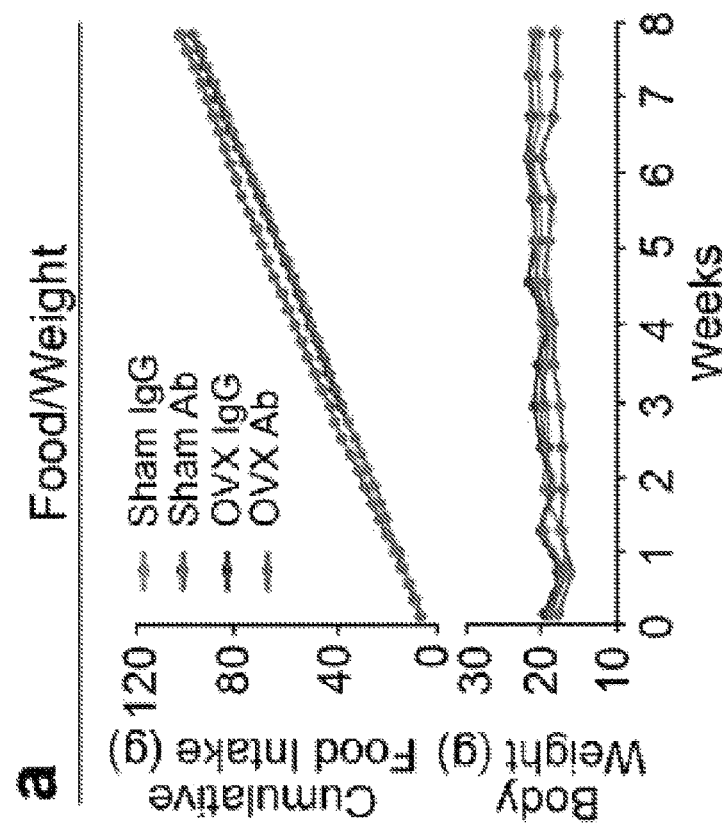
FIGS. 7A, 7B, and 7C represent effects of anti-FSH antibody in ovariectomized mice. Ovariectomized or sham-operated mice on normal chow were injected with anti-FSH antibody or goat IgG (200 and 400 μg per mouse per day to sham-operated and ovariectomized mice, respectively).
Figure 7:
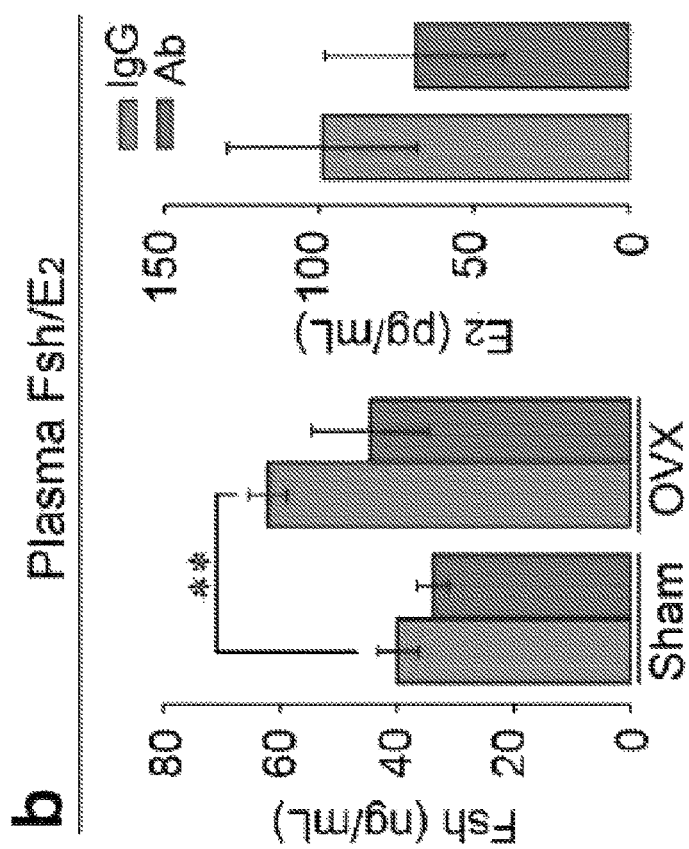
Figure 7:
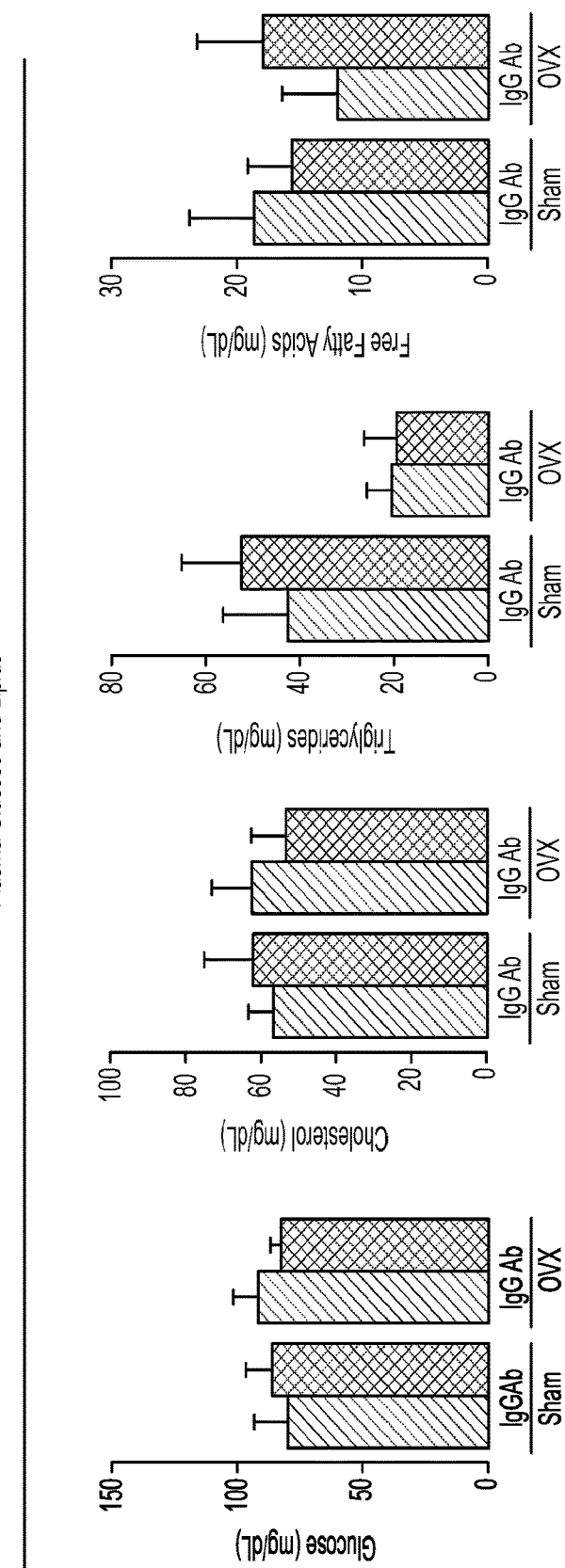

Female mice were pair-fed with normal chow, so that their food intake was near-identical over 8 weeks of treatment with anti-FSH antibody or IgG given intraperitoneally after an ovariectomy or a sham operation. Unlike mice fed on a high-fat diet (FIG. 4A), these mice on normal chow did not show an increase in total body weight over time (FIG. 7A). However, antibody-treated, sham-operated mice showed a reduction in body weight compared to IgG-injected mice (see Source Data for FIG. 7A; compare with FIG. 9A). Quantitative NMR showed a reduction in fat mass and increase in LM/TM after antibody treatment in both the sham-operated and ovariectomized groups (FIG. 8A). Antibody treatment also reduced TFV, VFV and SFV in both groups (FIG. 8B). Furthermore, osmium micro-CT revealed a decrease in marrow adipose volume in antibody-treated mice (FIG. 8C). Ovariectomy resulted in an expected increase in plasma FSH levels (FIG. 7B). To ensure that FSH was blocked effectively despite these increased levels, 200 or 400 µg per mouse per day of antibody was used to treat the ovariectomy group, as opposed to 100 µg per mouse per day for the sham-operated group. Notably, although FSH was bound to antibody (FIG. 2A), total plasma FSH levels (measured by ELISA) were not significantly different between antibody- and IgG-treated mice (FIG. 7B). Additionally, while serum oestrogen levels trended to be lower in the antibody-treated group, there was no significant difference from the IgG-treated group (FIGS. 3K and 7B).

Figure 8:
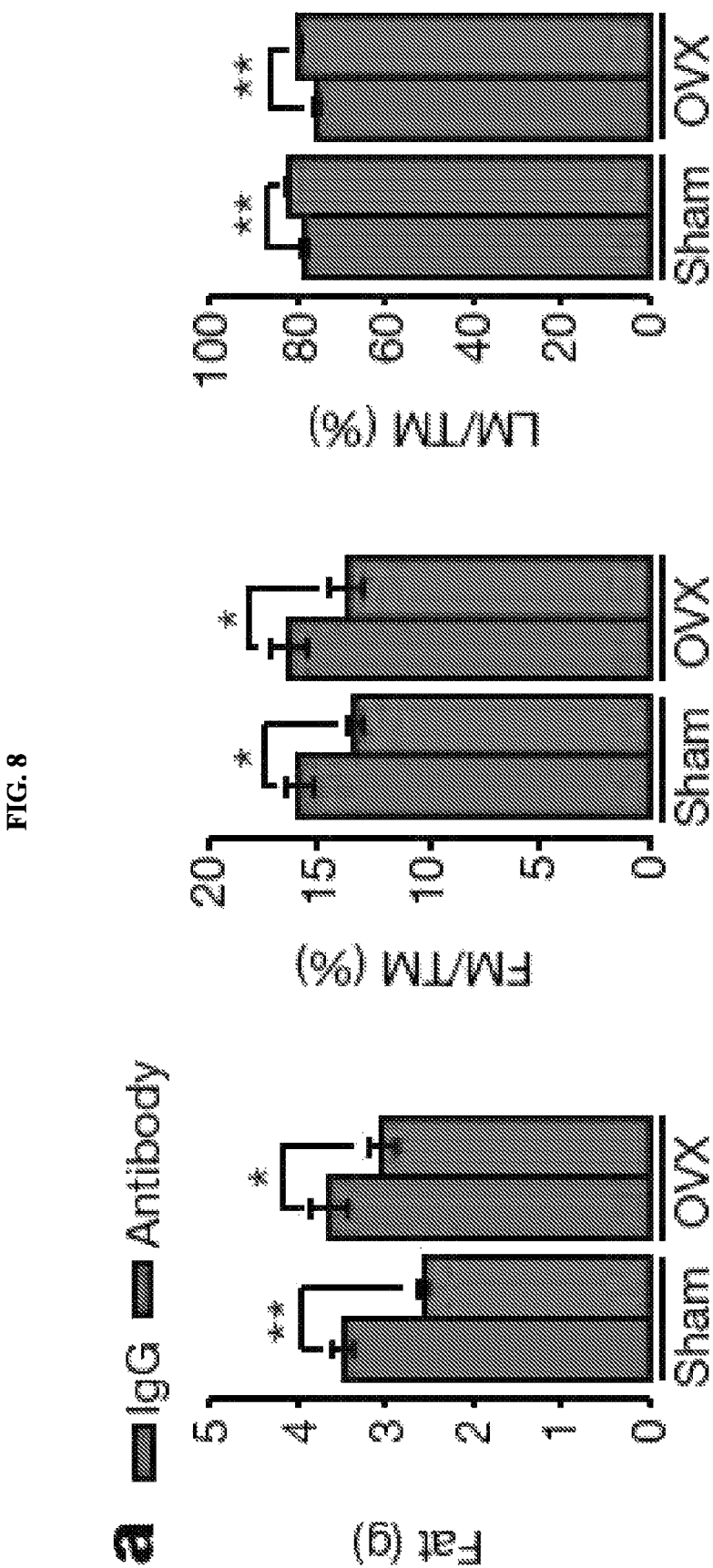
FIGS. 8A, 8B, and 8C represent that anti-FSH antibody reduces adiposity in ovariectomized mice. Ovariectomized (OVX) or sham-operated mice on normal chow injected with anti-FSH antibody or goat IgG (200-400 μg per day) for 8 weeks.
Figure 8:
Figure 8:
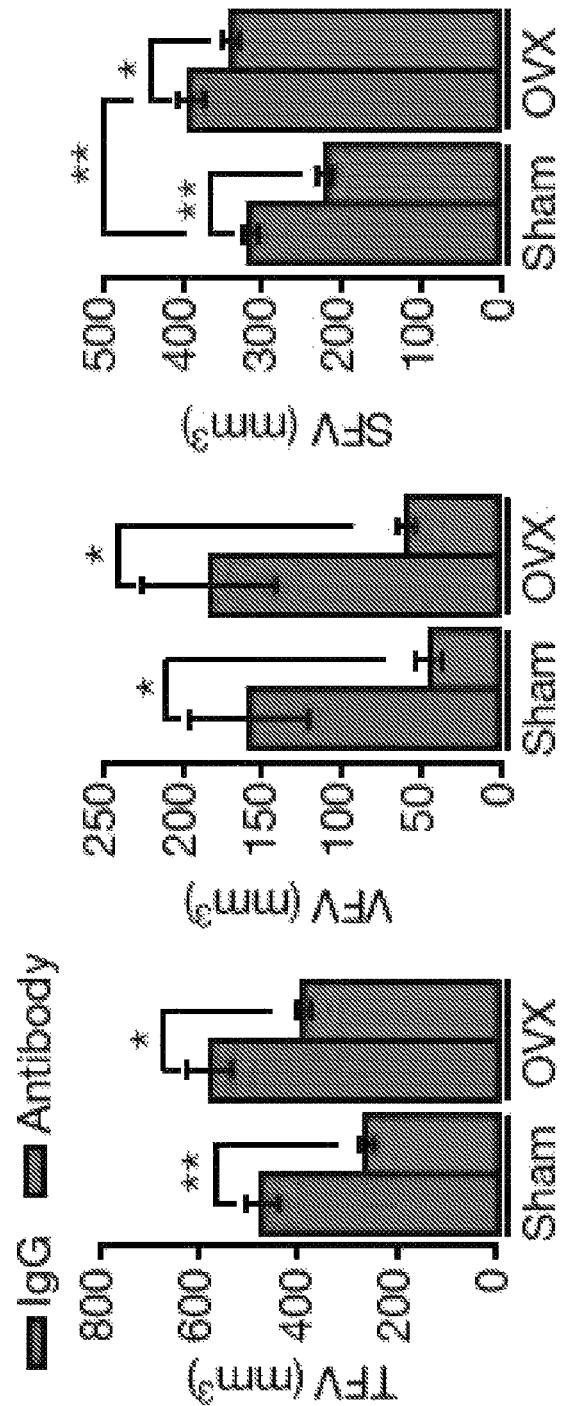
Figure 8:
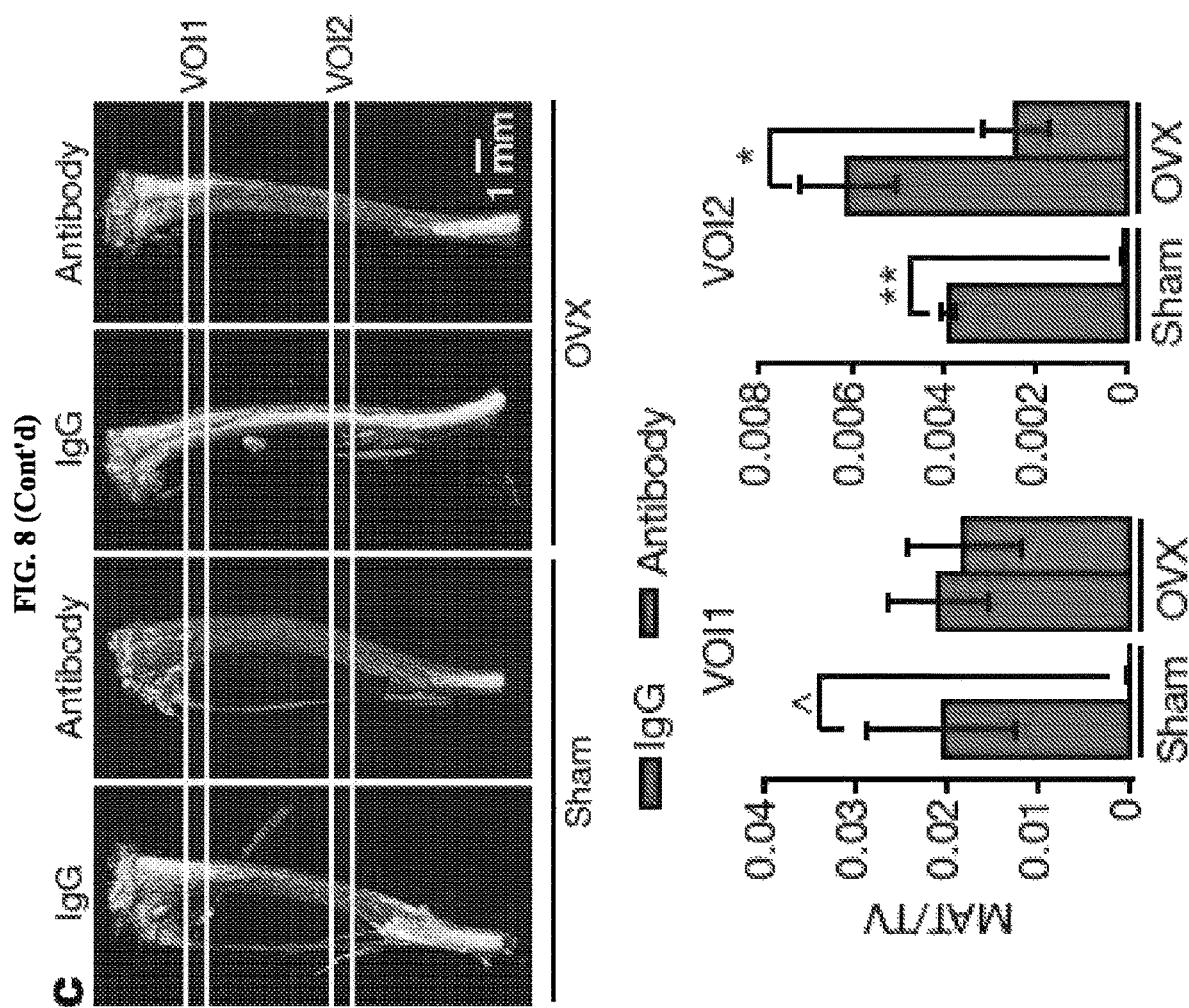
Figure 9:
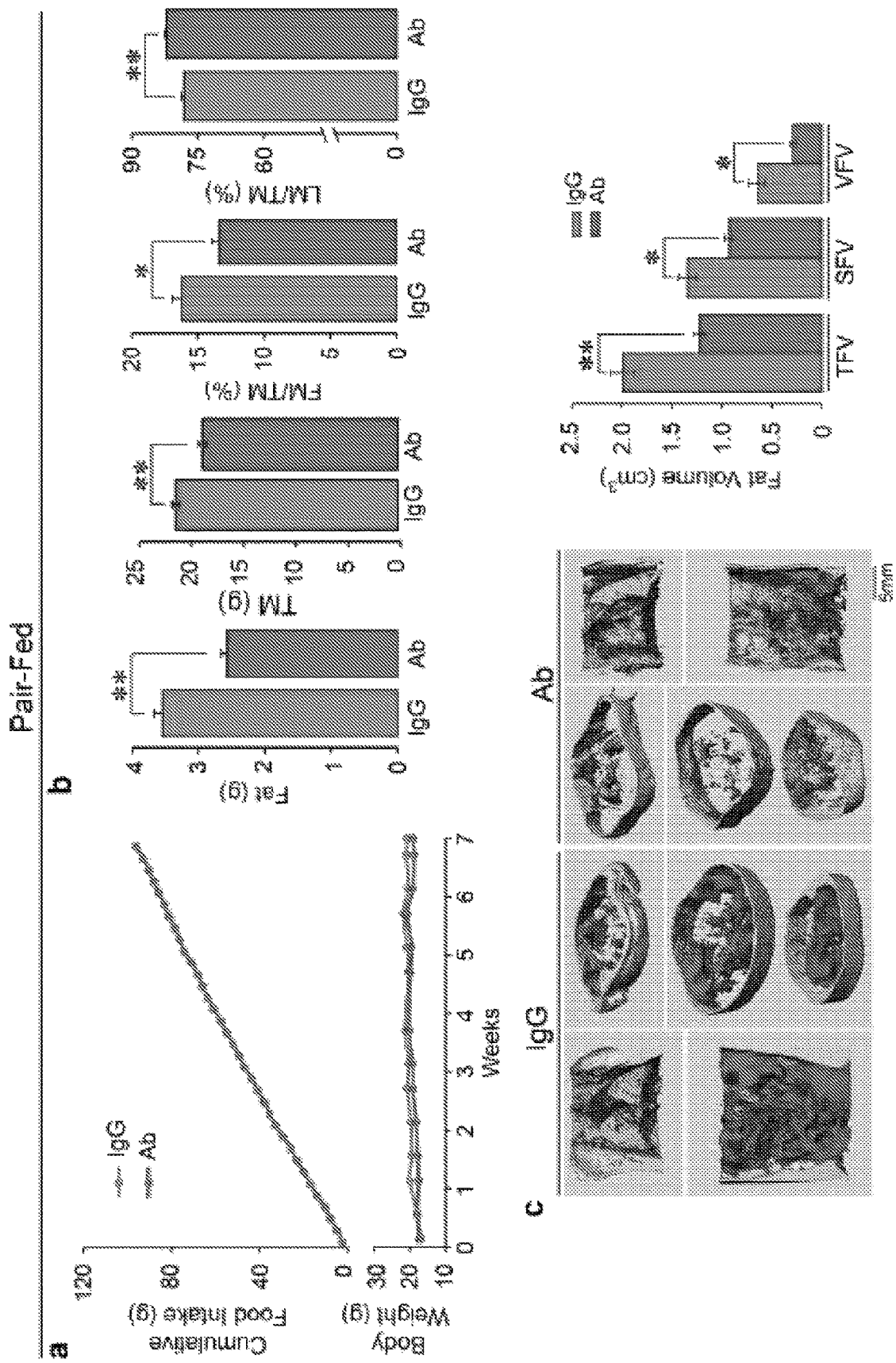
FIGS. 9A, 9B, 9C, 9D, 9E, and 9F represent that anti-FSH antibody reduces body fat in mice fed on normal chow. Three-month-old C56BL/6J female mice were either pair-fed (FIGS. 9A, 9B and 9C) or fed ad libitum (FIGS. 9D, 9E and 9F) with normal chow and injected with anti-FSH antibody or IgG (100 μg per mouse per day) for 7 and 5 weeks, respectively. For pair-feeding, the amount of chow consumed ad libitum by the IgG group was given to the antibody-treated group. For ad libitum feeding, the antibody-treated group was allowed ad libitum access to food and the same amount of chow was given to the IgG group, with the leftover chow measured to determine food intake of the IgG group. A significant increase in food intake by antibody-treated mice was noted in the ad libitum feeding protocol. Nonetheless, as with mice on a high fat diet, in either feeding protocol, antibody treatment caused a substantial decrease in total mass (TM), fat mass (FM) and FM/TM and increase in LM/TM on quantitative NMR in mice that were pair-fed. Body weight was also reduced. However, whereas antibody-treated mice consumed substantially more chow than IgG-injected mice, they showed decreases in FM and FM/TM, but did not show a reduction in TM or body weight. Micro-CT showed profound decreases in thoracoabdominal fat, visualized in representative coronal and transverse sections, and upon quantification of TFV, SFV and VFV in both groups.
Figure 9:
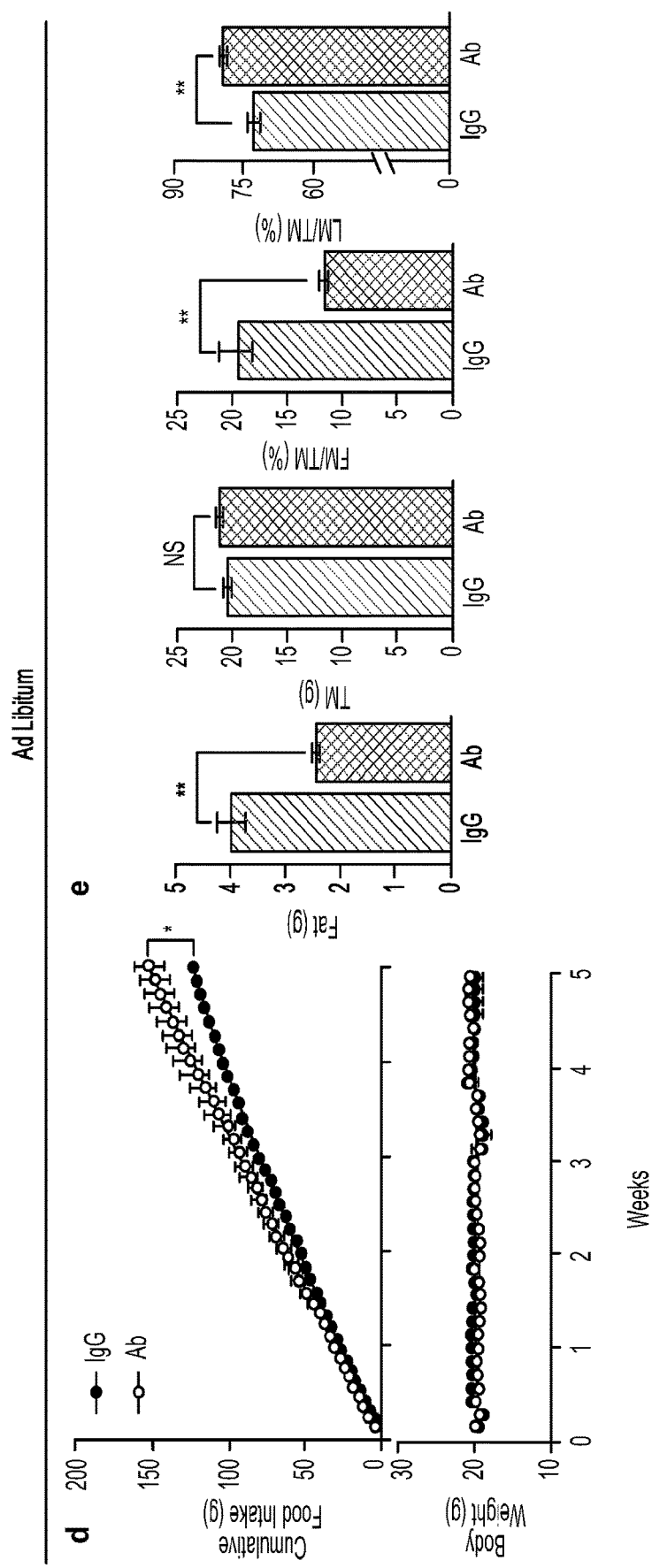
Figure 9:
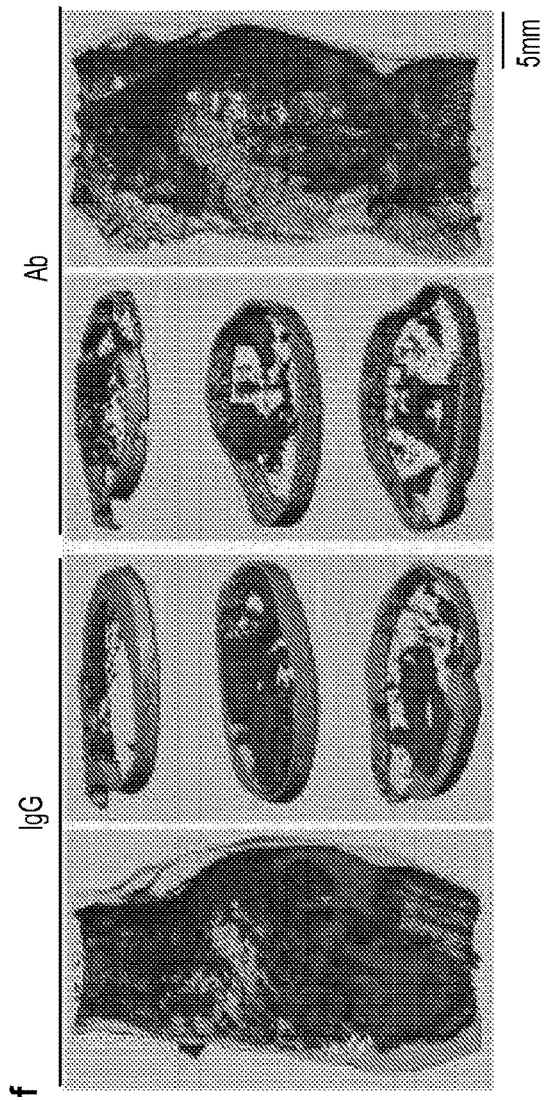
Figure 9:
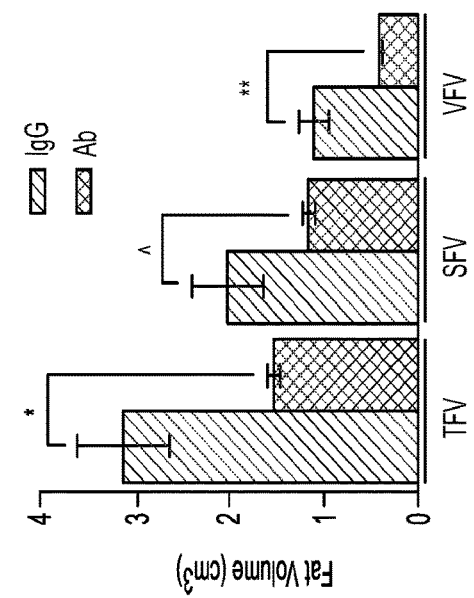

Surprisingly, sham-operated mice and ovariectomized mice were equally responsive to antibody treatment (FIG. 8). The study was therefore repeated using 3-month-old C57BL/6J mice that were either pair-fed or given normal chow ad libitum (see FIG. 9). Mice pair-fed on chow treated with antibody showed reduced total body weight at various time points (see Source Data for FIG. 7A, 9A). Antibody treatment also reduced fat mass and FM/TM, as well as abdominal TFV, SFV and VFV (FIG. 9B, 9C). By contrast, when allowed ad libitum access to chow, despite their increased food intake, antibody-injected mice did not show a decrease in total body weight, but displayed similar reductions in fat mass and abdominal TFV, SFV and VFV (FIGS. 9D, 9E, and 9F and Source Data).

Indirect calorimetry showed that anti-FSH antibody enhanced active energy expenditure and reduced respiratory quotient in sham-operated or ovariectomized mice (TABLES 9, 10 below). These thermogenic responses were not associated with significant increases in parameters of physical activity; instead, there was an unexplained decrease in walking distance in the ovariectomized antibody-treated group. Likewise, a marginal increase in active energy expenditure was noted in antibody-treated wild-type mice on normal chow with no change in physical activity (TABLE 11 below). Overall, physical activity did not contribute to antibody-induced thermogenesis, or indeed, leanness in ovariectomized or wild-type mice on normal chow. There were no differences in plasma levels of glucose, cholesterol, triglyceride or free fatty acids between IgG- and antibody-treated groups on normal chow (FIG. 7C).

TABLE 9

Indirect Calorimetry (Sham)

| | Indirect Calorimetry | | |
|---|---|---|---|
| | IgG | Anti-FSH Ab | P-value |
| Thermogenesis Parameters | | | |
| RQ (%) | 0.77 ± 0.003 | 0.72 ± 0.02 | 0.001 |
| R-EE (Kcal/30 min) | 0.41 ± 0.02 | 0.45 ± 0.02 | NS |
| A-EE (Kcal/15 min) | 0.59 ± 0.04 | 0.68 ± 0.02 | NS |
| Activity Parameters | | | |
| Wheel Meters (m, ×1000) | 5.73 ± 1.62 | 8.12 ± 0.39 | NS |
| Wheel Speed (m/s) | 0.23 ± 0.03 | 0.25 ± 0.01 | NS |
| Ped Meters (m) | 124 ± 12.0 | 150 ± 18.4 | NS |
| Ped Speed (cm/s) | 1.41 ± 0.08 | 1.54 ± 0.07 | NS |
| Food Intake | | | |
| Food (g) | 3.21 ± 0.31 | 3.41 ± 0.55 | NS |

TABLE 10

Indirect Calorimetry (OVX)

| | Indirect Calorimetry | | |
|---|---|---|---|
| | IgG | Anti-FSH Ab | P-value |
| Thermogenesis Parameters | | | |
| RQ (%) | 0.77 ± 0.01 | 0.77 ± 0.01 | 0.04 |
| R-EE (Kcal/30 min) | 0.37 ± 0.02 | 0.40 ± 0.01 | NS |
| A-EE (Kcal/15 min) | 0.53 ± 0.02 | 0.59 ± 0.01 | 0.04 |
| Activity Parameters | | | |
| Wheel Meters (m, ×1000) | 1.84 ± 0.47 | 2.80 ± 0.74 | NS |
| Wheel Speed (m/s) | 0.19 ± 0.01 | 0.19 ± 0.01 | NS |
| Ped Meters (m) | 151 ± 7.59 | 115 ± 9.71 | 0.03 |
| Ped Speed (cm/s) | 1.46 ± 0.06 | 1.33 ± 0.03 | NS |
| Food Intake | | | |
| Food (g) | 3.57 ± 0.64 | 2.92 ± 0.11 | NS |

TABLE 11

Indirect Calorimetry (metabolic cages)

| | Indirect Calorimetry | | |
|---|---|---|---|
| | IgG | Anti-FSH Ab | P-value |
| A-EE (Kcal/15 min) | 0.66 ± 0.02 | 0.77 ± 0.04 | 0.057 |
| Wheel Meters (m, ×1000) | 3.75 ± 0.28 | 3.45 ± 0.48 | NS |
| Wheel Speed (m/s) | 0.21 ± 0.01 | 0.19 ± 0.01 | NS |
| Ped Meters (m) | 145 ± 35.8 | 126 ± 23.7 | NS |

TABLE 11-continued

Indirect Calorimetry (metabolic cages)

| | Indirect Calorimetry | | |
|---|---|---|---|
| | IgG | Anti-FSH Ab | P-value |
| Ped Speed (cm/s) | 1.34 ± 0.01 | 1.41 ± 0.0004 | NS |
| Food (g) | 2.41 ± 0.82 | 3.22 ± 1.19 | NS |

Blocking FSH Action on Adipocyte FSHRs Induces Ucp1 Expression

Figure 10:
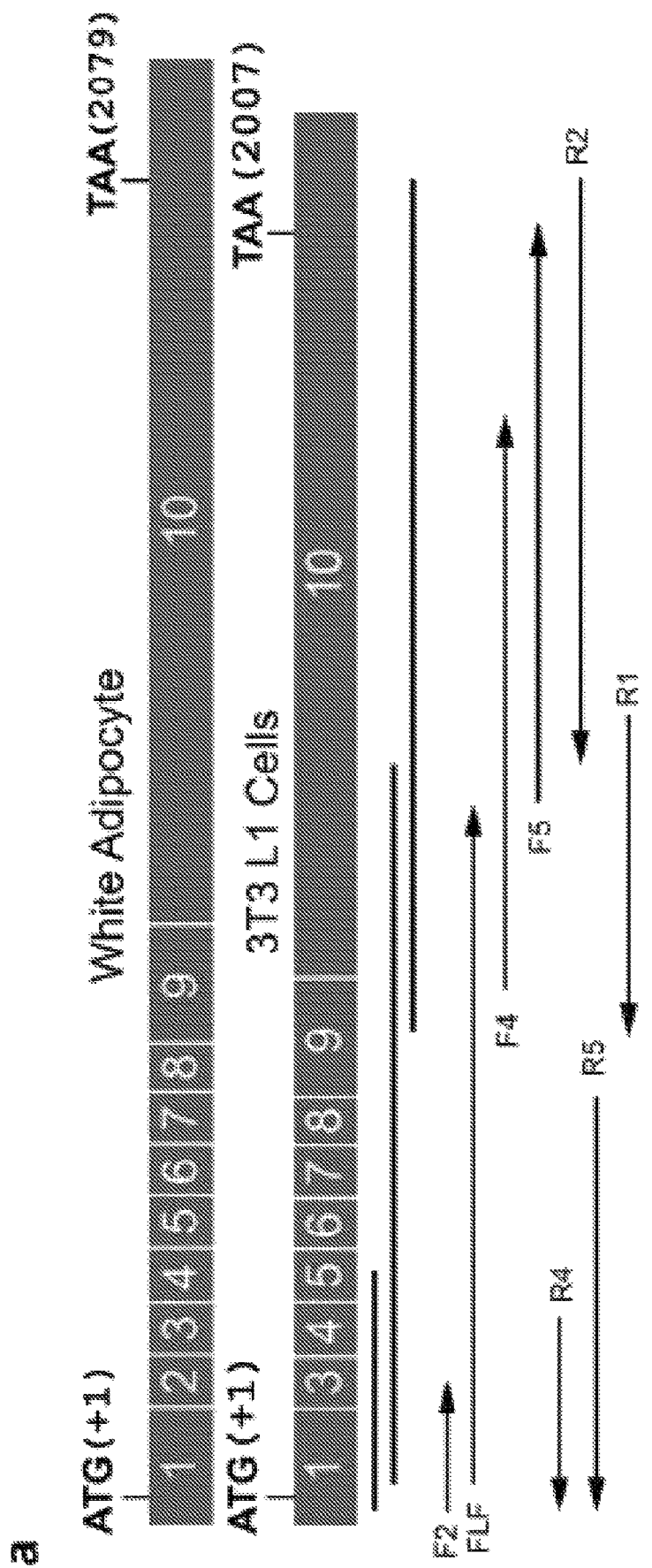
FIGS. 10A and 10B represent Sanger sequencing confirms expression of FSHR on adipocytes.
Figure 10:
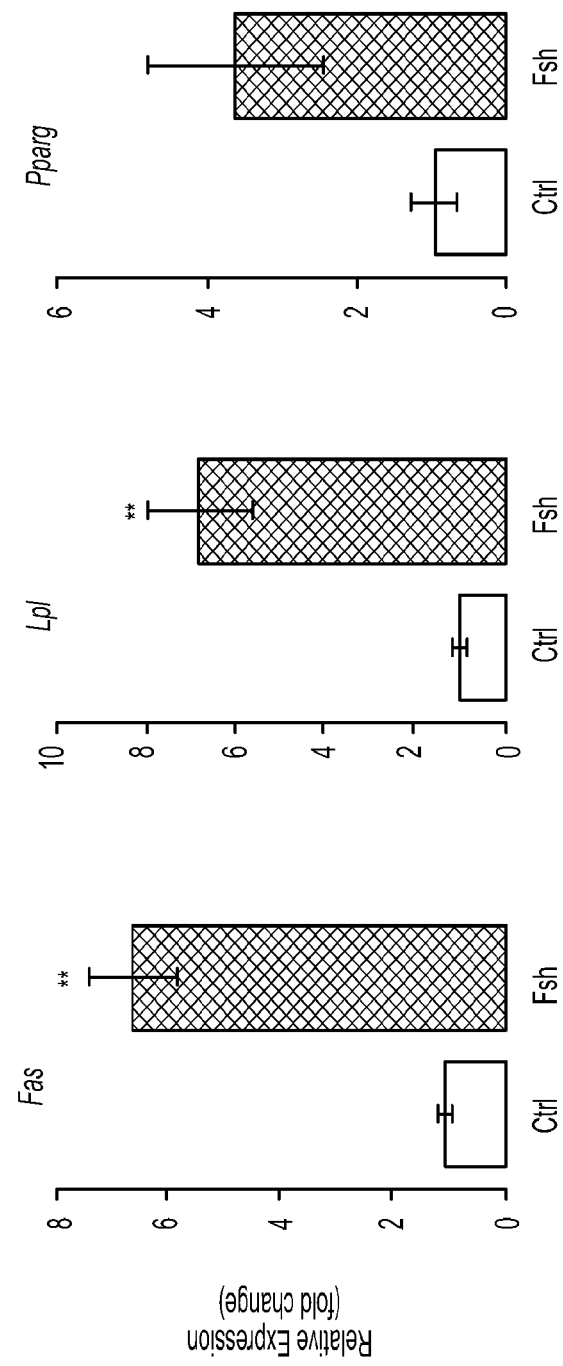
Figure 11:
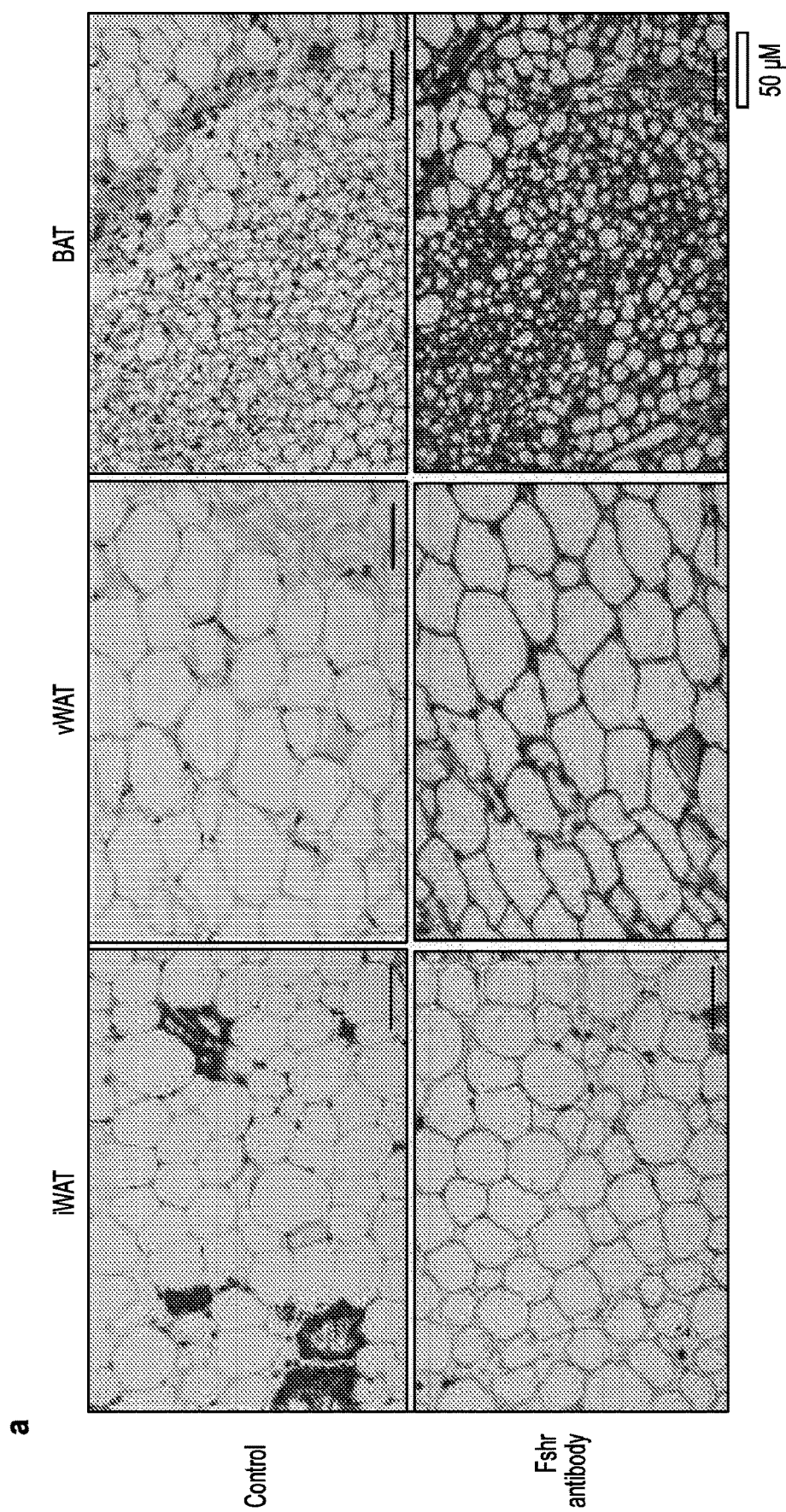
FIGS. 11A, 11B, 11C, 11D, and 11E represent that treatment with anti-FSH antibody blocks FSH-FSHR interaction to activate Ucp1.
Figure 11:
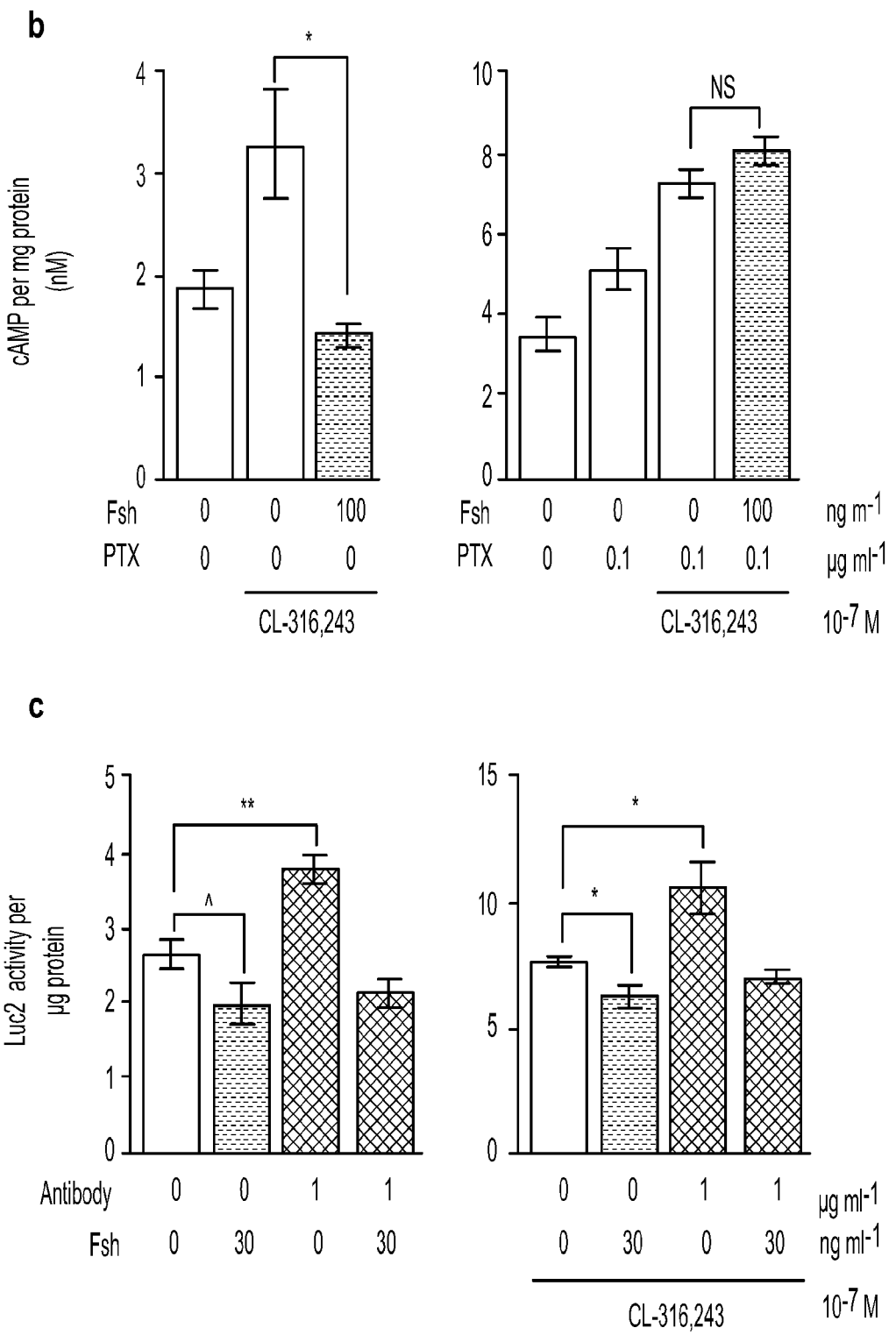
Figure 11:
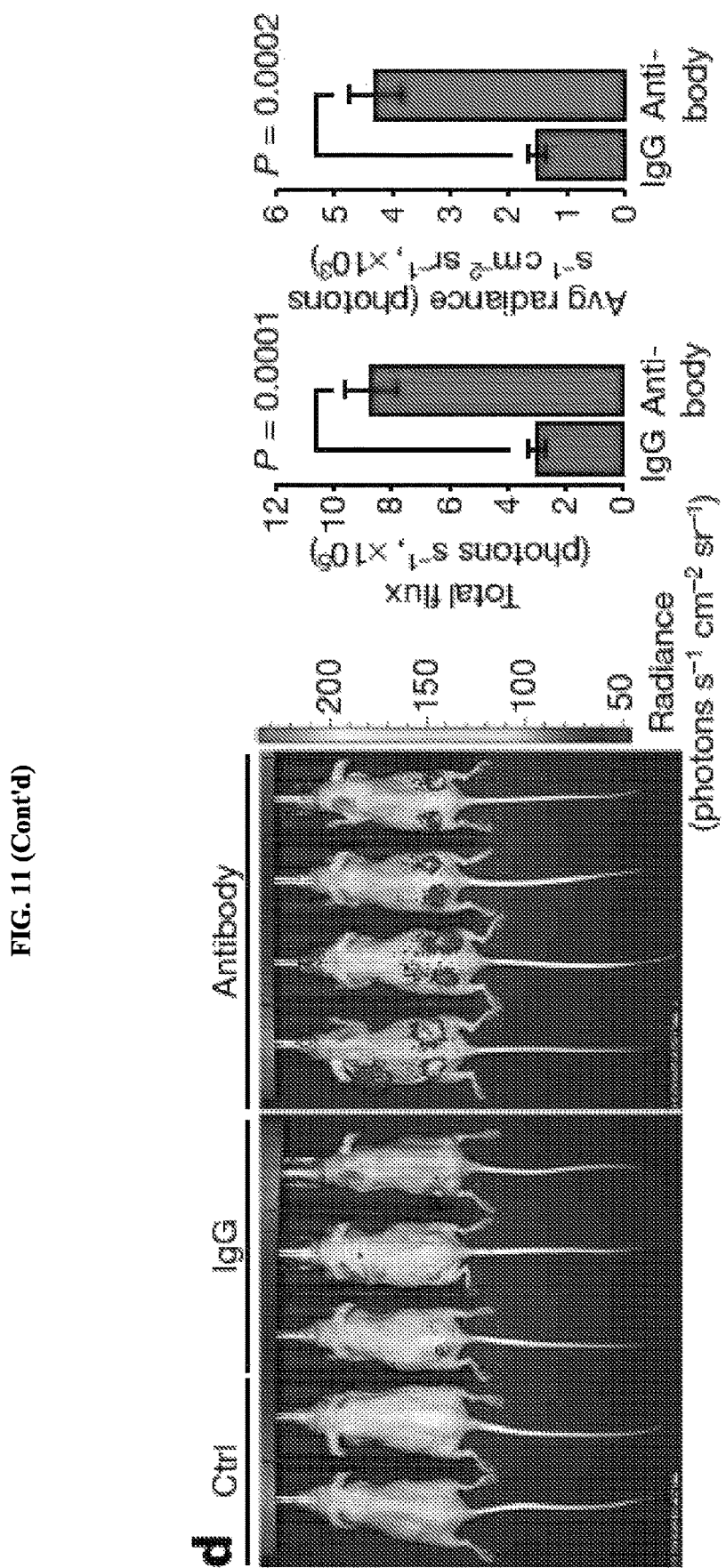
Figure 11:
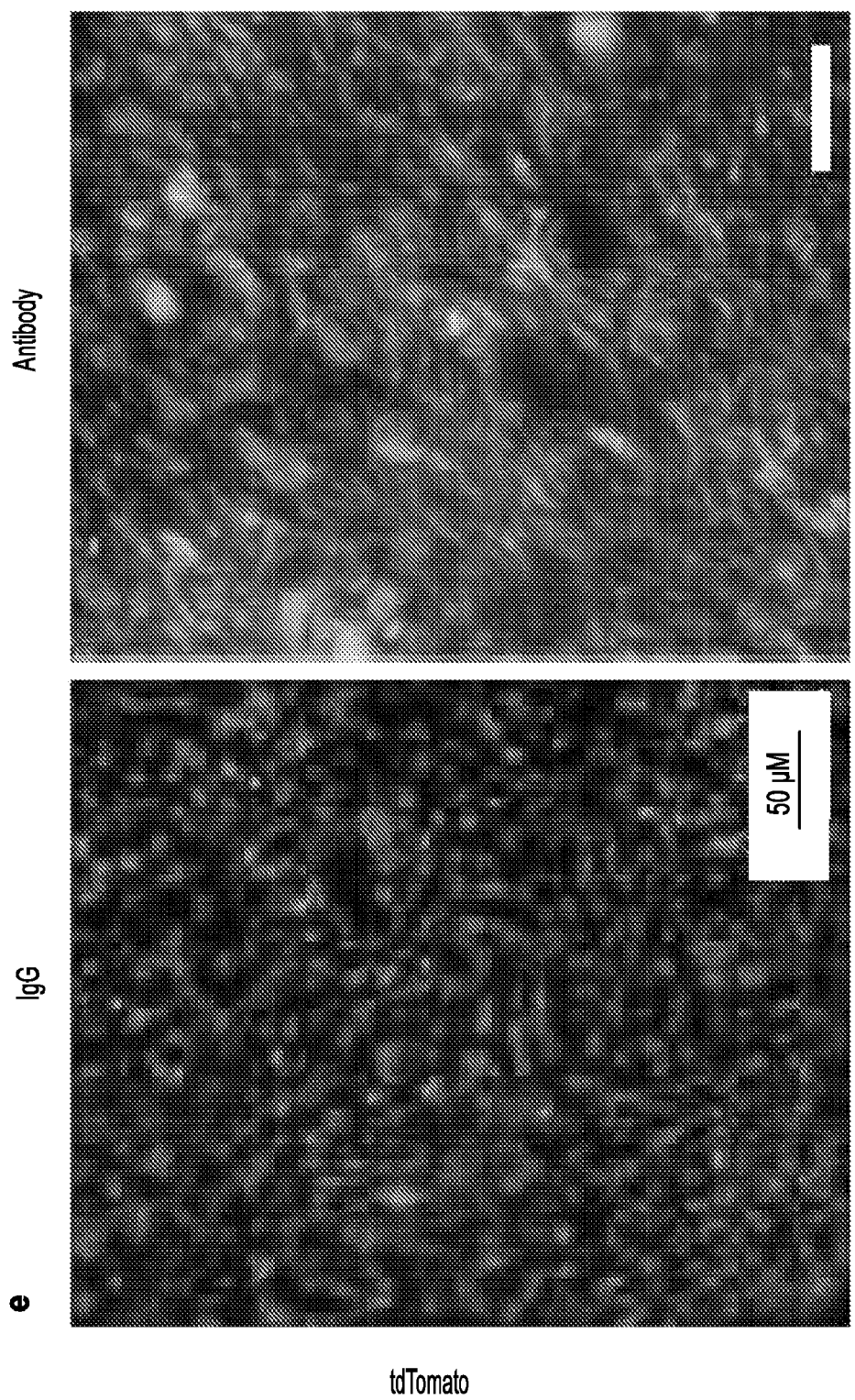

FSHR cDNA and protein have previously been identified in fat tissue and adipocytes, as well as on osteoclasts and mesenchymal stem cells. Full-length FSHR cDNA (see below, SEQ ID NO: 30) was Sanger-sequenced (see below, SEQ ID NO: 31) from primary mouse mesenchymal stem cells derived from ear lobes (MSC-ad) and 3T3.L1 cells (FIG. 10A). The FSHR protein, confirmed through immunostaining of inguinal and visceral WAT and BAT (FIG. 11A), is signalling efficient and functional in its ability to inhibit cAMP (FIG. 11B) and to stimulate the lipogenic genes Fas and Lpl (FIG. 10B). However, in contrast to its coupling with Gs proteins in ovarian follicular cells, the adipocyte FSHR couples to Gi proteins. Thus, in differentiated 3T3.L1 adipocytes, whereas Fsh abrogated the increase in cAMP triggered by the Arb3 agonist CL-316, 243, this inhibition was reversed in the presence of the Gi inhibitor pertussis toxin (FIG. 11B).

As the increase in cAMP induced by Arb3 signalling stimulates Ucp1, it was investigated whether FSH inhibited this induction of Ucp1 using Thermo cells (FIG. 2D). Experiments in the presence of serum, which contains FSH at 15-40 ng ml$^{-1}$, showed that the antibody (1 μg ml$^{-1}$), induced Ucp1 expression without the addition of FSH, irrespective of the presence of CL-316,243 (FIG. 11C). This stimulation was reversed by the further addition of FSH (30 ng ml$^{-1}$), establishing FSH specificity (FIG. 11C, compare with FIG. 2D). Thermo cells were implanted into both flanks of 3-month-old nu/nu mice and injected IgG or anti-FSH antibody (200 μg per mouse per day) for 8 weeks. A marked increase in Luc2 radiance was noted upon injection of d-luciferin (FIG. 11D). For confirmation, tdTomato fluorescence was examined (red) in frozen sections of inguinal WAT (iWAT). Consistent with the increase in Luc2 radiance, antibody-treated mice showed a marked increase in tdTomato expression (FIG. 11E). Together, the data indicates that anti-FSH antibody, by blocking the action of FSH on FSHR, activates Ucp1.

FSHR cDNA Nucleotide Sequence:
(SEQ ID NO: 30)
TGAGCAGGCAGAAAGCAGGTGGATGGATAAAATAAGCATGGCCTTGCTC

CTGGTCTCCTTGCTGGCATTCTTGGGCTCGGGATCTGGATGTCATCACT

GGCTGTGTCATTGCTCTAACAGGGTCTTCCTCTGCCAAGATAGCAAGGT

GACCGAGATTCCGCCCGACCTCCCCCGGAACGCCATTGAAGT<u>GAGATTT</u>

<u>GTGCTCACCAAGCTTCGAGTCATTCCAAAAGGATCATTTTCTGGATTTG</u>

<u>GGGACCTGGAGAAAATA</u>GAGATCTCTCAGAATGATGTCTTGGAGGTAAT

AGAGGCAGATGTGTTCTCCAACCTACCCAACTTGCATGAAATTAGGATT

GAAAAGGCTAACAATCTGCTGTACATCAACCCTGAGGCCTTCCAGAATC

TTCCCAGTCTCCGATATCTGTTAATATCCAACACAGGCATTAAACACTT

GCCAGCCTTTCACAAGATCCAGTCTCTCCAAAAGGTTTTATTAGACATT

CAAGATAACATAAACATCCACATCATTGCCAGGAACTCCTTCATGGGAC

TGAGCTTTGAAAGTGTAATTCTATGGCTGAATAAGAATGGGATTCAAGA

AATACACAACTGTGCATTCAACGGAACCCAGCTAGATGAACTGAATCTA

AGCGATAACAATAATTTGGAAGAATTGCCTGATGATGTTTTCCAGGGAG

CCTCTGGGCCAGTCGTTTTAGACATCTCAAGGACAAAGGTCTATTCCCT

GCCCAACCATGGCTTAGAAAATCTGAAGAAGTTGAGGGCCAGGTCAACA

TACCGCTTGAAAAAGCTCCCTAGTCTAGACAAGTTTGTCATGCTCATTG

AGGCCAGCCTTACCTACCCCAGTCACTGCTGTGCCTTTGCAAACTGGAG

GCGGCAAACCTCTGAACTTCATCCAATTTGCAACAAGTCTATTTCAAGG

CAAGATATTGATGATATGACTCAGCCTGGGGATCAGAGAGTCTCTCTCG

TAGATGATGAACCCAGTTATGGAAAAGGATCTGACATGTTGTATAGTGA

ATTTGACTATGACTTATGCAATGAATTTGTTGATGTGACCTGCTCGCCA

AAGCCAGATGCATTTAATCCATGTGAAGACATCATGGGGTACAACATCC

TCAGAGTCTTGATATGGTTTATCAGCATCCTGGCCATCACTGGGAACAC

CACAGTGCTGGTGGTCCTGACCACAAGCCAATACAAACTCACTGTGCCC

CGGTTCCTTATGTGTAACCTCGCCTTTGCTGATCTTTGCATTGGGATCT

ACTTGCTACTTATAGCCTCAGTTGATATCCATACTAAGAGCCAGTACCA

CAATTACGCCATTGACTGGCAAACAGGAGCAGGCTGCGATGCCGCTGGC

TTTTTCACTGTCTTTGCCAGTGAACTGTCAGTCTACACATTGGCAGCCA

TAACCCTAGAAAGATGGCATACCATCACACATGCCATGCAACTGGAATG

CAAGGTACAGCTCTGCCATGCTGCCAGCATCATGGTGCTGGGCTGGGCC

TTTGCCTTTGCGGCTGCTCTCTTCCCCATCTTTGGCATCAGTAGCTACA

TGAAAGTGAGCATCTGCCTGCCCATGGATATCGACAGCCCTTTGTCGCA

GCTGTATGTTATGGCCCTCCTCGTACTCAACGCCCTGGCCTTTGTGGTC

ATCTGTGGTTGCTACACCCACATCTACCTCACAGTGAGGAATCCTAACA

TTGTGTCCTCGTCAAGAGACACCAAGATTGCCAAGCGCATGGCCACACT

CATCTTCACGGACTTTCTCTGCATGGCCCCAATTTTATTCTTTGCCATT

TCCGCCTCCCTCAAGGTGCCCCTCATCACTGTGTCCAAGGCCAAGATCC

TCCTAGTTCTGTTCTACCCCATCAATTCTTGTGCCAATCCTTTCCTCTA

TGCCATTTTCACCAAGAACTTCCGCAGGGACTTCTTCGTCCTGATGAGC

AAGTTTGGCTGTTATGAGGTGCAAGCCCAGATTTACAAGACAGAAACCT

CATCTATTACCCACAACTTCCACTCCAGAAAGAATCCCTGTTCCTCGGC

TCCCAGAGTCACCAATAGTTACGTGCTTGTCCCTCTAAATCATTCAGTC

CAGAACTAAAAATCAATGTGAAAATGGATCCTCACCTTGAAAGACAAGT

GTGACTTCTTTCTGGAGAGAGGGCTATGGAAGAGCTGGCAGTGTTGC (underlined region missing (Exon 2) in 3T3.L1 cells)

FSHR Peptide Sequence:
(SEQ ID NO: 31)
MALLLVSLLAFLGSGSGCHHWLCHCSNRVFLCQDSKVTEIPPDLPRNAI

ELRFVLTKLRVIPKGSFSGFGDLEKIEISQNDVLEVIEADVFSNLPNLH

-continued

```
EIRIEKANNLLYINPEAFQNLPSLRYLLISNTGIKHLPAFHKIQSLQKV

LLDIQDNINIHIIARNSFMGLSFESVILWLNKNGIQEIHNCAFNGTQLD

ELNLSDNNNLEELPDDVFQGASGPVVLDISRTKVYSLPNHGLENLKKLR

ARSTYRLKKLPSLDKFVMLIEASLTYPSHCCAFANWRRQTSELHPICNK

SISRQDIDDMTQPGDQRVSLVDDEPSYGKGSDMLYSEFDYDLCNEFVDV

TCSPKPDAFNPCEDIMGYNILRVLIWFISILAITGNTTVLVVLTTSQYK

LTVPRFLMCNLAFADLCIGIYLLLIASVDIHTKSQYHNYAIDWQTGAGC

DAAGFFTVFASELSVYTLAAITLERWHTITHAMQLECKVQLCHAASIMV

LGWAFAFAAALFPIFGISSYMKVSICLPMDIDSPLSQLYVMALLVLNAL

AFVVICGCYTHIYLTVRNPNIVSSSRDTKIAKRMATLIFTDFLCMAPIL

FFAISASLKVPLITVSKAKILLVLFYPINSCANPFLYAIFTKNFRRDFF

VLMSKFGCYEVQAQIYKTETSSITHNFHSRKNPCSSAPRVTNSYVLVPL

NHSVQN
```

Figure 12:
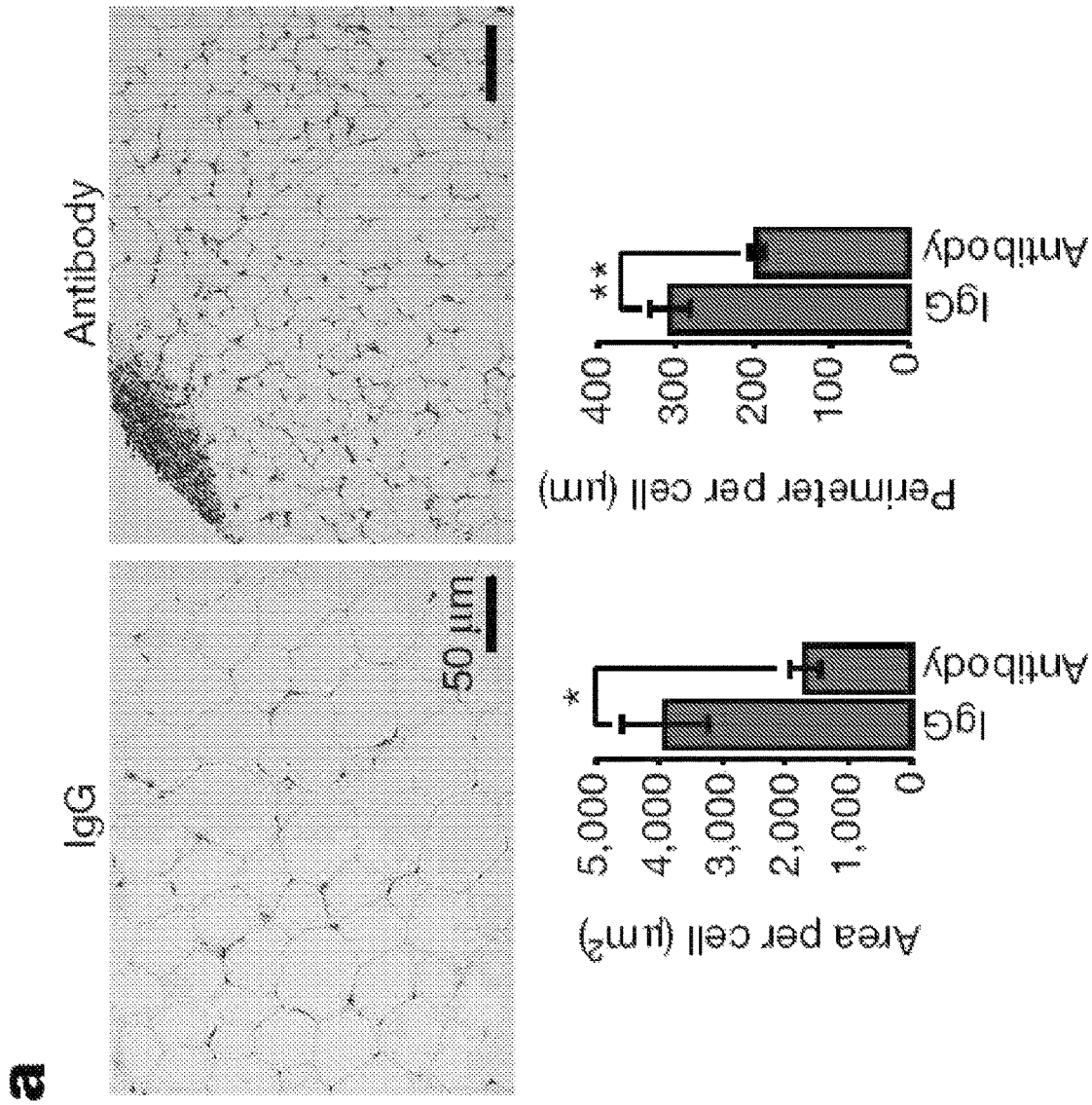
FIGS. 12A, 12B, 12C, and 12D represent that anti-FSH antibody induces beige-like adipose tissue. Cell size and perimeter in haematoxylin and eosin-stained sections of iWAT (FIG. 12A) and Ucp1 immunostaining of iWAT (FIG. 12B) and BAT (FIG. 12C) following injection of anti-FSH antibody or goat IgG (200 μg per mouse per day, intraperitoneal, 8 weeks) to 3-month-old female C57BL/6J mice pair-fed on high-fat diet (n=4 or 5 mice per group).
Figure 12:
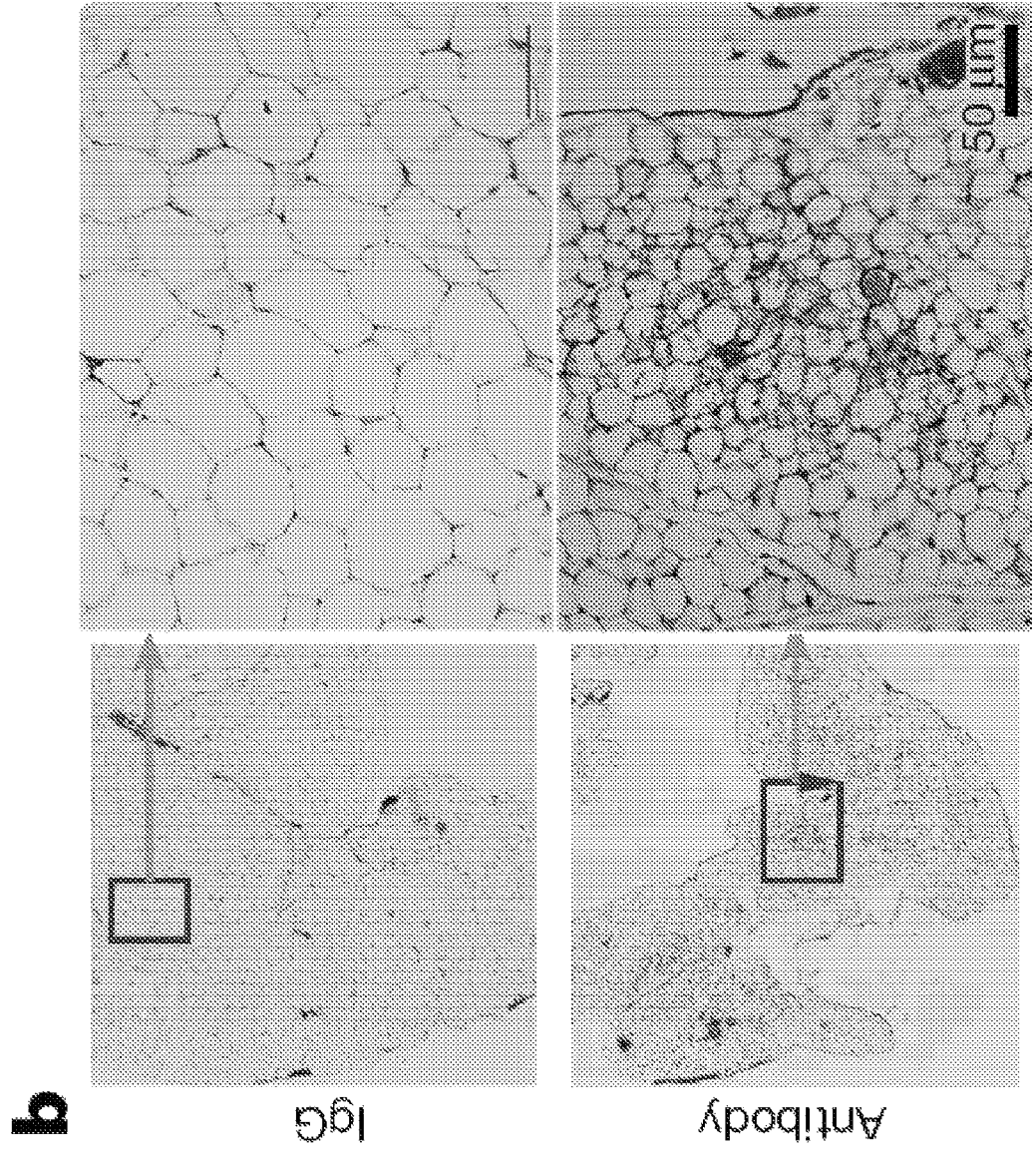
Figure 12:
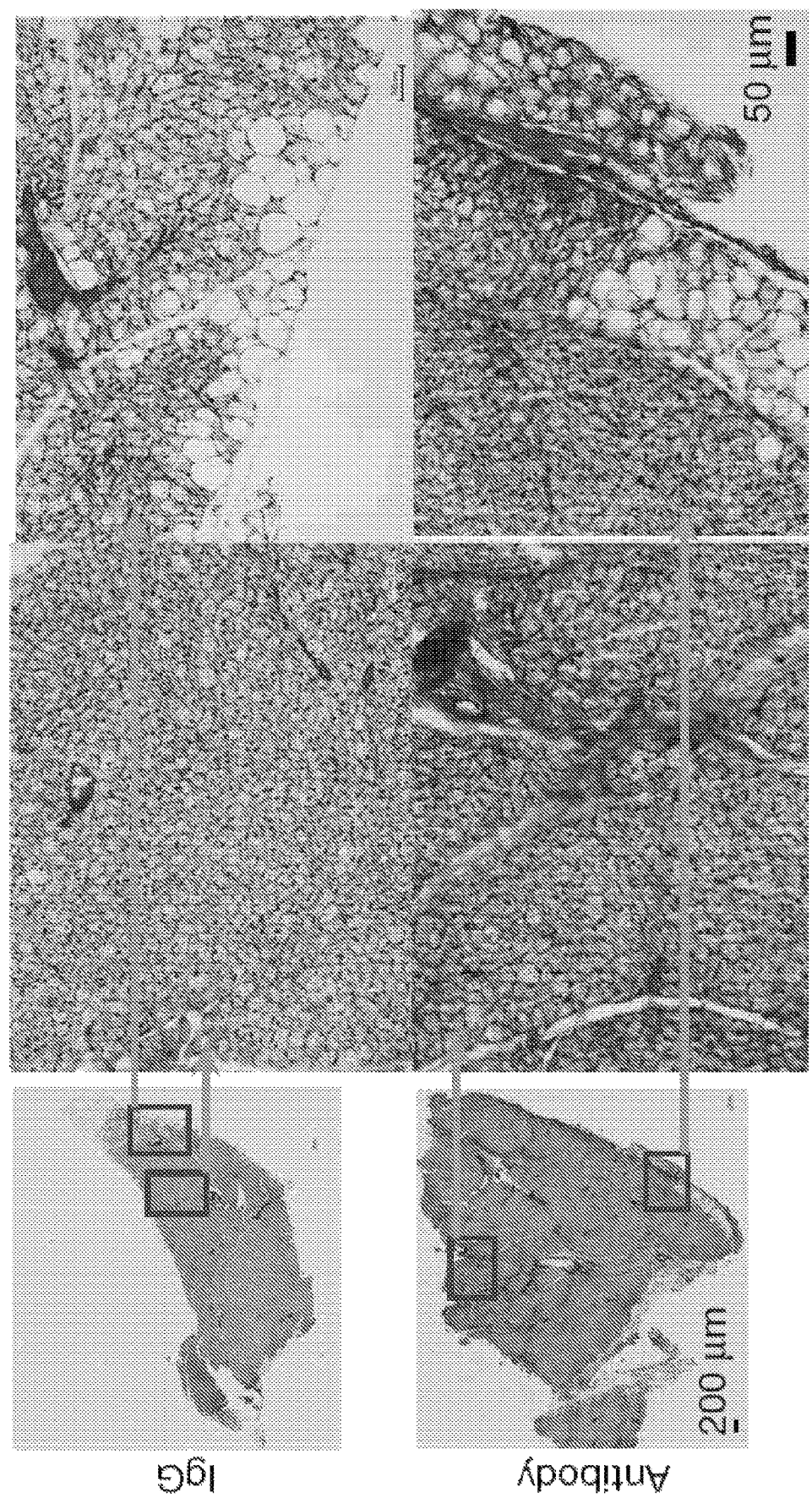
Figure 12:
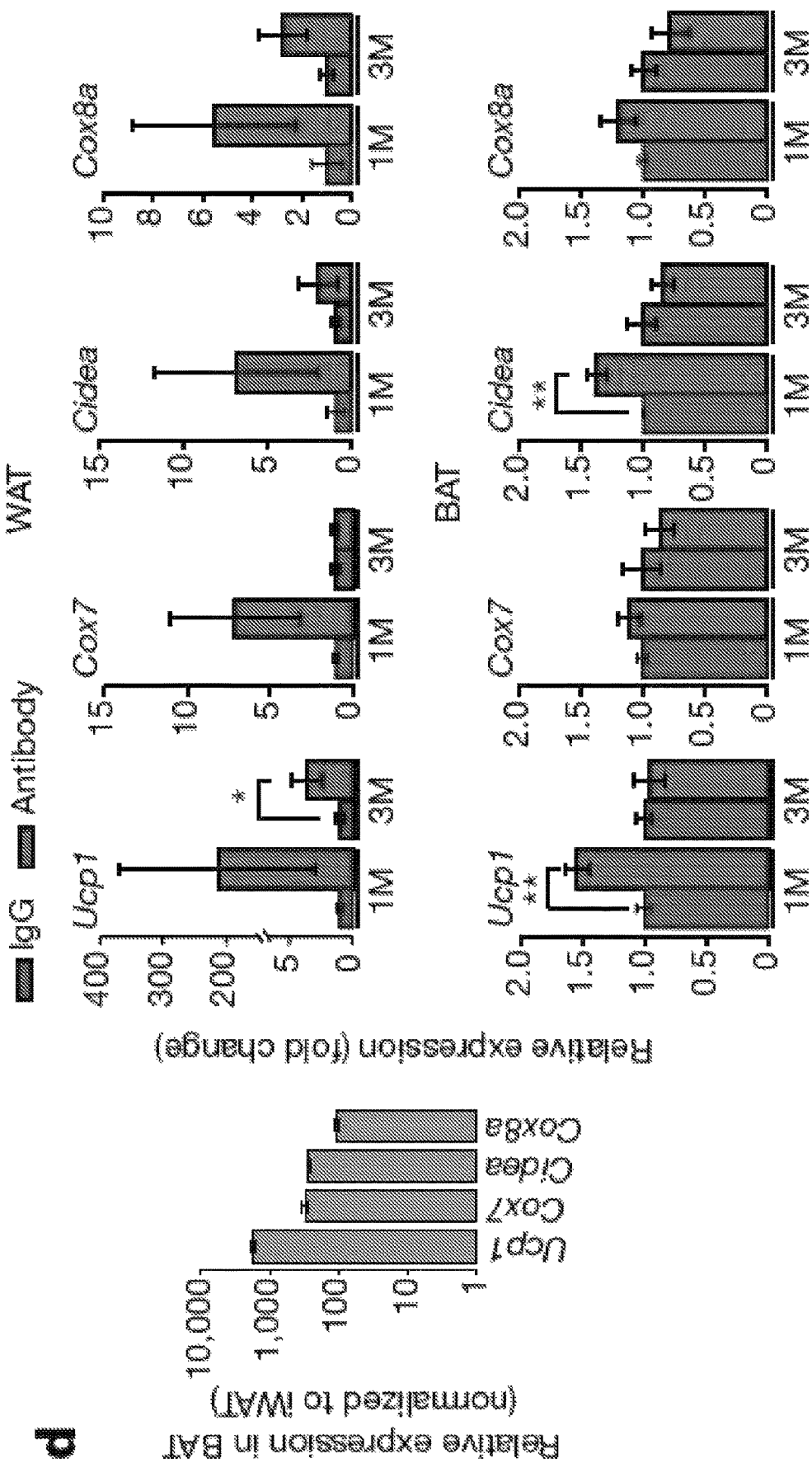
Figure 13:
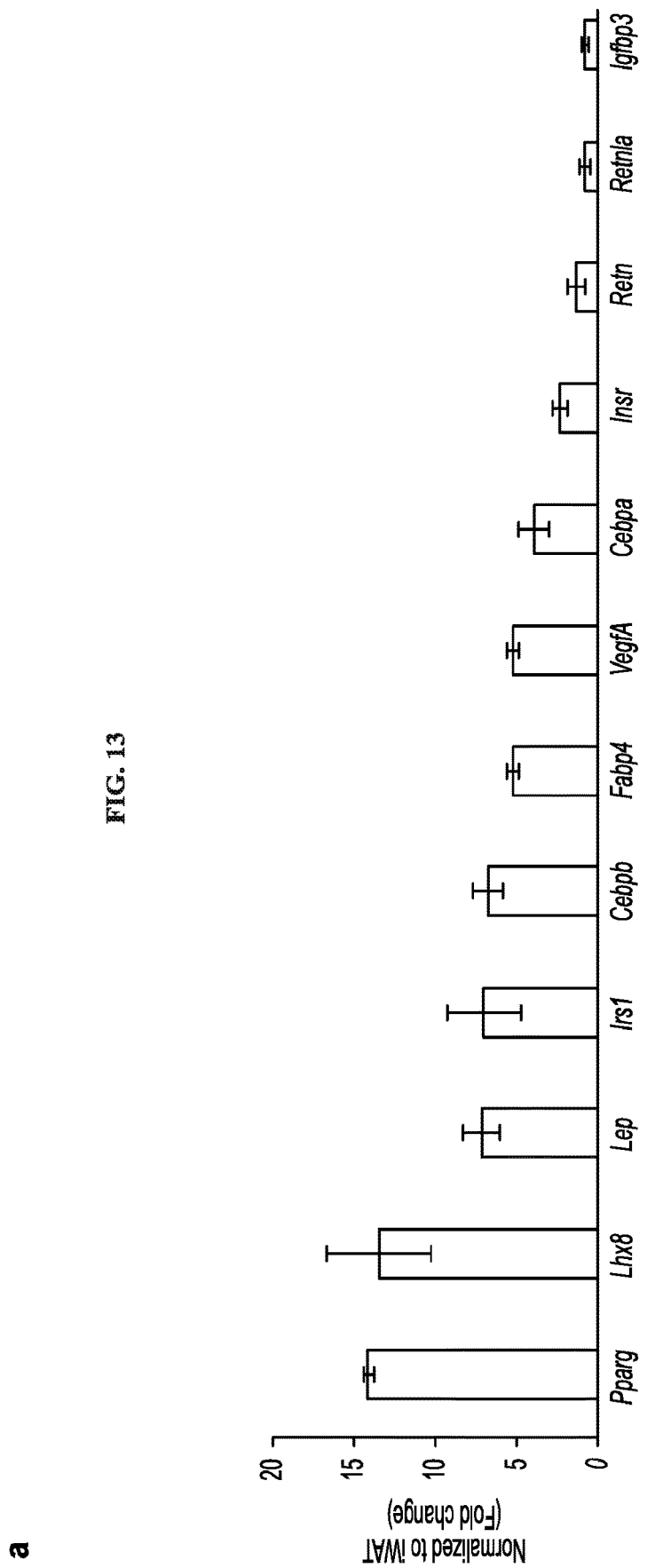
FIGS. 13A and 13B represent that anti-FSH antibody alters gene expression in WAT and BAT. Three-month-old female C57BL/6J mice pair-fed on high-fat diet were injected daily for 8 weeks with anti-FSH antibody or goat IgG (200 μg per mouse per day, intraperitoneally).
Figure 13:
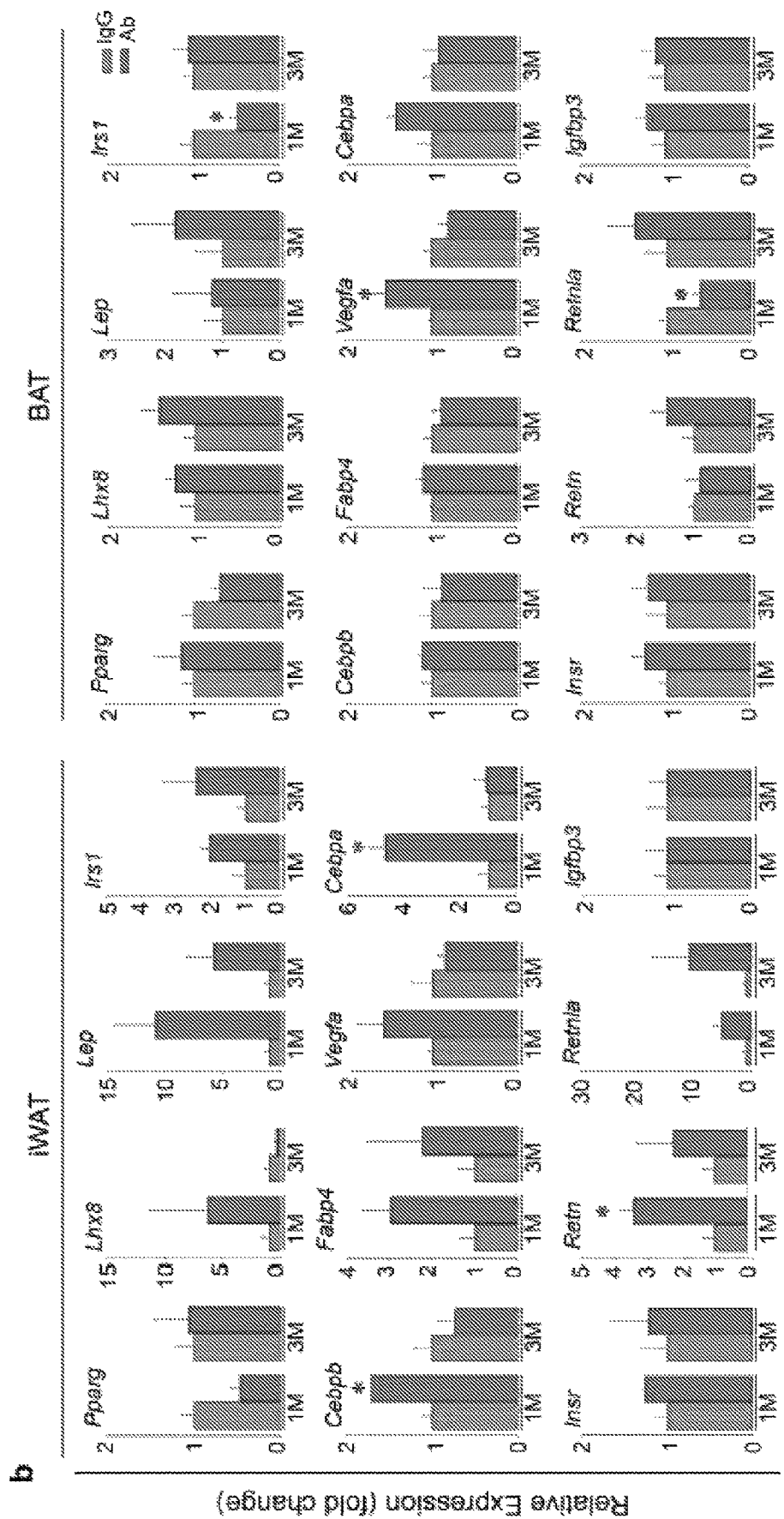

Anti-FSH Antibody Triggers Beiging of White Adipocytes:

To determine whether the Fsh antibody induces Ucp1-rich beige-like adipose tissue in vivo, wild-type mice pair-fed on high-fat diet were injected with anti-FSH antibody or IgG. Anti-FSH-treated mice displayed marked reductions in adipocyte area and perimeter in sections of inguinal fat pads, consistent with adipocyte beiging (FIG. 12A). Furthermore, there was a marked increase in Ucp1 immunolabelling both in iWAT and BAT (FIG. 12B, 12C). This was accompanied at 1 or 3 months with increases in the expression of browning genes in iWAT (FIG. 12D and FIG. 13). Increases were also noted in expression of Ucp1, Cidea, Cebpa and Vegfa in BAT at 1 month, commensurate with the early activation of the thermogenic gene program (FIG. 12D and FIG. 13).

Faithfully phenocopying the effect of antibody treatment, subcutaneous WAT from Fshr+/− mice treated with IgG showed evidence of smaller, beige-like adipocytes with more intense Ucp1 immunostaining (FIG. 6C). This effect was not enhanced by anti-FSH antibody injections into Fshr+/− mice, again confirming the specificity of the anti-FSH antibody (FIG. 6C). It is unknown whether anti-FSH antibody-induced beige adipocytes are derived from a committed adipogenic precursor or from the conversion of mature white adipocytes, or represent a combination of both mechanisms.

Figure 14:
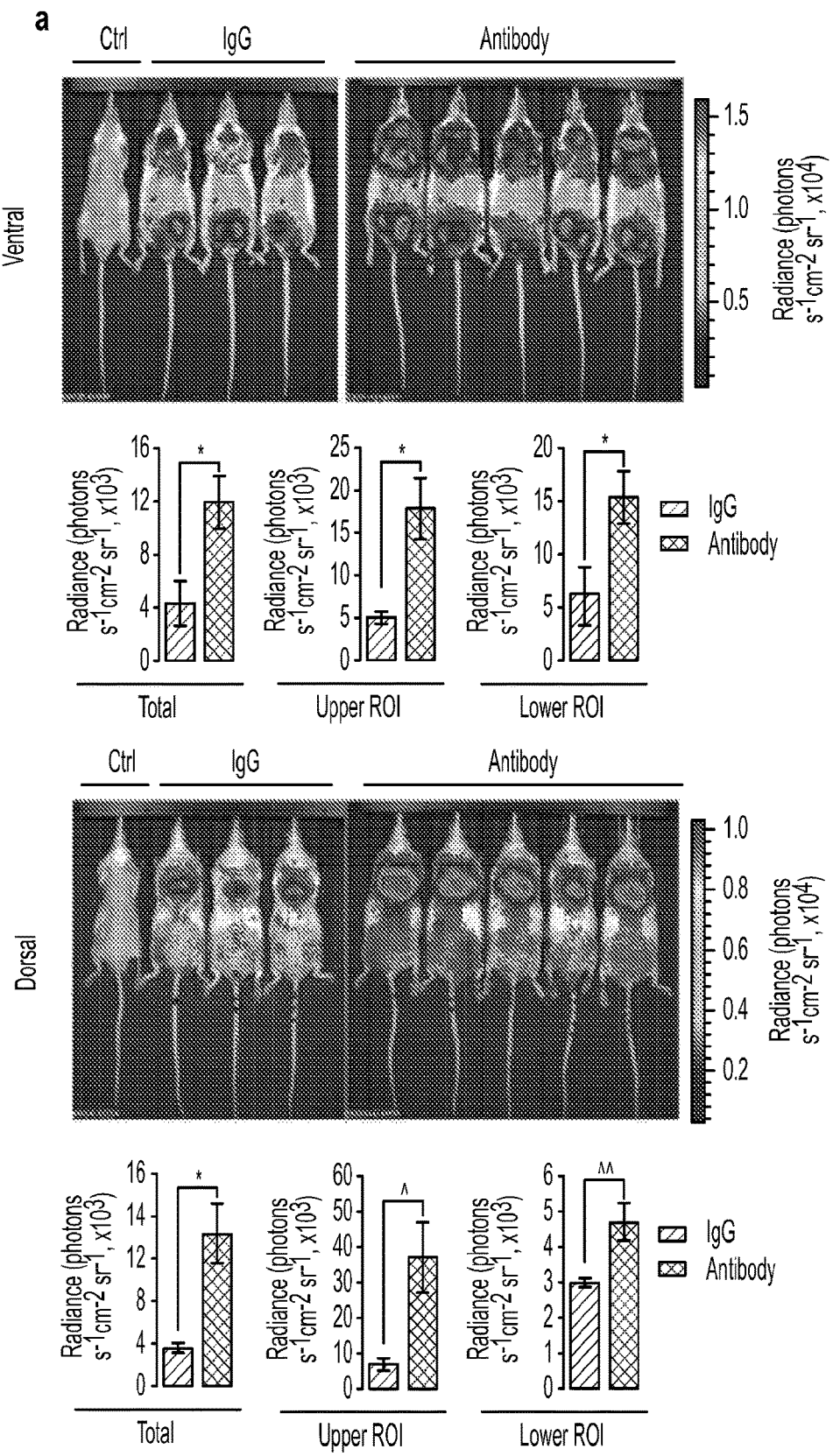
FIGS. 14A, 14B and 14C represent that anti-FSH antibody triggers Ucp1 activation and enhances mitochondrial biogenesis. Three-month-old male ThermoMice pair-fed on high-fat diet and treated with anti-FSH antibody or goat IgG (200 μg per mouse per day) for 8 weeks at room temperature (n as shown) (FIG. 14A) or 2.5 weeks at thermoneutral (30° C.) conditions (n=3 or 4 mice per group) (FIG. 14B). ROI, region of interest. Ctrl, non-transgenic mice injected with d-luciferin. Two-tailed Student's t-test; * P≤0.05, ^P=0.060, ^^P=0.051; mean±s.e.m.
Figure 14:
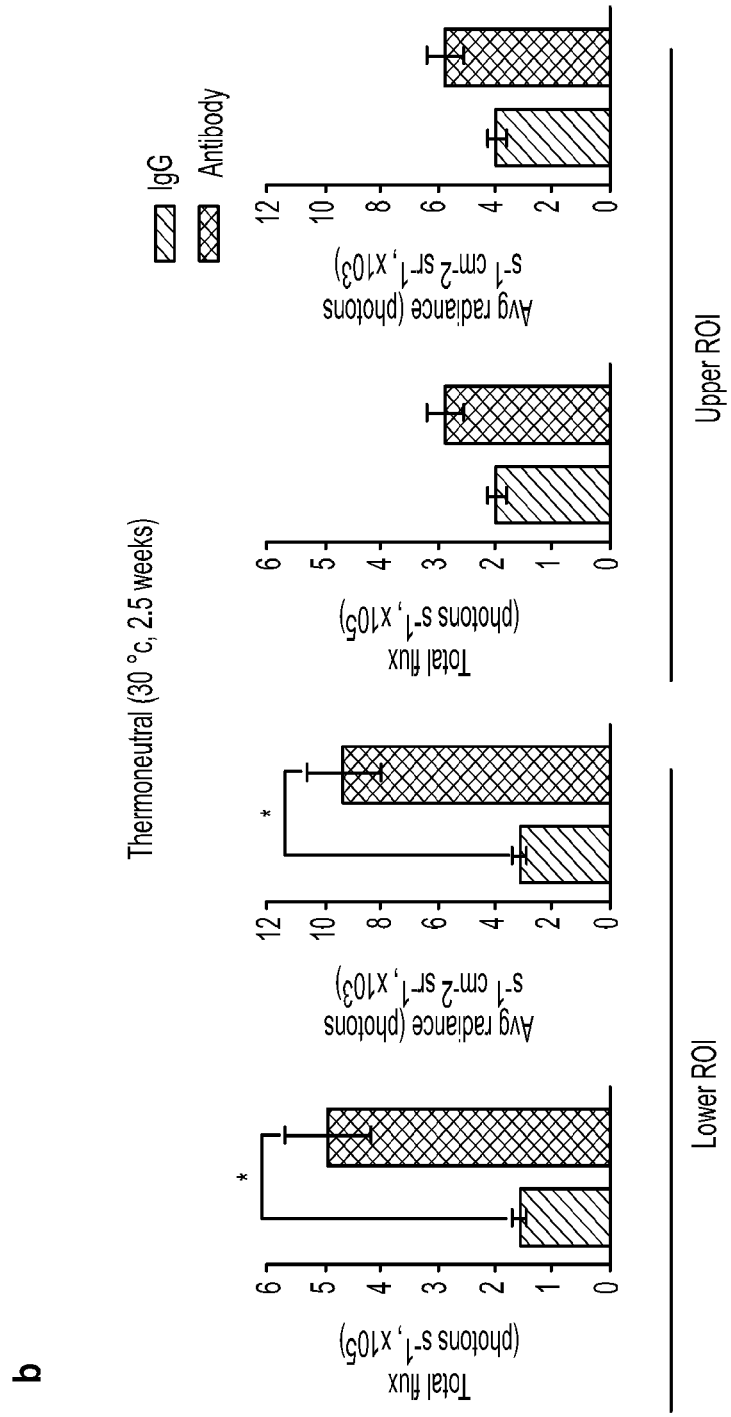
Figure 14:
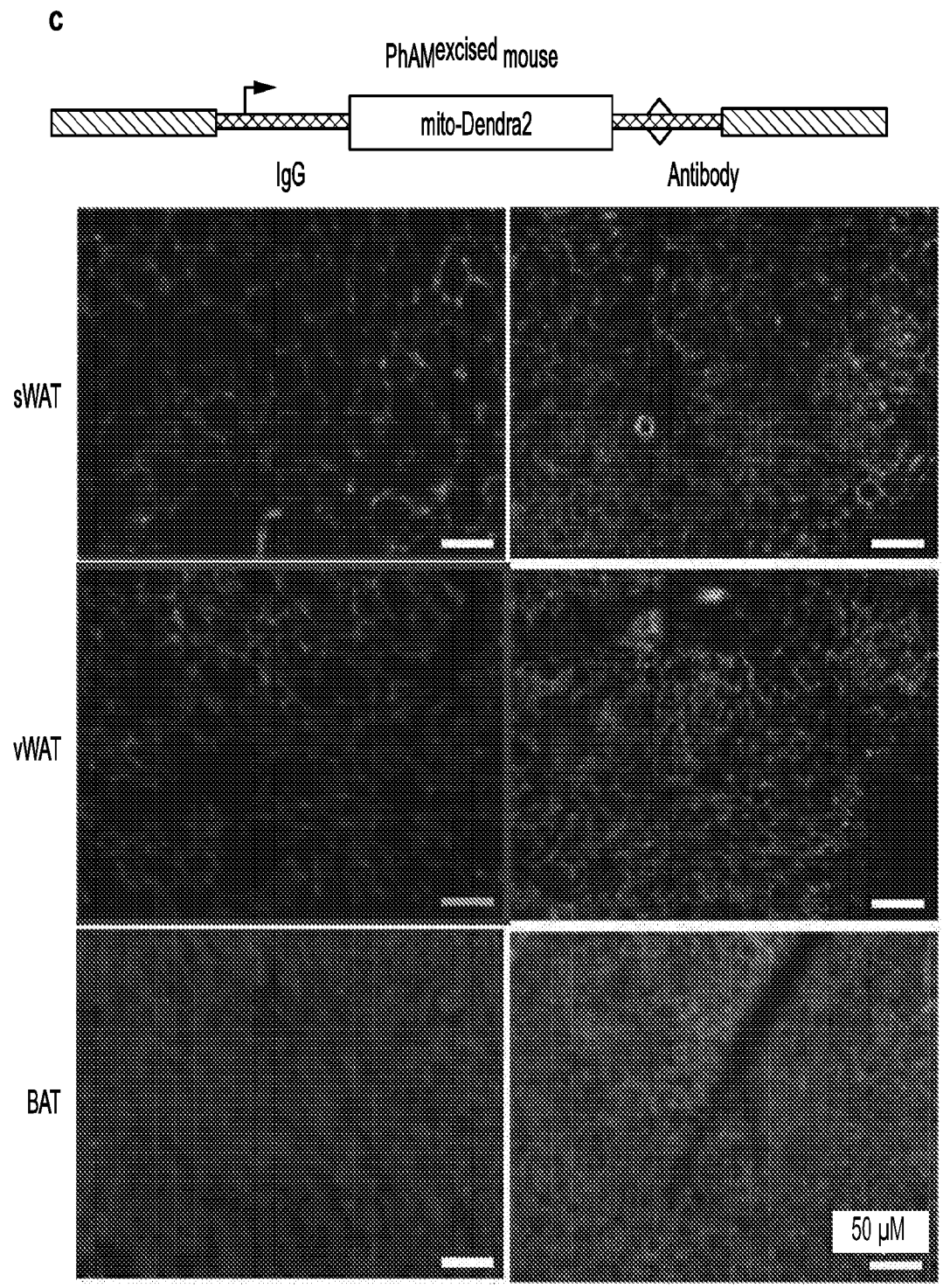

As a complementary in vivo test for beiging, SV129 ThermoMice were imaged (FIG. 14), in which a transgenic Ucp1 promoter drives the Luc2-T2A-tdTomato reporter 10 (FIG. 2D). ThermoMice were pair-fed on a high-fat diet and injected with antibody or IgG (200 μg per mouse per day). Luc2 radiance was measured from both ventral and dorsal surfaces for optimal visualization of inguinal (WAT-rich plus testes) and interscapular (BAT-rich) regions, respectively. Control non-transgenic mice injected with d-luciferin showed no emitted radiance. Antibody treatment triggered marked increases in Luc2 radiance, prominently in the inguinal region, at 8 weeks (FIG. 14A). These increases were equally pronounced with a short, 2.5-week treatment under thermoneutrality (30° C.) (FIG. 14B; see also FIG. 3D). These data together confirm that anti-FSH antibody treatment triggers beiging, which does not result from environmental cold exposure.

Beiging is associated with an increase in mitochondrial density. The PhAM$^{excised}$ mouse was used, in which a fluorescent protein from the octocoral Dendronephthya, Dendra2, is fused to a Cox8 mitochondrial targeting signal, yielding mito-Dendra2 (FIG. 14C). Frozen sections of subcutaneous WAT (SWAT), visceral WAT (vWAT) and BAT from anti-FSH antibody-treated PhAMexcised mice (4 weeks) showed a marked increase in fluorescence, and smaller, more condensed, adipocytes in WAT (FIG. 14C). These data show that FSH blockade induces mitochondrial biogenesis, which is consistent with Ucp1 activation.

3. Deletion of FSHR Gene in Mice Reduces Total Body Fat

Figure 15:
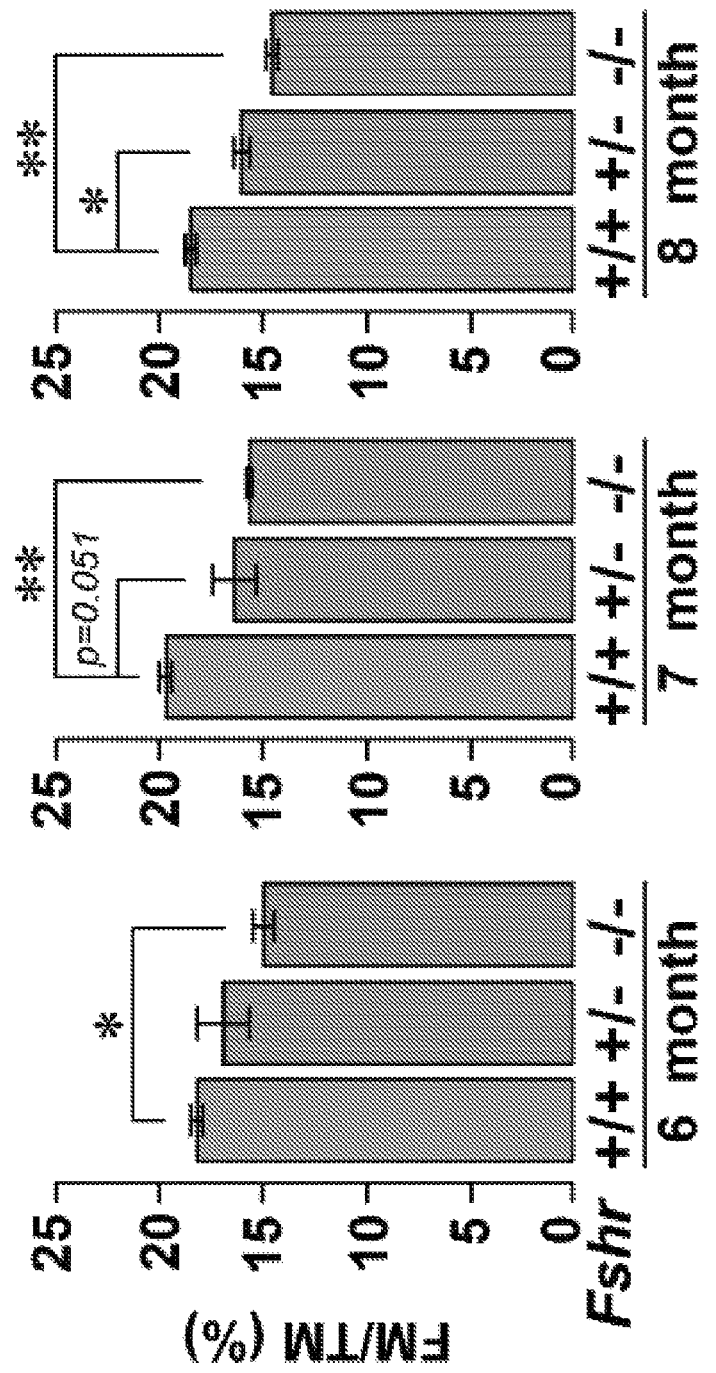
FIG. 15 represents effects of FSHR gene deletion on total body fat measured by dual energy X-ray absorptiometry on total body fat in mice at different ages, as shown.

Studies were undertaken to determine the effects of deleting the FSHR gene in mice on total body fat. Three experimental groups of mice were used; FSHR +/+, FSHR +/−, and FSHR −/− and at three different ages; 6 month, 7 month, and 8 month old mice. As shown in FIG. 15, those mice which were FSHR +/+ exhibited the highest fat mass (FM) to total mass (TM) ratio, while those mice which were FSHR −/− exhibited the lowest FM/TM ratio.

The foregoing examples and description of the preferred embodiments should be taken as illustrating, rather than as limiting the present disclosure as defined by the claims. As will be readily appreciated, numerous variations and combinations of the features set forth above can be utilized without departing from the present disclosure as set forth in the claims. Such variations are not regarded as a departure from the scope of the disclosure, and all such variations are intended to be included within the scope of the following claims. All references cited herein are incorporated by reference in their entireties.

What is claimed is:

1. An anti-FSH antibody, or antigen-binding portion thereof, comprising:
    (i) a heavy chain CDR1 (CDRH1) comprising SEQ ID NO: 9;
    (ii) a heavy chain CDR2 (CDRH2) comprising SEQ ID NO: 10;
    (iii) a heavy chain CDR3 (CDRH3) comprising SEQ ID NO: 11;
    (iv) a light chain CDR1 (CDRL1) comprising SEQ ID NO: 12;
    (v) a light chain CDR2 (CDRL2) comprising SEQ ID NO: 13; and
    (vi) a light chain CDR3 (CDRL3) comprising SEQ ID NO: 14.

2. The anti-FSH antibody, or antigen-binding portion thereof, of claim 1 having a variable heavy chain comprising SEQ ID NO: 7, and a variable light chain comprising SEQ ID NO: 8.

3. The anti-FSH antibody, or antigen-binding portion thereof, of claim 1, wherein the anti-FSH antibody, or antigen-binding portion thereof, specifically binds to one or more epitopes within a β-subunit of FSH.

4. The anti-FSH antibody, or antigen-binding portion thereof, of claim 1, wherein the one or more epitopes within a β-subunit of FSH comprise SEQ ID NO:1 or SEQ ID NO: 2 or a peptide sequence consisting essentially of SEQ ID NO: 1 or SEQ ID NO: 2 but having conservative substitutions.

5. The anti-FSH antibody, or antigen-binding portion thereof, of claim 1, wherein the antibody is a monoclonal antibody.

6. The anti-FSH antibody, or antigen-binding portion thereof, of claim 1, wherein the antibody is a human antibody, a humanized antibody, or a chimeric antibody.

7. The anti-FSH antibody, or antigen-binding portion thereof, of claim 1, wherein the antibody is a humanized antibody.

8. A pharmaceutical composition comprising the anti-FSH antibody, or antigen-binding portion thereof, of claim 1, and a pharmaceutically acceptable carrier or excipient.

9. A nucleic acid sequence encoding the anti-FSH antibody, or antigen-binding portion thereof, of claim 1.

10. The nucleic acid sequence of claim 9 comprising SEQ ID NO: 3 and SEQ ID NO: 4, or a sequence consisting essentially of SEQ ID NO: 3 and SEQ ID NO: 4 but having a codon-optimized sequence encoding the same antibody, or antigen-binding portion thereof.

11. A vector or vector system comprising at least one nucleic acid of claim 9.

12. A cultured cell transformed with the vector or vector system of claim 11.

13. A method of making recombinant anti-FSH antibody, or antigen-binding portion thereof, comprising:
    (i) providing a cell of claim 12;
    (ii) expressing at least one nucleic acid sequence in the vector or vector system of the cell to create at least one of a heavy chain, a light chain, or combinations thereof;
    (iii) collecting a formed anti-FSH antibody, or antigen-binding portion thereof.

14. A cultured non-human cell transformed with the vector or vector system of claim 11.

15. The non-human cell of claim 14, wherein the non-human cell is selected from the group consisting of bacterial cell, a yeast cell, a plant cell, a Chinese hamster ovary (CHO) cell, and a NSO murine myeloma cell.

16. A method of reducing white adipose tissue in a human subject in need thereof comprising administering to said subject a therapeutically effective amount of a composition comprising the anti-FSH antibody, or an antigen-binding portion thereof, of claim 1.

17. The method of claim 16, wherein the anti-FSH antibody, or antigen-binding portion thereof, is selected from the group consisting of a polyclonal antibody, a monoclonal antibody, a humanized antibody, a chimeric antibody, a human antibody, a single-chain variable fragment (scFv), and combinations thereof.

18. The method of claim 16, wherein the method reduces overall body fat in the subject in need thereof.

19. The method of claim 16, wherein the method reduces visceral body fat in the subject in need thereof.

20. A method of inducing thermogenic adipose tissue in a human subject in need thereof comprising administering to said subject a therapeutically effective amount of a composition comprising the anti-FSH antibody, or an antigen-binding portion thereof, of claim 1.

21. A composition comprising the anti-FSH antibody, or antigen-binding portion thereof, of claim 1 for use in reducing white adipose tissue in a human subject.

22. A composition comprising the anti-FSH antibody, or antigen-binding portion thereof, of claim 1 for use in inducing thermogenic adipose tissue in a human subject.

* * * * *

SEQUENCE LISTING

```
<160> NUMBER OF SEQ ID NOS: 31

<210> SEQ ID NO 1
<211> LENGTH: 13
<212> TYPE: PRT
<213> ORGANISM: Homo sapiens

<400> SEQUENCE: 1

Leu Val Tyr Lys Asp Pro Ala Arg Pro Lys Ile Gln Lys
1               5                   10

<210> SEQ ID NO 2
<211> LENGTH: 13
<212> TYPE: PRT
```

-continued

<213> ORGANISM: Mus musculus

<400> SEQUENCE: 2

Leu Val Tyr Lys Asp Pro Ala Arg Pro Asn Thr Gln Lys
1               5                   10

<210> SEQ ID NO 3
<211> LENGTH: 402
<212> TYPE: DNA
<213> ORGANISM: Mus musculus

<400> SEQUENCE: 3

```
atgagagtgc tgattctttt gcggctgttc acagcctttc ctggtatcct gtctgatgtg    60
catcttcagg agtcgggacc tggcctggtg aaaccttctc agtctctgtc cctcacctgc   120
actgtcactg gcttctcaat caccagtgat tatgcctgga actggatccg gcagtttcca   180
ggaaacaaac tggagtggat gggctccata ttttccagtg gtagcattaa ctacaaccca   240
tctctcaaaa gtcgaatctc tatcactcga gacacatcca ggaaccagtt cttcctgcag   300
ttgaattctg tgactactgc ggacgcaggc acatattact gtgcaagagg gggtactggg   360
accgactact ggggccaagg caccactctc acagtctcct ca                      402
```

<210> SEQ ID NO 4
<211> LENGTH: 381
<212> TYPE: DNA
<213> ORGANISM: Mus musculus

<400> SEQUENCE: 4

```
atgatgtcct ctgctcagtt cctttggtctc ctgttgctct gttttcaagg ttccagatgt    60
gatatccaga tgacacagac tacatcctcc ctgtctgcct ctctgggaga cagagtcacc   120
atcagttgca gggcaagtca ggacattagc aattatttaa gctggtatca gcagaaacca   180
gatggaacta ttaaactcct gatctactac acatcacgat acattcagg agtctcgtca   240
aggttcagtg gcagtgggtc tggaacagat tattctctca ccattagcaa cctggagcaa   300
gaagattttg ccacttactt ttgccaacag ggtcatacgc ttcctcccac gttcggaggg   360
gggaccaagc tggaaataaa a                                              381
```

<210> SEQ ID NO 5
<211> LENGTH: 134
<212> TYPE: PRT
<213> ORGANISM: Mus musculus

<400> SEQUENCE: 5

Met Arg Val Leu Ile Leu Leu Arg Leu Phe Thr Ala Phe Pro Gly Ile
1               5                   10                  15

Leu Ser Asp Val His Leu Gln Glu Ser Gly Pro Gly Leu Val Lys Pro
                20                  25                  30

Ser Gln Ser Leu Ser Leu Thr Cys Thr Val Thr Gly Phe Ser Ile Thr
            35                  40                  45

Ser Asp Tyr Ala Trp Asn Trp Ile Arg Gln Phe Pro Gly Asn Lys Leu
        50                  55                  60

Glu Trp Met Gly Ser Ile Phe Ser Gly Ser Ile Asn Tyr Asn Pro
65                  70                  75                  80

Ser Leu Lys Ser Arg Ile Ser Ile Thr Arg Asp Thr Ser Arg Asn Gln
                85                  90                  95

Phe Phe Leu Gln Leu Asn Ser Val Thr Thr Ala Asp Ala Gly Thr Tyr
            100                 105                 110

Tyr Cys Ala Arg Gly Gly Thr Gly Thr Asp Tyr Trp Gly Gln Gly Thr
            115                 120                 125

Thr Leu Thr Val Ser Ser
    130

<210> SEQ ID NO 6
<211> LENGTH: 127
<212> TYPE: PRT
<213> ORGANISM: Mus musculus

<400> SEQUENCE: 6

Met Met Ser Ser Ala Gln Phe Leu Gly Leu Leu Leu Leu Cys Phe Gln
1               5                   10                  15

Gly Ser Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Ser Trp Tyr Gln Gln Lys Pro Asp Gly Thr Ile
    50                  55                  60

Lys Leu Leu Ile Tyr Tyr Thr Ser Arg Leu His Ser Gly Val Ser Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Phe Ala Thr Tyr Phe Cys Gln Gln Gly His
            100                 105                 110

Thr Leu Pro Pro Thr Phe Gly Gly Gly Thr Lys Leu Glu Ile Lys
        115                 120                 125

<210> SEQ ID NO 7
<211> LENGTH: 116
<212> TYPE: PRT
<213> ORGANISM: Mus musculus

<400> SEQUENCE: 7

Asp Val His Leu Gln Glu Ser Gly Pro Gly Leu Val Lys Pro Ser Gln
1               5                   10                  15

Ser Leu Ser Leu Thr Cys Thr Val Thr Gly Phe Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Ser Ile Phe Ser Ser Gly Ser Ile Asn Tyr Asn Pro Ser Leu
    50                  55                  60

Lys Ser Arg Ile Ser Ile Thr Arg Asp Thr Ser Arg Asn Gln Phe Phe
65                  70                  75                  80

Leu Gln Leu Asn Ser Val Thr Thr Ala Asp Ala Gly Thr Tyr Tyr Cys
                85                  90                  95

Ala Arg Gly Gly Thr Gly Thr Asp Tyr Trp Gly Gln Gly Thr Thr Leu
            100                 105                 110

Thr Val Ser Ser
    115

<210> SEQ ID NO 8
<211> LENGTH: 107
<212> TYPE: PRT
<213> ORGANISM: Mus musculus

<400> SEQUENCE: 8

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Ser Trp Tyr Gln Gln Lys Pro Asp Gly Thr Ile Lys Leu Leu Ile
            35                  40                  45

Tyr Tyr Thr Ser Arg Leu His Ser Gly Val Ser Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly His Thr Leu Pro Pro
                85                  90                  95

Thr Phe Gly Gly Gly Thr Lys Leu Glu Ile Lys
            100                 105
```

<210> SEQ ID NO 9
<211> LENGTH: 6
<212> TYPE: PRT
<213> ORGANISM: Mus musculus

<400> SEQUENCE: 9

```
Ser Asp Tyr Ala Trp Asn
1               5
```

<210> SEQ ID NO 10
<211> LENGTH: 16
<212> TYPE: PRT
<213> ORGANISM: Mus musculus

<400> SEQUENCE: 10

```
Ser Ile Phe Ser Ser Gly Ser Ile Asn Tyr Asn Pro Ser Leu Lys Ser
1               5                   10                  15
```

<210> SEQ ID NO 11
<211> LENGTH: 7
<212> TYPE: PRT
<213> ORGANISM: Mus musculus

<400> SEQUENCE: 11

```
Gly Gly Thr Gly Thr Asp Tyr
1               5
```

<210> SEQ ID NO 12
<211> LENGTH: 11
<212> TYPE: PRT
<213> ORGANISM: Mus musculus

<400> SEQUENCE: 12

```
Arg Ala Ser Gln Asp Ile Ser Asn Tyr Leu Ser
1               5                   10
```

<210> SEQ ID NO 13
<211> LENGTH: 7
<212> TYPE: PRT
<213> ORGANISM: Mus musculus

<400> SEQUENCE: 13

```
Tyr Thr Ser Arg Leu His Ser
1               5
```

<210> SEQ ID NO 14
<211> LENGTH: 9

```
<212> TYPE: PRT
<213> ORGANISM: Mus musculus

<400> SEQUENCE: 14

Gln Gln Gly His Thr Leu Pro Pro Thr
1               5

<210> SEQ ID NO 15
<211> LENGTH: 11
<212> TYPE: PRT
<213> ORGANISM: Mus musculus

<400> SEQUENCE: 15

Cys Ala Arg Gly Gly Thr Gly Thr Asp Tyr Val
1               5                   10

<210> SEQ ID NO 16
<211> LENGTH: 11
<212> TYPE: PRT
<213> ORGANISM: Mus musculus

<400> SEQUENCE: 16

Cys Gln Gln Gly His Thr Leu Pro Pro Thr Phe
1               5                   10

<210> SEQ ID NO 17
<211> LENGTH: 219
<212> TYPE: PRT
<213> ORGANISM: Artificial
<220> FEATURE:
<223> OTHER INFORMATION: Synthetic

<400> SEQUENCE: 17

His Ser Cys Glu Leu Thr Asn Ile Thr Ile Ser Val Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Asn Thr Gln
        35                  40                  45

Lys Val Cys Thr Phe Lys Glu Leu Val Tyr Glu Thr Val Arg Leu Pro
    50                  55                  60

Gly Cys Ala Arg His Ser Asp Ser Leu Tyr Thr Tyr Pro Val Ala Thr
65                  70                  75                  80

Glu Cys His Cys Gly Lys Cys Asp Ser Asp Ser Thr Asp Cys Thr Val
                85                  90                  95

Arg Gly Leu Gly Pro Ser Tyr Cys Ser Phe Ser Glu Met Lys Glu Gly
            100                 105                 110

Gly Gly Ser Gly Gly Ser Gly Gly Ser Leu Pro Asp Gly Asp
        115                 120                 125

Phe Ile Ile Gln Gly Cys Pro Glu Cys Lys Leu Lys Glu Asn Lys Tyr
130                 135                 140

Phe Ser Lys Leu Gly Ala Pro Ile Tyr Gln Cys Met Gly Cys Cys Phe
145                 150                 155                 160

Ser Arg Ala Tyr Pro Thr Pro Ala Arg Ser Lys Lys Thr Met Leu Val
                165                 170                 175

Pro Lys Asn Ile Thr Ser Glu Ala Thr Cys Cys Val Ala Lys Ala Phe
            180                 185                 190

Thr Lys Ala Thr Val Met Gly Asn Ala Arg Val Glu Asn His Thr Glu
        195                 200                 205
```

Cys His Cys Ser Thr Cys Tyr Tyr His Lys Ser
    210                 215

<210> SEQ ID NO 18
<211> LENGTH: 27
<212> TYPE: PRT
<213> ORGANISM: Artificial
<220> FEATURE:
<223> OTHER INFORMATION: Synthetic

<400> SEQUENCE: 18

Glu Gly Gly Gly Ser Gly Gly Ser Gly Gly Gly Ser Leu Pro Asp
1               5                   10                  15

Gly Asp Phe Ile Gln Gly Cys Pro Glu Cys Lys
            20                  25

<210> SEQ ID NO 19
<211> LENGTH: 13
<212> TYPE: PRT
<213> ORGANISM: Artificial
<220> FEATURE:
<223> OTHER INFORMATION: Synthetic

<400> SEQUENCE: 19

Val Cys Thr Phe Lys Glu Leu Val Tyr Glu Thr Val Arg
1               5                   10

<210> SEQ ID NO 20
<211> LENGTH: 13
<212> TYPE: PRT
<213> ORGANISM: Artificial
<220> FEATURE:
<223> OTHER INFORMATION: Synthetic

<400> SEQUENCE: 20

Gly Leu Gly Pro Ser Tyr Cys Ser Phe Ser Glu Met Lys
1               5                   10

<210> SEQ ID NO 21
<211> LENGTH: 11
<212> TYPE: PRT
<213> ORGANISM: Artificial
<220> FEATURE:
<223> OTHER INFORMATION: Synthetic

<400> SEQUENCE: 21

Cys Asp Ser Asp Ser Thr Asp Cys Thr Val Arg
1               5                   10

<210> SEQ ID NO 22
<211> LENGTH: 15
<212> TYPE: PRT
<213> ORGANISM: Artificial
<220> FEATURE:
<223> OTHER INFORMATION: Synthetic

<400> SEQUENCE: 22

Leu Gly Ala Pro Ile Tyr Gln Cys Met Gly Cys Cys Phe Ser Arg
1               5                   10                  15

<210> SEQ ID NO 23
<211> LENGTH: 13
<212> TYPE: PRT
<213> ORGANISM: Artificial
<220> FEATURE:
<223> OTHER INFORMATION: Synthetic

```
<400> SEQUENCE: 23

Gly Leu Gly Pro Ser Tyr Cys Phe Ser Phe Glu Met Lys
1               5                   10

<210> SEQ ID NO 24
<211> LENGTH: 18
<212> TYPE: PRT
<213> ORGANISM: Artificial
<220> FEATURE:
<223> OTHER INFORMATION: Synthetic

<400> SEQUENCE: 24

His Ser Asp Ser Leu Tyr Thr Tyr Pro Val Ala Thr Glu Cys Gly Cys
1               5                   10                  15

Gly Lys

<210> SEQ ID NO 25
<211> LENGTH: 15
<212> TYPE: PRT
<213> ORGANISM: Artificial
<220> FEATURE:
<223> OTHER INFORMATION: Synthetic

<400> SEQUENCE: 25

Leu Gly Ala Pro Ile Tyr Gln Cys Met Gly Cys Cys Phe Ser Arg
1               5                   10                  15

<210> SEQ ID NO 26
<211> LENGTH: 16
<212> TYPE: PRT
<213> ORGANISM: Artificial
<220> FEATURE:
<223> OTHER INFORMATION: Synthetic

<400> SEQUENCE: 26

Val Glu Asn His Thr Glu Cys His Cys Ser Thr Cys Tyr Tyr His Lys
1               5                   10                  15

<210> SEQ ID NO 27
<211> LENGTH: 14
<212> TYPE: PRT
<213> ORGANISM: Artificial
<220> FEATURE:
<223> OTHER INFORMATION: Synthetic

<400> SEQUENCE: 27

Asp Leu Val Tyr Lys Asp Pro Ala Arg Pro Asn Thr Gln Lys
1               5                   10

<210> SEQ ID NO 28
<211> LENGTH: 8
<212> TYPE: PRT
<213> ORGANISM: Artificial
<220> FEATURE:
<223> OTHER INFORMATION: Synthetic

<400> SEQUENCE: 28

Glu Leu Val Tyr Glu Thr Val Arg
1               5

<210> SEQ ID NO 29
<211> LENGTH: 6
<212> TYPE: PRT
<213> ORGANISM: Artificial
<220> FEATURE:
<223> OTHER INFORMATION: Synthetic
```

<400> SEQUENCE: 29

Thr Met Leu Val Pro Lys
1               5

<210> SEQ ID NO 30
<211> LENGTH: 2203
<212> TYPE: DNA
<213> ORGANISM: Mus musculus

<400> SEQUENCE: 30

| | | | | | |
|---|---|---|---|---|---|
| tgagcaggca | gaaagcaggt | ggatggataa | aataagcatg | gccttgctcc | tggtctcctt | 60 |
| gctggcattc | ttgggctcgg | gatctggatg | tcatcactgg | ctgtgtcatt | gctctaacag | 120 |
| ggtcttcctc | tgccaagata | gcaaggtgac | cgagattccg | cccgacctcc | cccggaacgc | 180 |
| cattgaactg | agatttgtgc | tcaccaagct | tcgagtcatt | ccaaaaggat | cattttctgg | 240 |
| atttggggac | ctggagaaaa | tagagatctc | tcagaatgat | gtcttggagg | taatagaggc | 300 |
| agatgtgttc | tccaacctac | ccaacttgca | tgaaattagg | attgaaaagg | ctaacaatct | 360 |
| gctgtacatc | aaccctgagg | ccttccagaa | tcttcccagt | ctccgatatc | tgttaatatc | 420 |
| caacacaggc | attaaacact | tgccagcctt | tcacaagatc | cagtctctcc | aaaaggtttt | 480 |
| attagacatt | caagataaca | taaacatcca | catcattgcc | aggaactcct | tcatgggact | 540 |
| gagctttgaa | agtgtaattc | tatggctgaa | taagaatggg | attcaagaaa | tacacaactg | 600 |
| tgcattcaac | ggaacccagc | tagatgaact | gaatctaagc | gataacaata | atttggaaga | 660 |
| attgcctgat | gatgttttcc | agggagcctc | tgggccagtc | gttttagaca | tctcaaggac | 720 |
| aaaggtctat | tccctgccca | accatggctt | agaaaatctg | aagaagttga | gggccaggtc | 780 |
| aacataccgc | ttgaaaaagc | tccctagtct | agacaagttt | gtcatgctca | ttgaggccag | 840 |
| ccttacctac | cccagtcact | gctgtgcctt | tgcaaactgg | aggcggcaaa | cctctgaact | 900 |
| tcatccaatt | tgcaacaagt | ctatttcaag | gcaagatatt | gatgatatga | ctcagcctgg | 960 |
| ggatcagaga | gtctctctcg | tagatgatga | acccagttat | ggaaaaggat | ctgacatgtt | 1020 |
| gtatagtgaa | tttgactatg | acttatgcaa | tgaatttgtt | gatgtgacct | gctcgccaaa | 1080 |
| gccagatgca | tttaatccat | gtgaagacat | catggggtac | aacatcctca | gagtcttgat | 1140 |
| atggtttatc | agcatcctgg | ccatcactgg | gaacaccaca | gtgctggtgg | tcctgaccac | 1200 |
| aagccaatac | aaactcactg | tgccccggtt | ccttatgtgt | aacctcgcct | tgctgatct | 1260 |
| ttgcattggg | atctacttgc | tactatagc | ctcagttgat | atccatacta | agagccagta | 1320 |
| ccacaattac | gccattgact | ggcaaacagg | agcaggctgc | gatgccgctg | cttttttcac | 1380 |
| tgtctttgcc | agtgaactgt | cagtctacac | attggcagcc | ataaccctag | aaagatggca | 1440 |
| taccatcaca | catgccatgc | aactggaatg | caaggtacag | ctctgccatg | ctgccagcat | 1500 |
| catggtgctg | ggctgggcct | tgcctttgc | ggctgctctc | ttcccatct | ttggcatcag | 1560 |
| tagctacatg | aaagtgagca | tctgcctgcc | catggatatc | gacagccctt | tgtcgcagct | 1620 |
| gtatgttatg | gccctcctcg | tactcaacgc | cctggccttt | gtggtcatct | gtggttgcta | 1680 |
| cacccacatc | tacctcacag | tgaggaatcc | taacattgtg | tcctcgtcaa | gagacaccaa | 1740 |
| gattgccaag | cgcatggcca | cactcatctt | cacggacttt | ctctgcatgg | ccccaatttt | 1800 |
| attctttgcc | atttccgcct | ccctcaaggt | gcccctcatc | actgtgtcca | aggccaagat | 1860 |
| cctcctagtt | ctgttctacc | ccatcaattc | ttgtgccaat | cctttcctct | atgccatttt | 1920 |
| caccaagaac | ttccgcaggg | acttcttcgt | cctgatgagc | aagtttggct | gttatgaggt | 1980 |

```
gcaagcccag atttacaaga cagaaacctc atctattacc cacaacttcc actccagaaa    2040
gaatccctgt tcctcggctc ccagagtcac caatagttac gtgcttgtcc ctctaaatca    2100
ttcagtccag aactaaaaat caatgtgaaa atggatcctc accttgaaag acaagtgtga    2160
cttctttctg gagagagggc tatggaagag ctggcagtgt tgc                      2203

<210> SEQ ID NO 31
<211> LENGTH: 692
<212> TYPE: PRT
<213> ORGANISM: Mus musculus

<400> SEQUENCE: 31

Met Ala Leu Leu Leu Val Ser Leu Leu Ala Phe Leu Gly Ser Gly Ser
1               5                   10                  15

Gly Cys His His Trp Leu Cys His Cys Ser Asn Arg Val Phe Leu Cys
            20                  25                  30

Gln Asp Ser Lys Val Thr Glu Ile Pro Pro Asp Leu Pro Arg Asn Ala
        35                  40                  45

Ile Glu Leu Arg Phe Val Leu Thr Lys Leu Arg Val Ile Pro Lys Gly
    50                  55                  60

Ser Phe Ser Gly Phe Gly Asp Leu Glu Lys Ile Glu Ile Ser Gln Asn
65                  70                  75                  80

Asp Val Leu Glu Val Ile Glu Ala Asp Val Phe Ser Asn Leu Pro Asn
                85                  90                  95

Leu His Glu Ile Arg Ile Glu Lys Ala Asn Asn Leu Leu Tyr Ile Asn
            100                 105                 110

Pro Glu Ala Phe Gln Asn Leu Pro Ser Leu Arg Tyr Leu Leu Ile Ser
        115                 120                 125

Asn Thr Gly Ile Lys His Leu Pro Ala Phe His Lys Ile Gln Ser Leu
    130                 135                 140

Gln Lys Val Leu Leu Asp Ile Gln Asp Asn Ile Asn Ile His Ile Ile
145                 150                 155                 160

Ala Arg Asn Ser Phe Met Gly Leu Ser Phe Glu Ser Val Ile Leu Trp
                165                 170                 175

Leu Asn Lys Asn Gly Ile Gln Glu Ile His Asn Cys Ala Phe Asn Gly
            180                 185                 190

Thr Gln Leu Asp Glu Leu Asn Leu Ser Asp Asn Asn Leu Glu Glu
        195                 200                 205

Leu Pro Asp Asp Val Phe Gln Gly Ala Ser Gly Pro Val Val Leu Asp
    210                 215                 220

Ile Ser Arg Thr Lys Val Tyr Ser Leu Pro Asn His Gly Leu Glu Asn
225                 230                 235                 240

Leu Lys Lys Leu Arg Ala Arg Ser Thr Tyr Arg Leu Lys Lys Leu Pro
                245                 250                 255

Ser Leu Asp Lys Phe Val Met Leu Ile Glu Ala Ser Leu Thr Tyr Pro
            260                 265                 270

Ser His Cys Cys Ala Phe Ala Asn Trp Arg Arg Gln Thr Ser Glu Leu
        275                 280                 285

His Pro Ile Cys Asn Lys Ser Ile Ser Arg Gln Asp Ile Asp Asp Met
    290                 295                 300

Thr Gln Pro Gly Asp Gln Arg Val Ser Leu Val Asp Glu Pro Ser
305                 310                 315                 320

Tyr Gly Lys Gly Ser Asp Met Leu Tyr Ser Glu Phe Tyr Asp Leu
                325                 330                 335
```

```
Cys Asn Glu Phe Val Asp Val Thr Cys Ser Pro Lys Pro Asp Ala Phe
            340                 345                 350

Asn Pro Cys Glu Asp Ile Met Gly Tyr Asn Ile Leu Arg Val Leu Ile
        355                 360                 365

Trp Phe Ile Ser Ile Leu Ala Ile Thr Gly Asn Thr Thr Val Leu Val
370                 375                 380

Val Leu Thr Thr Ser Gln Tyr Lys Leu Thr Val Pro Arg Phe Leu Met
385                 390                 395                 400

Cys Asn Leu Ala Phe Ala Asp Leu Cys Ile Gly Ile Tyr Leu Leu Leu
                405                 410                 415

Ile Ala Ser Val Asp Ile His Thr Lys Ser Gln Tyr His Asn Tyr Ala
            420                 425                 430

Ile Asp Trp Gln Thr Gly Ala Gly Cys Asp Ala Ala Gly Phe Phe Thr
            435                 440                 445

Val Phe Ala Ser Glu Leu Ser Val Tyr Thr Leu Ala Ala Ile Thr Leu
450                 455                 460

Glu Arg Trp His Thr Ile Thr His Ala Met Gln Leu Glu Cys Lys Val
465                 470                 475                 480

Gln Leu Cys His Ala Ala Ser Ile Met Val Leu Gly Trp Ala Phe Ala
                485                 490                 495

Phe Ala Ala Ala Leu Phe Pro Ile Phe Gly Ile Ser Ser Tyr Met Lys
                500                 505                 510

Val Ser Ile Cys Leu Pro Met Asp Ile Asp Ser Pro Leu Ser Gln Leu
            515                 520                 525

Tyr Val Met Ala Leu Leu Val Leu Asn Ala Leu Ala Phe Val Val Ile
            530                 535                 540

Cys Gly Cys Tyr Thr His Ile Tyr Leu Thr Val Arg Asn Pro Asn Ile
545                 550                 555                 560

Val Ser Ser Ser Arg Asp Thr Lys Ile Ala Lys Arg Met Ala Thr Leu
                565                 570                 575

Ile Phe Thr Asp Phe Leu Cys Met Ala Pro Ile Leu Phe Phe Ala Ile
            580                 585                 590

Ser Ala Ser Leu Lys Val Pro Leu Ile Thr Val Ser Lys Ala Lys Ile
            595                 600                 605

Leu Leu Val Leu Phe Tyr Pro Ile Asn Ser Cys Ala Asn Pro Phe Leu
610                 615                 620

Tyr Ala Ile Phe Thr Lys Asn Phe Arg Arg Asp Phe Phe Val Leu Met
625                 630                 635                 640

Ser Lys Phe Gly Cys Tyr Glu Val Gln Ala Gln Ile Tyr Lys Thr Glu
                645                 650                 655

Thr Ser Ser Ile Thr His Asn Phe His Ser Arg Lys Asn Pro Cys Ser
            660                 665                 670

Ser Ala Pro Arg Val Thr Asn Ser Tyr Val Leu Val Pro Leu Asn His
            675                 680                 685

Ser Val Gln Asn
            690
```